United States Patent
Kato et al.

(10) Patent No.: US 6,586,475 B1
(45) Date of Patent: Jul. 1, 2003

(54) β-AMYLOID PROTEIN PRODUCTION/SECRETION INHIBITORS

(75) Inventors: Kaneyoshi Kato, Kawanishi (JP); Jun Terauchi, Ikeda (JP); Hiroaki Fukumoto, Cambridge, MA (US); Mitsuru Kakihana, Kobe (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 09/856,317

(22) PCT Filed: Nov. 16, 1999

(86) PCT No.: PCT/JP99/06450
§ 371 (c)(1),
(2), (4) Date: Jun. 5, 2001

(87) PCT Pub. No.: WO00/31021
PCT Pub. Date: Jun. 2, 2000

(30) Foreign Application Priority Data

Nov. 20, 1998 (JP) .............................. 10-331018

(51) Int. Cl.$^7$ .................... A61K 31/165; C07C 235/10; C07C 237/22; C07C 237/42; C07C 235/50
(52) U.S. Cl. ....................... 514/622; 564/171
(58) Field of Search ........................... 564/171; 514/622

(56) References Cited

FOREIGN PATENT DOCUMENTS

| EP | 0 322 823 | 7/1989 |
|----|-----------|--------|
| EP | 487745 | 6/1992 |
| EP | 0 611 003 | 8/1994 |
| GB | 1 471 276 | 4/1977 |
| JP | 5-239005 | 9/1993 |
| WO | 94/01408 | 1/1994 |
| WO | 97/28129 | 8/1997 |
| WO | 98/17648 | 4/1998 |
| WO | 98/38156 | 9/1998 |
| WO | 99/13871 | 3/1999 |

OTHER PUBLICATIONS

Maglio et al., Chemical Abstracts, vol. 129:316646, 1998.*
El Sebai A. Ibrahim et al. "Synthesis of 4–Substituted Aminobenzoate Quaternary Salts as Potent Antispasmodic Agents", Journal of Pharmaceutical Sciences, vol. 68, No. 3, pp. 332–335, Mar. 1979.
M. Biava et al. "Synthesis and Antimycobacterial Activity of New Aminoderivatives of ortho–, meta–and para–toluidine", Med. Chem. Res., vol. 8, No. 9, pp. 523–541, 1998.
A. Matsuhisa et al., "Nonpeptide Arginine Vasopressin Antagonists for Both $V_{1A}$ and $V_2$ Receptors: Synthesis and Pharmacological Properties of 2–Phenyl–4'–[(2,3,4,5–tetrahydro–1H–1–benzazepin–1–yl)carbonyl]benzanilide Derivatives", Chemical Pharmaceutical Bulletin, vol. 45, No. 11, pp. 1870–1874, 1997.
E. Langhals et al., "Eine Einfache Neue Synthese der Fusarinsaure und anderer 5–Alkyl–2–pyridincarbonsauren", Liebigs Ann. Chem., pp. 930–949, 1982.

* cited by examiner

Primary Examiner—Richard L. Raymond
(74) Attorney, Agent, or Firm—Wenderoth, Lind & Ponack, L.L.P.

(57) ABSTRACT

A compound of the formula:

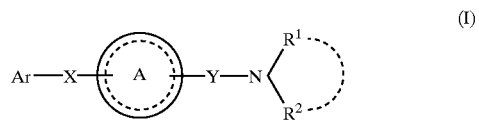

wherein Ar is an aromatic group; X and Y are a bivalent group selected from —O—, —S—, —CO—, —SO$_2$—, —NR$^8$—, —CONR$^8$—, SO$_2$NR$^8$ and —COO— (wherein R$^8$ is H, a hydrocarbon group or acyl), or a bivalent C$_{1-6}$ aliphatic hydrocarbon group which may contain one or two above bivalent groups; R$^1$ and R$^2$ are H or C$_{1-6}$ alkyl, or R$^1$ and R$^2$ may form, together with the adjacent nitrogen atom, a nitrogen-containing heterocyclic ring; and ring A is a monocyclic aromatic ring, or a salt thereof or a prodrug thereof exhibits an excellent inhibitory activity of the production and/or the secretion of amyloid-β protein.

26 Claims, No Drawings

β-AMYLOID PROTEIN PRODUCTION/SECRETION INHIBITORS

This application is a 371 of PCT/JP99/06450, filed Nov. 16, 1999.

TECHNICAL FIELD

The present invention relates to a novel amine derivative having an excellent inhibiting effect for the production and/or secretion of amyloid-β protein and production thereof.

BACKGROUND ART

Alzheimer's disease is a neurodegenerative disease, which is characterized by the degeneration and loss of neuronal cells accompanied by the formation of senile plaques and neurofibrillary tangles. Senile plaques that are the most characteristic in Alzheimer's disease consist of essentially amyloid-β protein (hereinafter, sometimes, abbreviated to Aβ) [see Biochem. Biophys. Res. Commun., 122, 1311 (1984)] and other intracerebral components. It is known that Aβ is composed of 40 or 42 amino acids (hereinafter abbreviated to $A\beta_{1-40}$ and $A\beta_{1-42}$, respectively) and is toxic to neurons and induces neurofibrillary changes.

Some patients with familial Alzheimer's disease are known to have APP (Amyloid Precursor Protein) gene mutation, and it is well known that the cells transfected with such mutated gene produce and secrete an increased amount of Aβ [for example, see Nature, 360, 672 (1992); Science, 259, 514 (1993); Science, 264, 1336 (1994), etc.].

Based on this information, medicines which inhibit the production and/or secretion of Aβ are useful for preventing and/or treating diseases caused by Aβ (e.g., Alzheimer's disease, Down's syndrome, etc).

In particular, for patients who are highly susceptible to the diseases, hereditarily, such as patients with familial Alzheimer's disease, etc., medicines which inhibit production and/or secretion of Aβ are especially useful for the prevention of such diseases.

On the other hand, the secreted form of APP is reported to have a neurotrophic factor like property (Neuron, 10, 243–254,1993). Example of neurotrophic factor like properties are given as, 1) survival and preserving effect to the neuronal cell; 2) stimulating the synapse formation; 3) protection of neuronal cell death; and 4) long term potentiation in hippocampus. By the above-mentioned properties, drugs which stimulate the secretion of the secreted form of APP are also useful in preventing and treating 1) neurodegenerative diseases (e.g., Alzheimer's disease, Down's syndrome, senile dementia, Parkinson's disease, Creutzfeldt-Jacob disease, amyotrophic sclerosis on lateral fasciculus, diabetic neuropathy, Huntington's disease, multiple sclerosis, etc.), 2) neurological disorders involved in cerebrovascular disorders (e.g., cerebral infarction, encephalorrhagia, etc.), a head injury or an injury of spinal cord, and so forth.

EP-A-652009 discloses peptide derivatives which are protease inhibitors exhibiting an Aβ production inhibiting effect in in vitro experiments using cell lines.

JP-A-2-91052 discloses a cholinesterase inhibitor comprising a substituted amine of the formula:

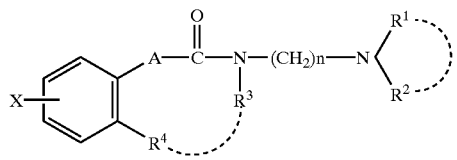

wherein $R^1$ and $R^2$ are independently hydrogen atom or a hydrocarbon group which may be substituted, or they form, together with the adjacent nitrogen atom, a fused heterocyclic group; $R^3$ and $R^4$ are such that, when $R^3$ is hydrogen atom, or a hydrocarbon group or an acyl group each or which may have substituent(s), $R^4$ is hydrogen atom, or $R^3$ and $R^4$ are bound to each other to form —$(CH_2)_m$—CO—, —CO—$(CH_2)_m$— or —$(CH_2)_{m+1}$— (wherein m is 0, 1 or 2); A is —$(CH_2)_l$—(wherein l is 0, 1 or 2) or —CH═CH—; X is one or more substituents and n is an integer of 4 to 7, or a salt thereof.

JP-A-2-73069 discloses a thiazole derivative having monoamine oxidase inhibitory activity.

WO98/38156 discloses a compound having a fused ring skeleton of a benzene ring and a 4- to 8-membered ring and having an inhibitory activity for the production and/or secretion of amyloid-β protein.

JP-A-5-239005 discloses N—(2-aminoethyl)benzamides useful for the treatment of senile dementia. However, this does not disclose an inhibitory activity of production and/or secretion of amyloid-β protein.

WO95/17183 discloses a compound having a phospholipase $A_2$ inhibitory activity and utility for treating senile dementia, etc. However, this does not disclose an inhibitory activity for the production and/or secretion of amyloid-β protein.

WO98/06691 discloses amine derivatives having an inhibitory activity of aggregation and/or accumulation of amyloid-β protein and useful for preventing and treating Alzheimer's disease. However, this does not disclose an inhibitory activity for the production and/or secretion of amyloid-β protein.

WO91/19697 discloses pyridine derivatives having angiotensin II antagonistic activity.

JP-A-3-142277 discloses amine compounds to be used for recording materials.

WO93/23040 discloses 17-ether and thioether of 4-azasteroid having 5α-reductase inhibitory activity.

It is desired to develop a compound which is different from the above known compounds in its chemical structure and which has an excellent inhibitory activity for the Aβ production and/or secretion and is therefore satisfactorily used in medicines.

DISCLOSURE OF INVENTION

The present inventors have studied various compounds having an inhibitory activity for the Aβ production and/or secretion and, as a result, have found that a compound of the formula:

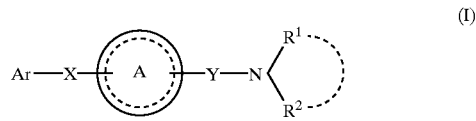

(I)

wherein Ar represents an aromatic group which may be substituted; X and Y are the same or different and each is a bivalent group selected from —O—, —S—, —CO—, —SO—, —SO$_2$—, —NR$^8$—, —CONR$^8$—, SO$_2$NR$^8$ and —COO— (wherein R$^8$ is hydrogen atom, a hydrocarbon group which may be substituted or acyl), or a bivalent C$_{1-6}$ aliphatic hydrocarbon group which may contain one or two above bivalent groups; R$^1$ and R$^2$ are hydrogen atom or C$_{1-6}$ alkyl which may be substituted, or R$^1$ and R$^2$ may form, together with the adjacent nitrogen atom, a nitrogen-containing heterocyclic ring which may be substituted; and ring A is a monocyclic aromatic ring which may be further substituted, or a salt thereof has an unexpected excellent inhibitory activity for the production and/or secretion of amyloid-β protein. On the basis of this finding, the present inventors have further studied and completed the present invention.

That is, the present invention provides:

1. An amyloid-β protein production and/or secretion inhibitor which comprises a compound of the formula:

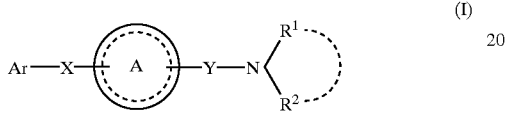

(I)

wherein Ar is an aromatic group which may be substituted; X and Y are the same or different and each is a bivalent group selected from —O—, —S—, —CO—, —SO—, —SO$_2$—, —NR$^8$—, —CONR$^8$—, SO$_2$NR$^8$ and —COO— (wherein R$^8$ is hydrogen atom, a hydrocarbon group which may be substituted or acyl), or a bivalent C$_{1-6}$ aliphatic hydrocarbon group which may contain one or two above bivalent groups; R$^1$ and R$^2$ are hydrogen atom or C$_{1-6}$ alkyl which may be substituted, or R$^1$ and R$^2$ may form, together with the adjacent nitrogen atom, a nitrogen-containing heterocyclic ring which may be substituted; and ring A is a monocyclic aromatic ring which may be further substituted, or a salt thereof;

2. The inhibitor according to the above 1, wherein Ar is:

(1) a monovalent monocyclic aromatic group formed by removing any one of hydrogen atoms from a benzene ring or a 5- or 6-membered aromatic heterocyclic ring having, in addition to carbon atom, 1 to 3 hetero atoms selected from nitrogen atom, sulfur atom and oxygen atom, (2) an aromatic ring assembly group formed by removing any one of hydrogen atoms from an aromatic ring assembly of 2 or 3 rings of [1] C$_{6-14}$ monocyclic or bi- or tricyclic aromatic hydrocarbon aromatic ring or [2] 5- to 14-membered aromatic heterocyclic ring having, in addition to carbon atom, 1 to 4 hetero atoms selected from nitrogen atom, sulfur atom and oxygen atom, or rings formed by the aromatic heterocyclic ring fused together with 1 or 2 benzene rings, said rings being bound to each other directly through a single bond, and the number of the bonds which bind the rings directly being smaller than the number of the rings by 1, or (3) a monovalent fused aromatic group formed by removing any one of hydrogen atoms from [1] C$_{9-14}$ bi- or tricyclic aromatic hydrocarbon or [2] a 9- to 14-membered fused polycyclic aromatic ring having, in addition to carbon atom, 1 to 4 hetero atoms selected from nitrogen atom, sulfur atom and oxygen atom, which may be substituted with 1 to 5 substituents selected from the group consisting of (i) halogen atom, (ii) C$_{1-3}$ alkylenedioxy, (iii) nitro, (iv) cyano, (v) C$_{1-6}$ alkyl which may be halogenated, (vi) C$_{6-10}$ aryloxy-C$_{1-6}$ alkyl, (vii) C$_{1-6}$ alkyl-C$_{6-10}$ aryl-C$_{2-6}$ alkenyl, (viii) C$_{3-6}$ cycloalkyl which may be halogenated, (ix) C$_{7-16}$ aralkyl which may be substituted with 1 to 5 substituents selected from the group consisting of (a) halogen atom, (b) C$_{1-3}$ alkylenedioxy, (c) nitro, (d) cyano, (e) C$_{1-6}$ alkyl which may be halogenated, (f) C$_{3-6}$ cycloalkyl which may be halogenated, (g) C$_{1-6}$ alkoxy which may be halogenated, (h) C$_{1-6}$ alkylthio which may be halogenated, (i) hydroxy, (j) amino, (k) mono-C$_{1-6}$ alkylamino, (l) di-C$_{1-6}$ alkylamino, (m) formyl, (n) carboxy, (o) carbamoyl, (p) C$_{1-6}$ alkyl-carbonyl which may be halogenated, (q) C$_{1-6}$ alkoxy-carbonyl, (r) mono-C$_{1-6}$ alkyl-carbamoyl, (s) di-C$_{1-6}$ alkyl-carbamoyl, (t) C$_{1-6}$ alkylsulfonyl which may be halogenated, (u) formylamino, (v) C$_{1-6}$ alkyl-carboxamido which may be halogenated, (w) C$_{1-6}$ alkoxy-carboxamido, (x) C$_{1-6}$ alkylsulfonylamino, (y) C$_{1-6}$ alkyl-carbonyloxy, (z) C$_{1-6}$ alkoxy-carbonyloxy, (aa) mono-C$_{1-6}$ alkyl-carbamoyloxy and (bb) di-C$_{1-8}$ alkyl-carbamoyloxy, (x) C$_{1-6}$ alkoxy which may be halogenated, (xi) C$_{1-6}$ alkylthio which may be halogenated, (xii) hydroxy, (xiii) C$_{6-10}$ aryloxy which may be substituted with 1 to 5 substituents selected from the group consisting of (a) halogen atom, (b) C$_{1-3}$ alkylenedioxy, (c) nitro, (d) cyano, (e) C$_{1-6}$ alkyl which may be halogenated, (f) C$_{3-6}$ cycloalkyl which may be halogenated, (g) C$_{1-6}$ alkoxy which may be halogenated, (h) C$_{1-6}$ alkylthio which may be halogenated, (i) hydroxy, (j) amino, (k) mono-C$_{1-6}$ alkylamino, (l) di-C$_{1-6}$ alkylamino, (m) formyl, (n) carboxy, (o) carbamoyl, (p) C$_{1-6}$ alkyl-carbonyl which may be halogenated, (q) C$_{1-6}$ alkoxy-carbonyl, (r) mono-C$_{1-6}$ alkyl-carbamoyl, (s) di-C$_{1-6}$ alkyl-carbamoyl, (t) C$_{1-6}$ alkylsulfonyl which may be halogenated, (u) formylamino, (v) C$_{1-6}$ alkyl-carboxamido which may be halogenated, (w) C$_{1-6}$ alkoxy-carboxamido, (x) C$_{1-6}$ alkylsulfonylamino, (y) C$_{1-6}$ alkyl-carbonyloxy, (z) C$_{1-6}$ alkoxy-carbonyloxy, (aa) mono-C$_{1-6}$ alkyl-carbamoyloxy and (bb) di-C$_{1-8}$ alkyl-carbamoyloxy, (xiv) C$_{6-10}$ aryl-C$_{7-16}$ aralkyloxy, (xv) amino, (xvi) mono-C$_{1-6}$ alkylamino, (xvii) di-C$_{1-6}$ alkylamino, (xviii) 5- to 7-membered saturated cyclic amino which may be substituted with 1 to 3 substituents selected from the group consisting of [1] C$_{6-14}$ aryl which may be substituted with 1 to 5 substituents selected from the group consisting of (a) C$_{1-6}$ alkyl which may be halogenated (b) halogen atom, (c) C$_{1-3}$ alkylenedioxy, (d) nitro, (e) cyano, (f) C$_{3-6}$ cycloalkyl which may be halogenated, (g) C$_{1-6}$ alkoxy which may be halogenated, (h) C$_{1-6}$ alkylthio which may be halogenated, (i) hydroxy, (j) amino, (k) mono-C$_{1-6}$ alkylamino, (l) di-C$_{1-6}$ alkylamino, (m) formyl, (n) carboxy, (o) carbamoyl, (p) C$_{1-6}$ alkyl-carbonyl which may be halogenated, (q) C$_{1-6}$ alkoxy-carbonyl, (r) mono-C$_{1-6}$ alkyl-carbamoyl, (s) di-C$_{1-6}$ alkyl-carbamoyl, (t) C$_{1-6}$ alkylsulfonyl which may be halogenated, (u) formylamino, (v) C$_{1-6}$ alkyl-carboxamido which may be halogenated, (w) C$_{1-6}$ alkoxy-carboxamido, (x) C$_{1-6}$ alkylsulfonylamino, (y) C$_{1-6}$ alkyl-carbonyloxy, (z) C$_{1-6}$ alkoxy-carbonyloxy, (aa) mono-C$_{1-6}$ alkyl-carbamoyloxy and (bb) di-C$_{1-8}$ alkyl-carbamoyloxy, [2] C$_{7-9}$ aralkyl which may be substituted with 1 to 5 substituents selected from the group consisting of (a) C$_{1-6}$ alkyl which may be halogenated (b) halogen atom, (c) C$_{1-3}$ alkylenedioxy, (d) nitro, (e) cyano, (f) C$_{3-6}$ cycloalkyl which may be halogenated, (g) C$_{1-6}$ alkoxy which may be halogenated, (h) C$_{1-6}$ alkylthio which may be halogenated, (i) hydroxy, (j) amino, (k) mono-C$_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{6-10}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{16}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xix) acyl represented by the formula: —CO—$R^3$, —CO—$OR^3$, —CO—$NR^3R^4$, —CS—$NHR^3$, —$SO_2$—$R^{3a}$ or —SO—$R^{3a}$ [wherein $R^3$ is hydrogen atom, or $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkylcarbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^{3a}$ is $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p)

$C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv). $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^4$ is hydrogen atom or $C_{1-6}$ alkyl, or $R^3$ and $R^4$ may form, together with the adjacent nitrogen atom, 5- to 7-membered nitrogen-containing heterocyclic ring having, in addition to carbon atom, at least one nitrogen atom, which may further have 1 to 3 hetero atoms selected from nitrogen atom, sulfur atom and oxygen atom], (xx) acylamino represented by the formula: —$NR^5$—$COR^6$, —$NR^5$—$COOR^{6a}$, —$NR^5$—$SO_2RR^{6a}$ or —$NR^5$—$CONR^{6a}R^{6b}$ [wherein $R^5$ is hydrogen atom or $C_{1-6}$ alkyl, $R^6$ is as defined above $R^3$, $R^{6a}$ is as defined above $R^{3a}$, $R^{6b}$ is as defined above $R^4$] and (xxi) acyloxy represented by the formula: —O—$COR^7$, —O—$COOR^7$ or —O—$CONHR^7$ [wherein $R^7$ is as defined above $R^3$], X and Y are the same and different and each is a bivalent group selected from —O—, —S—, —CO—, —SO—, —$SO_2$—, —$NR_8$—, —$CONR^8$—, —$SO_2NR^8$— and —COO— [wherein $R^8$ is (1) hydrogen atom, (2) $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{3-6}$ aryl or $C_{7-19}$ aralkyl, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated (ix) hydroxy, (x) amino, (xiii) [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, (3) acyl represented by the formula: —CO—$R^3$, —CO—$OR^3$, —CO—$NR^3R^4$, —CS—$NHR^3$, —$SO_2$—$R^{3a}$ or —SO—$R^{3a}$

[wherein $R^3$ is hydrogen atom, or $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_6$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^{3a}$ is $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^4$ is hydrogen atom or $C_{1-6}$ alkyl, or $R^3$ and $R^4$ may form, together with the adjacent nitrogen atom, 5- to 7-membered nitrogen-containing heterocyclic ring having, in addition to carbon atom, at least one nitrogen atom, which may further have 1 to 3 hetero atoms selected from nitrogen atom, sulfur atom and oxygen atom], or $C_{1-6}$ alkylene, $C_{2-6}$ alkenylene or $C_{2-6}$ alkynylene which may contain one or two these bivalent groups, $R^1$ and $R^2$ are (1) hydrogen atom, (2) $C_{1-6}$ alkyl which may substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) formyl, (xiv) carboxy, (xv) carbamoyl, (xvi) $C_{1-6}$ alkyl-carbonyl which may be halogenated, (xvii) $C_{1-6}$ alkoxy-carbonyl, (xviii) mono-$C_{1-6}$ alkyl-carbamoyl, (xix) di-$C_{1-6}$ alkyl-carbamoyl, (xx) $C_{1-6}$ alkylsulfonyl which may be halogenated, (xxi) formylamino, (xxii) $C_{1-6}$ alkyl-carboxamido which may be halogenated, (xxiii) $C_{1-6}$ alkoxy-carboxamido, (xxiv) $C_{1-6}$ alkylsulfonylamino, (xxv) $C_{1-6}$ alkyl-carbonyloxy, (xxvi) $C_{1-6}$ alkoxy-carbonyloxy, (xxvii) mono-$C_{1-6}$ alkyl-carbamoyloxy, (xxviii) di-$C_{1-6}$ alkyl-carbamoyloxy, and (xxix) the same group as that of Ar, or $R^1$ and $R^2$ may form, together with the adjacent nitrogen atom, 3- to 8-membered nitrogen-containing heterocyclic ring having, in addition to carbon atom, at least one nitrogen atom, which may further have 1 to 3 hetero atoms selected from nitrogen, sulfur atom and oxygen atom, and which may be substituted with 1 to 3 substituents selected from the group consisting of (i) $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (ii) $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iii) 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iv) $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (v) $C_{1-6}$ alkyl-carbonyl which may be halogenated, and (vi) $C_{1-6}$ alkyl-sulfonyl, and ring A is a benzene ring, or a 5- or 6-membered aromatic heterocyclic ring which may be substituted with 1 to 3 substituents selected from the group consisting of halogen atom, $C_{1-6}$ alkyl which may be halogenated, $C_{1-6}$ alkoxy which may be halogenated, hydroxy and amino, in addition to the substituent represented by Ar—X—;

3. The inhibitor according to the above 1, wherein the aromatic group represented by Ar is a monocyclc aromatic group, an aromatic ring assembly group or a fused aromatic group;

4. The inhibitor according to the above 1, wherein Ar is an aromatic ring assembly group which may be substituted;

5. The inhibitor according to the above 4, wherein the aromatic ring assembly group is 2-, 3- or 4-biphenylyl;

6. The inhibitor according to the above 1, wherein Ar is phenyl, biphenylyl or naphthyl group which may be substituted with halogen atom;

7. The inhibitor according to the above 1, wherein X is [1] a group represented by the formula: —$(CH_2)_{p1}$O— (wherein $p^1$ is an integer of 1 to 3), [2] —$(CH_2)_{p2}$— (wherein $p^2$ is an integer of 1 to 3), [3] $(CH_2)_{p3}$OCONH— (wherein $p^3$ is an integer of 1 to 3), [4] CONH or [5] $SO_2NH$;

8. The inhibitor according to the above 1, wherein X is a group represented by the formula: —$(CH_2)_{p1}$O— (wherein $p^1$ is an integer or 1 to 3);

9. The inhibitor according to the above 1, wherein the bivalent $C_{1-6}$ aliphatic hydrocarbon group of Y is a bivalent $C_{1-3}$ aliphatic hydrocarbon group;

10. The inhibitor according to the above 1, wherein Y is [1] a group represented by the formula: —$(CH_2)_{q1}$CONR$^9$$(CH_2)_{r1}$— (wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated); or [2] a group represented by the formula: —$(CH_2)_{q2}$COO$(CH_2)_{r2}$— (wherein each of $q^2$ and $r^2$ is an integer of 0 to 3 and their sum is not more than 3);

11. The inhibitor according to the above 1, wherein Y is a group represented by the formula: —$(CH_2)_{q1}$CONR$^9$$(CH_2)_{r1}$— (wherein each of $q^1$ and $r^1$ is an integer of 0 to 3 and their sum is an integer of not more than 3, $R^9$ is hydrogen atom or $C_{1-6}$ alkyl-carbonyl);

12. The inhibitor according to the above 1, wherein each of $R^1$ and $R^2$ is [1] hydrogen atom or [2] $C_{1-6}$ alkyl which may be substituted with carboxyl or $C_{1-6}$ alkoxy-carbonyl, or $R^1$ and $R^2$ form, together with the adjacent nitrogen atom, a 5- or 6-membered nitrogen-containing heterocyclic ring;

13. The inhibitor according to the above 1, wherein ring A is a benzene ring or a 6-membered nitrogen-containing heterocyclic ring which may be substituted with halogen atom or $C_{1-6}$ alkoxy;

14. The inhibitor according to the above 1, wherein ring A is a benzene ring, a pyridine ring or 2-pyridone ring;

15. The inhibitor according to the above 1, wherein ring A is a benzene ring or a pyridine ring;

16. The inhibitor according to the above 1, wherein Ar is $C_{6-14}$ aryl or biphenylyl which may be substituted with halogen atom, X is [1] a group represented by the formula: —$(CH_2)_{p1}$O— (wherein $p^1$ is an integer of 1 to 3), [2] —$(CH_2)_{p2}$— (wherein $p^2$ is an integer of 1 to 3), [3] $(CH_2)_{p3}$OCONH— (wherein $p^3$ is an integer of 1 to 3), [4] CONH or [5] $SO_2NH$, Y is [1] a group represented by the formula: —$(CH_2)_{q1}$CONR$^9$$(CH_2)_{r1}$— (wherein each of $q^1$ and $r^1$ is an integer of 0 to 3 and their sum is an integer of not more than 3, $R^9$ is hydrogen atom or $C_{1-6}$ alkyl-carbonyl which may be halogenated), or [2] a group represented by the formula: —$(CH_2)_{q2}$COO$(CH_2)_{r2}$— (wherein each of $q^2$ and $r^2$ is an integer of 0 to 3 and their sum is not more than 3), each of $R^1$ and $R^2$ is [1] hydrogen atom or [2] $C_{1-6}$ alkyl which may be substituted with carboxy, $C_{1-6}$ alkoxy-carbonyl, or di-$C_{1-6}$ alkylnitrile, or $R^1$ and $R^2$ form, together with the adjacent nitrogen atom, a 5- or 6-membered nitrogen-containing heterocyclic ring, and ring A is a benzene ring or a 6-membered nitrogen-containing heterocyclic ring which may be substituted with halogen atom or $C_{1-6}$ alkoxy;

17. The inhibitor according to the above 1, wherein Ar is $C_{6-14}$ aryl or biphenylyl which may be substituted with halogen atom, X is a group represented by the formula: —$(CH_2)_{p1}O$— (wherein $p^1$ is an integer of 1 to 3), CONH or $SO_2NH$, Y is $C_{1-3}$ alkylene, —CONH$(CH_2)_s$— (wherein s is an integer of 1 to 3) or —COO$(CH_2)_t$— (wherein t is an integer of 1 to 3), each of $R^1$ and $R^2$ is hydrogen atom or $C_{1-6}$ alkyl, or $R^1$ and $R^2$ form, together with the adjacent nitrogen atom, a 5- or 6-membered nitrogen-containing heterocyclic ring, and ring A is a benzene ring or a 6-membered nitrogen-containing heterocyclic ring which may be substituted with halogen atom or $C_{1-6}$ alkoxy.

18. The inhibitor according to the above 1, wherein the compound is 5-chloro-N-[2-N,N-diethylamino)ethyl]-2-methoxy-4-(1-naphthoylamino)benzamide,
5-chloro-N-[2-N,N-diethylamino)ethyl]-2-methoxy-4-(2naphthoylamino)benzamide,
5-chloro-N-[2-N,N-diethylamino)ethyl]-2-methoxy-4-(1-naphthylsulfonylamino)benzamide,
5-chloro-N-[2-N,N-diethylamino)ethyl]-2-methoxy-4-(2-naphthylsulfonylamino)benzamide,
N-[3-[4-(2-naphthylmethoxy)phenyl]propyl]-N,N-dipropylamine hydrochloride,
N-[3-[4-[(2,4-dichlorobenzyl)oxy]phenyl]propyl]-N,N-dipropylamine hydrochloride,
N-[4-(2-naphthylmethoxy)phenethyl]-N,N-dipropylamine hydrochloride,
N-[4-(2,4-dichlorobenzyl)oxy]phenethyl]-N,N-dipropylamine hydrochloride,
N-[4-(4-biphenylylmethoxy)phenethyl]-N,N-dipropylamine hydrochloride,
N-[2-(2-naphthylmethoxy)phenethyl]-N,N-dipropylamine hydrochloride,
N-[3-(2-naphthylmethoxy)phenethyl]-N,N-dipropylamine hydrochloride,
N-[3-(4-biphenylylmethoxy)phenethyl]-N,N-dipropylamine hydrochloride,
N-[3-[(2,4-dichlorobenzyl)oxy]phenethyl]-N,N-dipropylamine hydrochloride,
N-[3-(1-naphthylmethoxy)phenethyl]-N,N-dipropylamine hydrochloride,
4-(4-biphenylylmethoxy)phenyl-N-(2-piperidinoethyl) acetamide,
4-(4-biphenylylmethoxy)phenyl-N-[2-(N,N-dimethylamino)ethyl]acetamide,
6-(4-biphenylylmethoxy)-N-[2-(pyrrolidine-1-yl)ethyl] nicotinamide,
1-(4-biphenylylmethyl)-1,6-dihydro-6-oxo-N-[2-(pyrrolidine-1-yl)ethyl]-3-pyridinecarboxamide,
1-(4-biphenylylmethyl)-1,6-dihydro-6-oxo-N-(2-(piperidinoethyl)-3-pyridinecarboxamide,
6-(4-biphenylylmethoxy)-N-(2-piperidinoethyl) nicotinamide,
6-(4-biphenylylmethoxy)-N-[2-(N,N-dimethylamino)ethyl] nicotinamide,
4-(4-biphenylylmethoxy)-N-(2-piperidinoethyl)benzamide,
4-(4-biphenylylmethoxy)-N-[(2-pyrrolidine-1-yl)ethyl] benzamide,
2-piperidinoethyl=4-(4-biphenylylethoxy)benzoate,
2-(pyrrolidin-1-yl)ethyl=4-(4-biphenylylmethoxy)benzoate,
4-[4-(biphenylylmethoxy)phenyl]-N-[2-(N,N-dimethylamino)ethyl]acetamide oxalate,
4-[4-(biphenylylmethoxy)phenyl]-N-[2-(N,N-dimethylamino)ethyl]acetamide maleate,
4-[4-(biphenylylmethoxy)phenyl]-N-[2-(N,N-dimethylamino)ethyl]acetamide fumarate,
4-[4-(biphenylylmethoxy)phenyl]-N-[2-(N-methylamino) ethyl]acetamide hydrochloride, ethyl]acetamide hydrochloride,
4-[4-(biphenylylmethoxy)phenyl]-N-[2-(N-methylamino) ethyl]acetamide,
ethyl 7-[2-[4-[(4-biphenylylmethoxy)phenyl] acetylaminoethyl](methyl)amino]heptanoate,
7-[2-[4-[4-(biphenylylmethoxy)phenyl]acetylaminoethyl] (methyl)amino]heptanoic acid hydrochloride,
N-(4-(2-((2-(dimethylamino)ethyl)(methyl)amino)-2-oxoethyl)phenyl)[1,1'-biphenyl]-4-carboxamido,
N-(2-aminoethyl)-2-(4-([1,1'-biphenyl]-4-ylmethoxy) phenyl)acetamide hydrochloride,
4-([1,1'-biphenyl]-4-ylmethoxy)-N-(2-(1-pyrrolidinyl) ethyl)benzamide,
N-(4-(2-((2-dimethylamino)ethyl)(methyl)amino)-2-oxoethyl)phenyl)[1,1'-biphenyl]-4-carboxamide,
N-[4-({[2-(diethylamino)ethyl]amino}carbonyl)phenyl](4-biphenylyl)carboxamide,
4-(4-biphenylyl)methoxy)-N-[2-(isopropylamino)ethyl] benzamide,
2-(N,N-diethylamino)ethyl-4-[(4-biphenylyl)carbonyl] amino]benzoate,
N-[4-({[2-(dimethylamino)ethyl]amino}carbonyl)phenyl] (4-biphenylyl)carboxamide,
N-[4-{[2-(piperidinoethyl)amino]carbonyl}phenyl](4-biphenylyl)carboxamide, or
N-[4-({[2-(pyrrolidinyl)ethyl]amino}carbonyl)phenyl](4-biphenylyl)carboxamide;

19. The inhibitor according to the above 1 which is an agent for preventing or treating diseases caused by the production and/or secretion of amyloid-β protein;

20. The inhibitor according to the above 1 which is an agent for preventing or treating senile dementia, Alzheimer's disease, Down's syndrome, Parkinson's disease, disease, amyloid angiopathy or disorders due to amyloid-β protein in cerebrovascular disorders caused by the production and/or secretion of amyloid-β protein;

21. A compound represented by the formula:

$$Ar'—X'—\underset{A}{\bigcirc}—Y'—N\begin{pmatrix}R^1\\R^2\end{pmatrix} \quad (Ia)$$

wherein
Ar' is an aromatic ring assembly group which may be substituted,
X' is [1] a group represented by the formula: —$(CH_2)_{p1}$O— (wherein $p^1$ is an integer of 1 to 3), [2] —$(CH_2)_{p2}$— (wherein $p^2$ is an integer of 1 to 3) or [3] CONH,
Y' is [1] a group represented by the formula: —$(CH_2)_{q1}$CONR$^9$(CH$_2$)$_{r1}$— (wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated):, or [2] a group represented by the formula: —$(CH_2)_{q2}$COO$(CH_2)_{r2}$— (wherein each of $q^2$ and $r^2$ is an integer of 0 to 3 and their sum is not more than 3), each of $R^1$ and $R^2$ is hydrogen atom or $C_{1-6}$ alkyl which may be substituted, or $R^1$ and $R^2$ may form, together with the adjacent nitrogen atom, a nitrogen-containing heterocyclic ring, and ring A is a monocyclic aromatic ring which may be further substituted;

22. The compound according to the above 21, wherein Ar' is:

an aromatic ring assembly group formed by removing any one of hydrogen atoms from an aromatic ring assembly of 2 or 3 rings of [1] $C_{6-14}$ monocyclic or bi- or tricyclic aromatic hydrocarbon aromatic ring or [2] 5- to 14-membered aromatic heterocyclic ring having, in addition to carbon atom, 1 to 4 hetero atoms selected from nitrogen atom, sulfur atom and oxygen atom, or rings formed by the aromatic heterocyclic ring fused together with 1 or 2 benzene rings, said rings being bound to each other directly through a single bond, and the number of the bonds which bind the rings directly being smaller than the number of the rings by 1, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{6-10}$ aryloxy-$C_{1-6}$ alkyl, (vii) $C_{1-6}$ alkyl-$C_{6-10}$ aryl-$C_{2-6}$ alkenyl, (viii) $C_{3-6}$ cycloalkyl which may be halogenated, (ix) $C_{7-16}$ aralkyl which may be substituted with 1 to 5 substituents selected from the group consisting of (a) halogen atom, (b) $C_{1-3}$ alkylenedioxy, (c) nitro, (d) cyano, (e) $C_{1-6}$ alkyl which may be halogenated, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (x) $C_{1-6}$ alkoxy which may be halogenated, (xi) $C_{1-6}$ alkylthio which may be halogenated, (xii) hydroxy, (xiii) $C_{6-10}$ aryloxy which may be substituted with 1 to 5 substituents selected from the group consisting of (a) halogen atom, (b) $C_{1-3}$ alkylenedioxy, (c) nitro, (d) cyano, (e) $C_{1-6}$ alkyl which may be halogenated, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (xiv) $C_{6-10}$ aryl-$C_{7-16}$ aralkyloxy, (xv) amino, (xvi) mono-$C_{1-6}$ alkylamino, (xvii) di-$C_{1-6}$ alkylamino, (xviii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_8$ alkyl-carbamoyloxy, [5] $C_{1-6}$ alkyl-carbonyl which may be halogenated, and [6] $C_{1-6}$ alkyl-sulfonyl, (xix) acyl represented by the formula: —CO—$R^3$, —CO—$OR_3$, —CO—$NR^3R^4$, —CS—$NHR^3$, —$SO_2$—$R^{3a}$ or —SO—$R^{3a}$ [wherein $R^3$ is hydrogen atom, or $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-9}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ g aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k), mono-$C_{1-6}$ alkylamino, (1) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (1) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^{3a}$ is $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv)

cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{1-6}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^4$ is hydrogen atom or $C_{1-6}$ alkyl, or $R^3$ and $R^4$ may form, together with the adjacent nitrogen atom, 5- to 7-membered nitrogen-containing heterocyclic ring having, in addition to carbon atom, at least one nitrogen atom, which may further have 1 to 3 hetero atoms selected from nitrogen atom, sulfur atom and oxygen atom], (xx) acylamino represented by the formula: —$NR^5$—$COR^6$, —$NR^5$—$COOR^{6a}$, —$NR^5$—$SO_2RR^{6a}$ or —$NR^5$—$CONR^{6a}R^{6b}$ [wherein $R^5$ is hydrogen atom or $C_{1-6}$ alkyl, $R^6$ is as defined above $R^3$, $R^{6a}$ is as defined above $R^{3a}$, $R^{6b}$ is as defined above $R^4$] and (xxi) acyloxy represented by the formula: —O—$COR^7$, —O—$COOR^7$ or —O—$CONHR^7$ [wherein $R^7$ is as defined above $R^3$], $R^1$ and $R^2$ are (1) hydrogen atom, (2) $C_{1-6}$ alkyl which may substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) formyl, (xiv) carboxy, (xv) carbamoyl, (xvi) $C_{1-6}$ alkyl-carbonyl which may be halogenated, (xvii) $C_{1-6}$ alkoxy-carbonyl, (xviii) mono-$C_{1-6}$ alkyl-carbamoyl, (xix) di-$C_{1-6}$ alkyl-carbamoyl, (xx) $C_{1-6}$ alkylsulfonyl which may be halogenated, (xxi) formylamino, (xxii) $C_{1-6}$ alkyl-carboxamido which may be halogenated, (xxiii) $C_{1-6}$ alkoxy-carboxamido, (xxiv) $C_{1-6}$ alkylsulfonylamino, (xxv) $C_{1-6}$ alkyl-carbonyloxy, (xxvi) $C_{1-6}$ alkoxy-carbonyloxy, (xxvii) mono-$C_{1-6}$ alkyl-carbamoyloxy, (xxviii) di-$C_{1-6}$ alkyl-carbamoyloxy, and (xxix) the same group as that of Ar, $R^1$ and $R^2$ may form, together with the adjacent nitrogen atom, 3- to 8-membered nitrogen containing heterocyclic ring having, in addition to carbon atom, at least one nitrogen atom, which may further have 1 to 3 hetero atoms selected from nitrogen, sulfur atom and oxygen atom and which may be substituted with 1 to 3 substituents selected from the group consisting of (i) $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (ii) $C_{7-9}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iii) 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iv) $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which, may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (v) $C_{1-6}$ alkyl-carbonyl which may be halogenated, and (vi) $C_{1-6}$ alkyl-sulfonyl, and ring A is a benzene ring, or a 5- or 6-membered aromatic heterocyclic ring which may be substituted with 1 to 3 substituents selected from the group consisting of halogen atom, $C_{1-6}$ alkyl which may be halogenated, $C_{1-6}$ alkoxy which may be halogenated, hydroxy and amino, in addition to the substituent represented by Ar—X—;

23. The compound according to the above 21, wherein the aromatic ring assembly group represented by Ar' is 2-, 3- or 4-biphenylyl;

24. The compound according to the above 21, wherein X' is a group represented by —$(CH_2)_{p1}$O— (wherein $p^1$ is an integer of 1 to 3);

25. The compound according to the above 21, wherein Y' is a group represented by the formula: —$(CH_2)_{q1}$CONR$^9$$(CH_2)_{r1}$— (wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated);

26. The compound according to the above 21, wherein each of $R^1$ and $R^2$ is [1] hydrogen atom or [2] $C_{1-6}$ alkyl which may be substituted with carboxy or $C_{1-6}$ alkoxy-carbonyl, or $R^1$ and $R^2$ form, together with the adjacent nitrogen atom, a 5- or 6-membered nitrogen-containing heterocyclic ring;

27. The compound according to the above 21, wherein ring A is a benzene ring or a 6-membered nitrogen-containing aromatic heterocyclic ring which may be substituted with halogen atom or $C_{1-6}$ alkoxy;

28. The compound according to the above 21, wherein ring A is a benzene ring, a pyridine ring or 2-pyridone ring;

29. The compound according to the above 21, wherein ring A is a benzene ring or a pyridine ring;

30. The compound according to the above 21, wherein Ar' is 2-, 3- or 4-biphenylyl, X' is [1] a group represented by the formula: —$(CH_2)_{p1}$O— (wherein $p^1$ is an integer of 1 to 3), [2] —$(CH_2)_{p2}$— (wherein $p^2$ is an integer of 1 to 3) or [3] CONH, Y' is [1] a group represented by the formula: —$(CH_2)_{q1}$CONR$^9$$(CH_2)_{r1}$— (wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated), or [2] a group represented by the formula: —$(CH_2)_{q2}$COO$(CH_2)_{r2}$— (wherein each of $q^2$ and $r^2$ is an integer of 0 to 3 and their sum is not more than 3), each of $R^1$ and $R^2$ is [1] hydrogen atom or [2] $C_{1-6}$ alkyl which may be substituted with carboxy, $C_{1-6}$ alkoxy-carbonyl or di-$C_{1-6}$ alkylnitrile, or $R^1$ and $R^2$ may form, together with the adjacent nitrogen atom, a 5- or 6-membered, nitrogen-containing heterocyclic ring, and ring A is a benzene ring or a 6-membered nitrogen-containing aromatic heterocyclic ring;

31. The compound according to the above 21, wherein Ar' is biphenylyl, X' is —$(CH_2)_{p1}O$— (wherein p1 is an integer of 1 to 3), Y' is —$CONH(CH_2)_s$— (wherein s is an integer of 1 to 3), $R^1$ and $R^2$ are $C_{1-6}$ alkyl, or $R^1$ and $R^2$ form, together with the adjacent nitrogen atom, a 5- or 6-membered nitrogen-containing heterocyclic ring, and ring A is a benzene ring or a 6-membered nitrogen-containing aromatic heterocyclic ring;

32. 4-(4-biphenylylmethoxy)phenyl-N-(2-piperidino-ethyl)acetamide,
4-(4-biphenylylmethoxy)phenyl-N-[2-(N,N-dimethylamino)-ethyl]acetamide,
6-(4-biphenylylmethoxy)-N-[2-(pyrrolidine-1-yl)ethyl]-nicotinamide,
1-(4-biphenylylmethyl)-1,6-dihydro-6-oxo-N-[2-(pyrrolidine-1-yl)ethyl]-3-pyridinecarboxamido,
1-(4-biphenylylmethyl)-1,6-dihydro-6-oxo-N-(2-(piperidinoethyl)-3-pyridinecarboxamido,
6-(4-biphenylylmethoxy)-N-(2-piperidinoethyl) nicotinamide,
6-(4-biphenylylmethoxy)-N-[2-(N,N-dimethylamino) ethyl]-nicotinamide,
4-(4-biphenylylmethoxy)-N-(2-piperidinoethyl)benzamide,
4-(4-biphenylylmethoxy)-N-[(2-pyrrolidine-1-yl)ethyl]-benzamide,
2-piperidinoethyl=4-(4-biphenylylethoxy)benzoate,
2-(pyrrolidin-1-yl)ethyl=4-(4-biphenylylmethoxy)benzoate,
4-[4-(biphenylylmethoxy)phenyl]-N-[2-(N,N-dimethylamino)-ethyl]acetamide oxalate,
4-[4-(biphenylylmethoxy)phenyl]-N-[2-(N,N-dimethylamino)-ethyl]acetamide maleate,
4-[4-(biphenylylmethoxy)phenyl]-N-[2-(N,N-dimethylamino)-ethyl]acetamide fumarate,
4-[4-(biphenylylmethoxy)phenyl]-N-[2-(N-methylamino)-ethyl]acetamide hydrochloride,
4-[4-(biphenylylmethoxy)phenyl]-N-[2-(N-methylamino)-ethyl]acetamide,
ethyl 7-[2-[4-[(4-biphenylylmethoxy)phenyl]acetylamino-ethyl](methyl)amino]heptanoate,
7-[2-[4-[4-(biphenylylmethoxy)phenyl]acetylaminoethyl]-methyl)amino]heptanoic acid hydrochloride,
N-(4-(2-((2-(dimethylamino)ethyl)(methyl)amino)-2-oxoethyl)phenyl)[1,1'-biphenyl]-4-carboxamide,
N-(2-aminoethyl)-2-(4-([1,1'-biphenyl]-4-ylmethoxy) phenyl)-acetamide hydrochloride,
4-([1,1,'-biphenyl]-4-ylmethoxy)-N-(2-(1-pyrrolidinyl)-ethyl)benzamide,
N-(4-((2-([2-dimethylamino)ethyl](methyl)amino)-2-oxoethyl)phenyl)[1,1'-biphenyl]-4-carboxamide,N-[4-({[2-(diethylamino)ethyl]amino}carbonyl)phenyl](4-biphenylyl)carboxamide,
4-(4-biphenylyl)methoxy)-N-[2-(isopropylamino)ethyl]-benzamide,
2-(N,N-diethylamino)ethyl-4-[(4-biphenylyl)carbonyl] amino]-benzoate,
N-[4-({[2-(dimethylamino)ethyl]amino}carbonyl)phenyl] (4-biphenylyl)carboxamide,
N-[4-{[2-(piperidinoethyl)amino]carbonyl}phenyl](4-biphenylyl)carboxamide, or
N-[4-({[2-(pyrrolidinyl)ethyl]amino}carbonyl)phenyl](4-biphenylyl)carboxamide;

33. A prodrug of the compound according to the above 21.

34. A process for producing the compound according to the above 21 which comprises:
(1) reacting a compound represented by the formula:

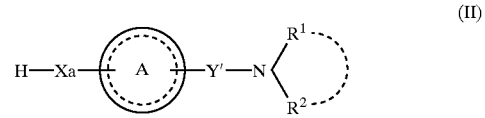

(II)

wherein Xa is oxygen atom, sulfur atom which may be oxidized or imino which may be substituted, and other symbols are as defined in the above 21, or a salt thereof with a compound represented by the formula:

Ar—Xb—L    (III)

wherein Xb is a group corresponding to X' from which Xa is removed, L is a leaving group of hydroxy, and X' and Ar' are as defined in the above 21, or a salt thereof, or (2) reacting a compound represented by the formula:

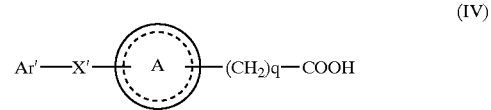

(IV)

wherein each symbol is as defined in the above 21, or a salt thereof with a compound represented by the formula:

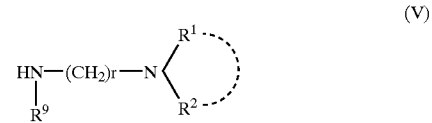

(V)

wherein each symbol is as defined in the above 21, or a salt thereof;

35. A pharmaceutical composition which comprises a compound represented by the formula:

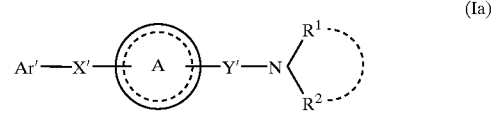

(Ia)

wherein Ar' is aromatic ring assembly group which may be substituted, X' is [1] a group represented by the formula: —$(CH_2)_{p^1}O$— (wherein $p^1$ is an integer of 1 to 3), [2] —$(CH_2)_{p2}$— (wherein $p_2$ is an integer of 1 to 3) or [3] CONH, Y' is [1] a group represented by the formula: —$(CH_2)_{q1}CONR^9$ $(CH_2)_{r1}$— (wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated), or [2] a group represented by the formula: —$(CH_2)_{q2}COO(CH_2)_{r2}$— (wherein each of $q^2$ and $r^2$ is an integer of 0 to 3 and their sum is not more than 3), each of $R^1$ and $R^2$ is hydrogen atom or $C_{1-6}$ alkyl which may be substituted, or $R^1$ and $R^2$ may form, together with the adjacent nitrogen atom, a 5- or 6-membered nitrogen-containing heterocyclic ring, and ring A is monocyclic aromatic ring which may be further substituted, or a salt or a prodrug thereof;

36. The pharmaceutical composition according to the above 35 which is an agent for preventing or treating senile dementia, Alzheimer's disease, Down's syndrome, Parkinson's disease, amyloid angiopathy or disorders due to amyloid-β protein in cerebrovascular disorders caused by the production and/or secretion of amyloid-β protein;

37. A method for inhibiting the production and/or the secretion of amyloid-β protein in mammal, which comprises administering to said mammal an effective amount of a compound represented by the formula:

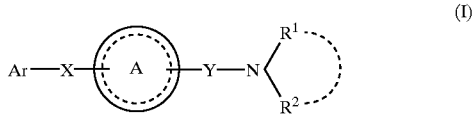
(I)

wherein Ar is an aromatic group which may be substituted, X and Y are the same and different and each is a bivalent group selected from —O—, —S—, —CO—, —SO—, —SO$_2$—, —NR$^8$—, —CONR$^8$—, SO$_2$NR$^8$— and —COO— (wherein R$^8$ is hydrogen atom, a hydrocarbon group which may be substituted or acyl) or a bivalent C$_{1-6}$ aliphatic hydrocarbon group which may contain one or two above bivalent groups, each of R$^1$ and R$^2$ is hydrogen atom or C$_{1-6}$ alkyl which may be substituted, or R$^1$ and R$^2$ may form, together with the adjacent nitrogen atom, a nitrogen-containing heterocyclic ring, and ring A is monocyclic aromatic ring which may be further substituted, or a salt or a prodrug thereof;

38. A method for preventing or treating senile dementia, Alzheimer's disease, Down's syndrome, Parkinson's disease, amyloid angiopathy or disorders due to amyloid-β protein in cerebrovascular disorders caused by the production and/or secretion of amyloid-β protein which comprises administering an effective amount of a compound represented by the formula:

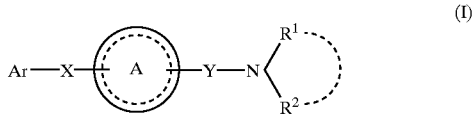
(I)

wherein Ar is an aromatic group which may be substituted, X and Y are the same and different and each is a bivalent group selected from —O—, —S—, —CO—, —SO—, —SO$_2$—, —NR$^8$—, —CONR$^8$—, —SO$_2$NR$^8$— and —COO— (wherein R$^8$ is hydrogen atom, a hydrocarbon group which may be substituted or acyl) or a bivalent C$_{1-6}$ aliphatic hydrocarbon group which may contain one or two above bivalent groups, each of R$^1$ and R$^2$ is hydrogen atom or C$_{1-6}$ alkyl which may be substituted, or R$^1$ and R$^2$ may form, together with the adjacent nitrogen atom, a nitrogen-containing heterocyclic ring, and ring A is monocyclic aromatic ring which may be further substituted, or a salt or a prodrug thereof;

39. Use of a compound represented by the formula:

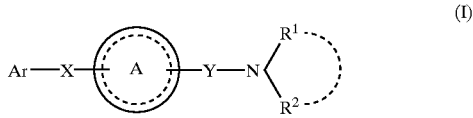
(I)

wherein Ar is an aromatic group which may be substituted, X and Y are the same and different and each is a bivalent group selected from —O—, —S—, —CO—, —SO—, —SO$_2$—, —NR$^8$—, —CONR$^8$—, —SO$_2$NR$^8$— and —COO— (wherein R$^8$ is hydrogen atom, a hydrocarbon group which may be substituted or acyl) or a bivalent C$_{1-6}$ aliphatic hydrocarbon group which may contain one or two above bivalent groups, each of R$^1$ and R$^2$ is hydrogen atom or C$_{1-6}$ alkyl which may be substituted, or R$^1$ and R$^2$ may form, together with the adjacent nitrogen atom, a nitrogen-containing heterocyclic ring, and ring A is monocyclic aromatic ring which may be further substituted, or a salt or a prodrug thereof, for manufacturing an inhibitor of the production and/or the secretion of amyloid-β protein; and 40. Use of a compound represented by the formula:

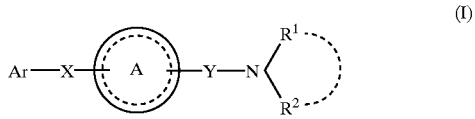
(I)

wherein Ar is an aromatic group which may be substituted, X and Y are the same and different and each is a bivalent group selected from —O—, —S—, —CO—, —SO—, —SO$_2$—, —NR$^8$—, —CONR$^8$—, —SO$_2$NR$^8$— and —COO— (wherein R$^8$ is hydrogen atom, a hydrocarbon group which may be substituted or acyl) or a bivalent C$_{1-6}$ aliphatic hydrocarbon group which may contain one or two above bivalent groups, each of R$^1$ and R$^2$ is hydrogen atom or C$_{1-6}$ alkyl which may be substituted, or R$^1$ and R$^2$ may form, together with the adjacent nitrogen atom, a nitrogen-containing heterocyclic ring, and ring A is monocyclic aromatic ring which may be further substituted, or a salt or a prodrug thereof, for manufacturing an agent for preventing or treating senile dementia, Alzheimer's disease, Down's syndrome, Parkinson's disease, amyloid angiopathy or disorders due to amyloid-β protein in cerebrovascular disorders caused by the production and/or secretion of amyloid-β protein.

Best Embodiment

As the term "C$_{1-6}$ alkyl which may be halogenated" used herein, for example, C$_{1-6}$ alkyl (e.g., methyl, ethyl, propyl, isopropyl, butyl, isobutyl, sec-butyl, tert-butyl, pentyl, hexyl, etc.) optionally having 1 to 5, preferably 1 to 3 halogen atoms (e.g., fluoro, chloro, bromo, iodo, etc.) can be used. Examples thereof include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

As the term "C$_{3-6}$ cycloalkyl which may be halogenated" used herein, for example, C$_{3-6}$ cycloalkyl (e.g., cyclopropyl, cyclobutyl, cyclopentyl, cyclohexyl, etc.) optionally having 1 to 5, preferably 1 to 3 halogen atoms (e.g., fluoro, chloro, bromo, iodo, etc.) can be used. Examples thereof include cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

As the term "C$_{1-6}$ alkoxy which may be halogenated" used herein, for example, C$_{1-6}$ alkoxy (e.g., methoxy, ethoxy, propoxy, butoxy, pentyloxy, etc.) optionally having 1 to 5, preferably 1 to 3 halogen atoms (e.g., fluoro, chloro, bromo, iodo, etc.) can be used. Examples thereof include methoxy, difluoromethoxy, trifluoromethoxy, ethoxy, 2,2,2- trifluoroethoxy, propoxy, isopropoxy, butoxy, 4,4,4-trifluorobutoxy, isobutoxy, sec-butoxy, pentyloxy, hexyloxy, etc. can be mentioned.

As the term "$C_{1-6}$ alkylthio which may be halogenated" used herein, for example, $C_{1-6}$ alkylthio (e.g., methylthio, ethylthio, propylthio, isopropylthio, butylthio, sec-butylthio, tert-butylthio, etc.) optionally having 1 to 5, preferably 1 to 3 halogen atoms (e.g., fluoro, chloro, bromo, iodo, etc.) can be used. Examples thereof include methylthio, difluoromethylthio, trifluoromethylthio, ethylthio, propylthio, isopropylthio, butylthio;, 4,4,4-trifluorobutylthio, pentylthio, hexylthio, etc.

As the term "$C_{1-6}$ alkyl-carbonyl which may be halogenated", for example, $C_{1-6}$ alkyl-carbonyl (e.g., acetyl, propanoyl, butanoyl, pentanoyl, hexanoyl, etc.) optionally having 1 to 5, preferably 1 to 3 halogen atoms (e.g., fluoro, chloro, bromo, iodo, etc.) can be used. Examples thereof include acetyl, monochloroacetyl, trifluoroacetyl, trichloroacetyl, propanoyl, butanoyl, pentanoyl, hexanoyl etc.

As the term "$C_{1-6}$ alkylsulfonyl" used herein, for example, $C_{1-6}$ alkylsulfonyl (e.g., methylsulfonyl, ethylsulfonyl, propylsulfonyl, isopropylsulfonyl, butylsulfonyl, sec-butylsulfonyl, tert-butylsulfonyl, etc.) optionally having 1 to 5, preferably 1 to 3 halogen atoms (e.g., fluoro, chloro, bromo, iodo, etc.) can be used. Examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl, etc.

As the term "$C_{1-6}$ alkyl-carboxamido which, may be halogenated" used herein, for example, $C_{1-6}$ alkyl-carboxamido (e.g., acetamido, etc.) optionally having 1 to 5, preferably 1 to 3 halogen atoms (e.g., fluoro, chloro, bromo, iodo, etc.) can be used. Examples thereof include acetamido, trifluoroacetamido, propanamido, butanamido, etc.

In the above-mentioned formula, as the aromatic group represented by Ar, for example, a monocyclic aromatic group, an aromatic ring assembly group, a fused aromatic group, etc. can be used.

As the "monocyclic aromatic group", for example, a monovalent group formed by removing any one of hydrogen atoms from benzene ring or a 5- or 6-membered aromatic heterocyclic ring can be used.

As the "5- or 6-membered aromatic heterocyclic ring" for example, a 5- or 6-membered aromatic heterocyclic ring having, in addition to carbon atom, one or more (e.g., 1 to 3, preferably 1 or 2) hetero atoms selected from nitrogen atom, sulfur atom and oxygen atom, etc. can be used. Examples thereof include thiophene, furan, pyrrole, imidazole, pyrazole, thiazole, oxazole, pyridine, pyrazine, pyrimidine, pyridazine rings, etc.

Examples of the above-mentioned monocyclic aromatic group include, preferably, phenyl, 2- or 3-thienyl, 2- or 3-furyl, 1-, 2- or 3-pyrrolyl, 2- or 4-imidazolyl, 3- or 4-pyrazolyl, 2-, 4- or 5-thiazolyl, 2-, 4- or 5-oxazolyl, 2-, 3- or 4-pyridyl, 2-pyrazinyl, 2-, 4- or 5-pyrimidinyl, 3- or 4-pyridazinyl, etc. Among them, phenyl, etc. are preferred.

As the "aromatic ring assembly group", for example, a group which is derived, by removing any one of hydrogen atoms from an assembled aromatic ring in which two or more, preferably two or three aromatic rings are directly joined to each other by single bond(s) and the number of such direct ring junctions is one less than the number of the aromatic rings involved can be used. The "aromatic ring" includes, for example, an aromatic hydrocarbon, an aromatic heterocyclic ring, etc.

The "aromatic hydrocarbon" includes, for example, a $C_{6-14}$ monocyclic or fused polycyclic (preferably, bi- or tri-cyclic) aromatic hydrocarbon compound (e.g., benzene, naphthalene, indene, anthracene, etc.), The "aromatic heterocyclic ring" includes, for example, 5- to 14-membered, preferably 5- to 10-membered aromatic heterocyclic rings containing one or more (e.g., 1 to 4, preferably 1 to 2) hetero atoms selected from the group consisting of nitrogen, sulfur and oxygen atoms in addition to carbon atoms, etc. Examples thereof include an aromatic heterocyclic ring, such as thiophene, benzothiophene, benzofuran, benzimidazole, benzoxazole, benzothiazole, benzisothiazole, naphtho[2,3-b]thiophene, furan, phenoxathiin, pyrrole, imidazole, pyrazole, oxazole, isoxzaole, 1,2,4-oxadiazole, 1,3,4-oxadizaole, 1,2,4-thiadizaole, 1,3,4-thiadiazaole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, furazan, phenoxazine, phthalimide, 2-, 3- or 4-pyridone, 2-, 3- or 4-quinolone, etc.; and a ring as formed through condensation of the above ring, preferably monocyclic ring, with one or more, preferably one or two aromatic rings (e.g., a benzene ring, etc.), etc.

The assembly of those aromatic rings in which the rings are directly bonded to each other via a single bond includes, for example, those to be composed of two or three, preferably two aromatic rings selected from the group consisting of a benzene ring, naphthalene ring and 5- to 10-membered (preferably 5- or 6-membered) aromatic heterocyclic ring. As preferred examples of the assembly of such aromatic rings, there are aromatic ring assembly groups composed of two or 3 aromatic rings selected from benzene, naphthalene, pyridine, pyrimidine, thiophen, furan, thiazole, isothiazole, 1,2,4-oxadiazole, 1,3,4-oxadiazole, 1,2,4-thiadiazole, 1,3,4-thiadiazole, quinoline, isoquinoline, indole, benzothiophen, benzoxazole, benzthiazole and benzofuran. Specific examples thereof include 2-, 3- or 4-biphenylyl, 3-(1-naphthyl)-1,2,4-oxadiazol-5-yl, 3-(2-naphthyl)-1,2,4-oxadiazol-5-yl, 3-(2-benzofuranyl)-1,2,4-oxadiazol-5-yl, 3-phenyl-1,2,4-oxadiazol-5-yl, 3-(2-benzoxazolyl)-1,2,4-oxadiazol-2-yl, 3-(3-indolyl)-1,2,4-oxadiazol-2-yl, 3-(2-indolyl)-1,2,4-oxadiazol-2-yl, 4-phenylthiazol-2-yl, 4-(2-benzofuranyl)thizaol-2-yl, 4-phenyl-1,3-oxazol-5-yl, 5-phenylisothiazol-4-yl, 5-phenyloxazol-2-yl, 4-(2-thienyl)phenyl, 4-(3-thienyl)phenyl, 3-(3-pyridyl)phenyl, 4-(3-pyridyl)phenyl, 6-phenyl-3-pyridyl, 5-phenyl-1,3,4-oxadiazol-2-yl, 4-(2-naphthyl)phenyl, 4-(2-benzofuranyl)phenyl, 4,4'-terphenyl, etc. Of those, preferred are 2-, 3- or 4-biphenylyl.

As the "fused aromatic group", a monovalent group formed by removing any one of hydrogen atoms from a fused polycyclic (preferably, bi- to tetra-cyclic, more preferably bi- to tri-cyclic) aromatic hydrocarbon ring can be used. As the "fused polycyclic aromatic ring", a fused polycyclic aromatic hydrocarbon, a fused polycyclic aromatic heterocyclic ring can be used.

As the "fused polycyclic aromatic hydrocarbon", for example, $C_{9-14}$ fused polycyclic (bi- or tri-cyclic) aromatic hydrocarbon (e.g., naphthalene, indene, anthracene, etc.), etc. can be used.

As the "fused polycyclic aromatic heterocyclic ring", for example, 9- to 14-membered, preferably, 9- to 10 membered fused polycyclic aromatic heterocyclic ring, etc. can be used. Examples thereof include aromatic heterocyclic rings such as benzofuran, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalimide, etc.

Specific examples of the above-mentioned fused aromatic group include 1-naphthyl, 2-naphthyl, 2-quinolyl, 3-quinolyl, 4-quinolyl, 2-benzofuranyl, 2-benzothiazolyl, 2-benzimidazolyl, 1-indolyl, 2-indolyl, 3-indolyl, etc. Among them, 1-naphthyl, 2-naphthyl, etc. are preferred.

The substituent for the aromatic group represented by Ar includes, for example, halogen atom (e.g., fluoro, chloro, bromo, iodo, etc.), $C_{1-3}$ alkylenedioxy (e.g., methylenedioxy, ethylenedioxy, etc.), nitro, cyano, $C_{1-6}$ alkyl which may be halogenated, $C_{6-10}$ aryloxy-$C_{1-6}$ alkyl (e.g., phenoxymethyl, etc.), $C_{1-6}$ alkyl-$C_{6-10}$ aryl-$C_{2-6}$ alkenyl (e.g., methylphenylethenyl, etc.), $C_{3-6}$ cycloalkyl which may be halogenated, $C_{7-16}$ aralkyl which may be substituted, $C_{1-6}$ alkoxy which may be halogenated, $C_{1-6}$ alkylthio which may be halogenated, hydroxy, $C_{6-10}$ aryloxy which may be substituted, $C_{6-10}$ aryl-$C_{7-16}$ aralkyloxy (e.g., phenylbenzyloxy, etc.), amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etch), 5- to 7-membered saturated cyclic amino which may be substituted, acyl, acylamino, acyloxy, etc. The "aromatic group" may have 1 to 5, preferably 1 to 3 substituents as mentioned above at possible positions of the aromatic ring, and when the number of substituents is two or more, those substituents may be the same as or different from one another.

Among these substituents of the aromatic group represented by Ar, as "$C_{7-16}$ aralkyl" of "$C_{7-16}$ aralkyl which may be substituted", for example, benzyl, phenethyl, nephthylmethyl, etc. can be used.

As "$C_{6-10}$ aryloxy" of "$C_{6-10}$ aryloxy which may be substituted", for example, phenyloxy, naphthyloxy, etc. can be used. The "substituent" which those "$C_{7-16}$ aralkyl which may be substituted" and "$C_{6-10}$ aryloxy which may be substituted" respectively may have, include, for example, 1 to 5 substituents selected from halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamido $C_{1-6}$ alkoxy-carboxamido (e.g., methoxycarboxamido, ethoxycarboxamido, propoxycarboxamido, butoxycarboxamido, etc.) $C_{1-6}$ alkylsulfonylamino (e.g., methylsulfonylamino, ethylsulfonylamino, etc.), $C_{1-6}$ alkyl-carbonyloxy (e.g., acetoxy, propanoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-8}$ alkyl-carbamoyloxy (e.g., dimethylcarbamoyloxy, diethylcarbamoyloxy, etc.), etc.

Among the substituent of the aromatic group represented by Ar, the "5- to 7-membered saturated cyclic amino" of "5- to 7-membered saturated cyclic amino which may be substituted" includes, for example, morpholino, thiomorpholino, piperazin-1-yl, piperidino, pyrrolidin-1-yl, hexamethyleneimin-1-yl, etc. The "substituents" of these "5- to 7-membered saturated cyclic amino which may be subsituted" include, for example, 1 to 3 substituents selected from optionally halogenated $C_{1-6}$ alkyl, optionally substituted $C_{6-14}$ aryl, optionally substituted $C_{7-19}$ aralkyl, optionally substituted 5- to 10-membered aromatic heterocyclic group, optionally substituted $C_{6-10}$ aryl-carbonyl, optionally halogenated $C_{1-6}$ alkyl-carbonyl, optionally halogenated $C_{1-6}$ alkylsulfonyl, etc.

The "$C_{6-14}$ aryl" of the "$C_{6-14}$ aryl which may be substituted" includes, for example, phenyl, 1-naphthyl, 2-naphthyl, 2-indenyl, 2-anthryl, etc. Preferred is phenyl.

The "$C_{7-19}$ aralkyl" of the "$C_{7-19}$ aralkyl which may be substituted" includes, for example, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc. Preferred is benzyl, etc.

The "5- to 10-membered aromatic heterocyclic group" of the "5- to 10-membered aromatic heterocyclic group which may be substituted" includes, for example, 2-, 3- or 4-pyridyl, 1-, 2- or 3-indolyl, 2- or 3-thienyl, etc. Preferred is 2-, 3- or 4-pyridyl, etc.

The "$C_{6-10}$ aryl-carbonyl" of the "$C_{6-10}$ aryl-carbonyl which may be substituted" includes, for example, benzoyl, 1-naphthoyl, 2-naphthoyl, etc.

The "substituent" which these "$C_{6-14}$ aryl which may be substituted", "$C_{7-19}$ aralkyl which may be substituted", "5- to 10-membered aromatic heterocyclic group which may be substituted" and "$C_{6-10}$ aryl-carbonyl which may be subsituted" respectively may have, includes, for example, 1 to 5 substituents selected from the group consisting of halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etec.), di-$C_{1-6}$ alkyl-carbamoyl (e.g., dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamido, $C_{1-6}$ alkoxy-carboxamido (e.g., methoxycarboxamido, ethoxycarboxamido, propoxycarboxamido, butoxycarboxamido, etc.) $C_{1-6}$ alkylsulfonylamino (e.g., methylsulfonylamino, ethylsulfonylamino, etc.), $C_{1-6}$ alkyl-carbonyloxy (e.g., acetoxy, propanoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-8}$ alkyl-carbamoyloxy (e.g., dimethylcarbamoyloxy, diethylcarbamoyloxy, etc.), etc.

The "acyl" of "acyl", "acylamino" and "acyloxy" as the substituent of the "aromatic group which may be subsituted" represented by Ar includes, for example, that represented by the formula: —CO—$R^3$, —CO—O$R^3$—CO—N$R^3R^4$, —CS—NH$R^3$, —SO$_2$—$R^{3a}$ or —SO—$R^{3a}$ wherein $R^3$ is (i) hydrogen atom, (ii) a hydrocarbon group which may be substituted, specifically, a heterocyclic group which may be substituted with 1 to 5 substituents selected from the group consisting of halogen atom, $C_{1-3}$ alkylenedioxy, nitro, cyano, $C_{1-6}$ alkyl which may be halogenated, $C_{3-6}$ cycloalkyl which may be halogenated, $C_{1-6}$ alkoxy which may be halogenated, $C_{1-6}$ alkylthio which may be halogenated, hydroxy, amino, mono- $C_{1-6}$ alkylamino, di-$C_{1-6}$ alkylamino, 5- to 7- membered cyclic amino which may be substituted, formyl, carboxy, carbamoyl, $C_{1-6}$ alkyl-carbonyl which may be halogenated, $C_{7-16}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl,; di-$C_{1-6}$ alkyl-carbamoyl, $C_{6-10}$ aryl-carbamoyl, $C_{1-6}$ alkylsulfonyl which may be halogenated, $C_{6-10}$ arylsulfonyl, formylamino, $C_{1-6}$ alkyl-carboxamido which may be halogenated, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-8}$ alkyl-carbamoyloxy, $C_{6-10}$ aryl-carbamoyloxy, nicotinoyloxy and $C_{6-10}$ aryloxy, or (iii) a heterocyclic group which may be substituted, specifically, a heterocyclic group which may be substituted with 1 to 5 substituents selected from the group consisting of halogen atom, $C_{1-3}$ alkylenedioxy, nitro, cyano, $C_{1-6}$ alkyl which may be halogenated, $C_{3-6}$ cycloalkyl which may be halogenated, $C_{1-6}$ alkoxy which may be halogenated, $C_{1-6}$ alkylthio which may be halogenated, hydroxy, amino, mono- $C_{1-6}$ alkylamino, di-$C_{1-6}$ alkylamino, 5- to 7- membered cyclic amino which may be substituted, formyl, carboxy, carbamoyl, $C_{1-6}$ alkyl-carbonyl which may be halogenated, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, $C_{1-6}$ alkylsulfonyl which may be halogenated, $C_{6-10}$ arylsulfonyl, formylamino, $C_{1-6}$ alkyl-carboxamido which may be halogenated, $C_{6-10}$ aryl-carboxamido, $C_{6-10}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-8}$ alkyl-carbamoyloxy, $C_{6-10}$ aryl-carbamoyloxy, nicotinoyloxy and $C_{6-10}$ aryloxy, $R^{3a}$ is (i) a hydrocarbon group which may be substituted, specifically, a heterocyclic group which may be substituted with 1 to 5 substituents selected from the group consisting of halogen atom, $C_{1-3}$ alkylenedioxy, nitro, cyano, $C_{1-6}$ alkyl which may be halogenated, $C_{3-6}$ cycloalkyl which may be halogenated, $C_{1-6}$ alkoxy which may be halogenated, $C_{1-6}$ alkylthio which may be halogenated, hydroxy, amino, mono- $C_{1-6}$ alkylamino, di-$C_{1-6}$ alkylamino, 5- to 7- membered cyclic amino which may be substituted, formyl, carboxy, carbamoyl, $C_{1-6}$ alkyl-carbonyl which may be halogenated, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{1-6}$ alkylsulfonyl which may be halogenated, $C_{6-10}$ arylsulfonyl, formylamino, $C_{1-6}$ alkyl-carboxamido which may be halogenated, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-8}$ alkyl-carbamoyloxy, $C_{6-10}$ aryl-carbamoyloxy, nicotinoyloxy and $C_{6-10}$ aryloxy, or (iii) a heterocyclic group which may be substituted, specifically, a heterocyclic group which may be substituted with 1 to 5 substituents selected from the group consisting of halogen atom, $C_{1-3}$ alkylenedioxy, nitro, cyano, $C_{1-6}$ alkyl which may be halogenated, $C_{3-6}$ cycloalkyl which may be halogenated, $C_{1-6}$ alkoxy which may be halogenated, $C_{1-6}$ alkylthio which may be halogenated, hydroxy, amino, mono- $C_{1-6}$ alkylamino, di-$C_{1-6}$ alkylamino, 5- to 7- membered cyclic amino which may be substituted, formyl, carboxy, carbamoyl, $C_{1-6}$ alkyl-carbonyl which may be halogenated, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, $C_{1-6}$ alkylsulfonyl which may be halogenated, $C_{6-10}$ arylsulfonyl, formylamino, $C_{1-6}$ alkyl-carboxamido which may be halogenated, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-8}$ alkyl-carbamoyloxy, $C_{6-10}$ aryl-carbamoyloxy, nicotinoyloxy and $C_{6-10}$ aryloxy, or (iii) a heterocyclic group which may be substituted, specifically, a heterocyclic group which may be substituted with 1 to 5 substituents selected from the group consisting of halogen atom, $C_{1-3}$ alkylenedioxy, nitro, cyano, $C_{1-6}$ alkyl which may be halogenated, $C_{3-6}$ cycloalkyl which may be halogenated, $C_{1-6}$ alkoxy which may be halogenated, $C_{1-6}$ alkylthio which may be halogenated, hydroxy, amino, mono- $C_{1-6}$ alkylamino, di-$C_{1-6}$ alkylamino, 5- to 7- membered cyclic amino which may be substituted, formyl, carboxy, carbamoyl, $C_{1-6}$ alkyl-carbonyl which may be halogenated, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, $C_{1-6}$ alkylsulfonyl which may be halogenated, $C_{6-10}$ arylsulfonyl, formylamino, $C_{1-6}$ alkyl-carboxamido which may be halogenated, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-8}$ alkyl-carbamoyloxy, $C_{6-10}$ aryl-carbamoyloxy, nicotinoyloxy and $C_{6-10}$ aryloxy, $R^4$ is hydrogen atom or $C_{1-6}$ alkyl, or $R^3$ and $R^4$ may form, together with the adjacent nitrogen atom, a nitrogen-containing ring.

The "5- to 7-membered saturated cyclic amino" as the substituent of $R^3$ or $R^{3a}$ is the same as those mentioned above.

The "hydrocarbon group" of the "hydrocarbon group which may be substituted" represented by $R^3$ or $R^{3a}$ is a group formed by removing any one of hydrogen atoms from a hydrocarbon compound, as exemplified by acyclic or cyclic hydrocarbon group such as alkyl, alkenyl, alkynyl, cycloalkyl, aryl, aralkyl, etc. Among them, the following $C_{1-19}$ acyclic or cyclic hydrocarbon group is preferred:

a) $C_{1-6}$ alkyl (e.g., methyl, ethyl, propyl, isopropyl, butyl, isobutyl, sec-butyl, tert-butyl, pentyl, hexyl, etc.), b) $C_{2-6}$ alkenyl (e.g., vinyl, allyl, isopropenyl, 2-butenyl, etc.), c) $C_{2-6}$ alkynyl (e.g., ethynyl, propargyl, 2-butynyl, etc.), d) $C_{3-6}$ cycloalkyl (e.g., cyclopropyl, cyclobutyl, cyclopentyl, cyclohexyl, etc.), and the $C_{3-6}$ cycloalkyl being optionally condensed with one a benzene ring, e) $C_{6-14}$ aryl (e.g., phenyl, 1-naphthyl, 2-naphthyl, 2-indenyl, 2-anthryl, etc.), preferably phenyl, f) $C_{7-19}$ aralkyl (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

The heterocyclic group represented by $R^3$ or $R^{3a}$ includes, for example, a monovalent group formed by removing any one of hydrogen atoms from 5- to 14-membered (monocyclic, bicyclic or tricyclic) heterocyclic ring containing 1 to 4 hetero atoms of 1 or 2 species selected from the group consisting of nitrogen, oxygen and sulfur atoms in addition to carbon atoms, preferably, (i) 5- to 14-membered, preferably 5- to 10-membered aromatic heterocyclic ring, (ii) 5- to 10-membered non-aromatic heterocyclic ring or (iii) a 7- to 10-membered bridged heterocyclic ring.

The above-mentioned "5- to 14-membered, preferably 5- to 10-membered aromatic heterocyclic ring" includes, for example, an aromatic heterocyclic ring such as thiophene, benzothiophene, benzofuran, benzimidazole, benzoxazole, benzothiazole, benzisothiazole, naphtho[2,3-b]thiophene, furan, phenoxathiine, pyrrole, imidazole, pyrazole, oxadiazole, 1,2,4-oxadiazole, 1,3,4-oxadiazole, 1,2,4- thiadiazole, 1,3,4-thiadiazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.; and a ring as formed through condensation of those rings, preferably a monocyclic ring, with one or more, preferably one or two aromatic rings (e.g., a benzene ring, etc.), etc.

The above-mentioned "5- to 10-membered non-aromatic heterocyclic ring" includes, for example, pyrrolidine, imidazoline, pyrazolidine, pyrazoline, piperidine, piperazine, morpholine, thiomorpholine, etc.

The above-mentioned "7- to 10-membered bridged heterocyclic ring" includes, for example, quinuclidine, 7-azabicyclo[2,2,1]heptane, etc.

Preferable examples of the "heterocyclic group" include, for example, 5- to 10-membered (monocyclic or bicyclic) heterocyclic group containing 1 to 4 hetero atoms of 1 or 2 species selected from the group consisting of nitrogen, oxygen and sulfur atoms in addition to carbon atoms. Specific examples thereof include an aromatic heterocyclic group such as 2- or 3-thienyl, 2-, 3- or 4-pyridyl, 2- or 3-furyl, 2-, 3-, 4-, 5- or 8-quinolyl, 4-isoquinolyl, pyrazinyl, 2- or 4-pyrimidinyl, 3-pyrrolyl, 2-imidazolyl, 3-pyridazinyl, 3-isothiazolyl, 3-isoxazolyl, 1-indolyl, 2-indolyl, 2-isoindolylnyl, etc; and a non-aromatic heterocyclic group such as 1-, 2 or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

Among these groups, a 5- or 6-membered heterocyclic group containing 1 to 3 hetero atoms selected from the group consisting of nitrogen, oxygen and sulfur atoms in addition to carbon atoms. Specific examples thereof include 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-, 2-, or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

The "$C_{1-6}$ alkyl" represented by R4 includes, for example, methyl, ethyl, propyl, isopropyl, butyl, isobutyl, sec-butyl, tert-butyl, pentyl, hexyl, etc.

The "nitrogen-containing heterocyclic ring" formed by, taken together with the adjacent nitrogen atom, $R^3$ and $R^4$ includes, for example, 5- to 7-membered nitrogen-containing heterocyclic ring having one nitrogen atom and optionally having 1 to 3 hetero atoms selected from the group consisting of nitrogen, oxygen and sulfur atoms in addition to carbon atoms. Such examples include piperidine, morpholine, thiomorpholine, piperazine, pyrrolidine, etc.

Preferred examples of the "acyl" as the "substituent" of the "aromatic ring" represented by Ar include formyl, carboxy, carbamoyl, $C_{1-6}$ alkyl-carbonyl which; may be halogenated, $C_{1-6}$ alkoxy-carbonyl (e.g., methoxycarbonyl, ethoxycarbonyl, propoxycarbonyl, tert-butoxycarbonyl, etc.), $C_{6-10}$ aryl-carbonyl which may be substituted, $C_{6-10}$ aryloxy-carbonyl which may be substituted, $C_{7-16}$ aralkyloxy-carbonyl which may be substituted, 5- or 6-membered heterocycle carbonyl which may be substituted, mono-$C_{1-6}$ alkyl-carbamoyl, di-$C_{1-6}$ alkyl-carbamoyl (e.g., dimethylcarbamoyl, diethylcarbamoyl, ethylmethylcarbamoyl, etc.), $C_{6-10}$ aryl-carbamoyl which may be substituted, 5- or 6-membered heterocycle carbamoyl which may be substituted, $C_{1-6}$ alkylsulfonyl which may be halogenated, $C_{6-10}$ arylsulfonyl which may be substituted, etc.

Among them, "$C_{6-10}$ aryl-carbonyl" of "$C_{6-10}$ aryl-carbonyl which may be substituted" includes, for example, benzoyl, 1-naphthoyl, 2-naphthoyl, etc. "$C_{6-10}$ aryloxy-carbonyl" of "$C_{6-10}$ aryloxy-carbonyl which may be substituted" includes, for example, phenoxycarbonyl, etc. "$C_{7-16}$ aralkyloxy-carbonyl" of "$C_{7-16}$ aralkyoxy-carbonyl which may be substituted" includes, for example, benzyloxycarbonyl, phenethyloxycarbonyl, etc. "5- or 6-membered heterocyclic carbonyl" of "5- or 6-membered heterocyclic carbonyl which may be substituted" includes, for example, nicotinoyl, isonicotinoyl, 2-thenoyl, 3-thenoyl, 2-furoyl, 3-furoyl, morpholinocarbonyl, piperidinocarbonyl, 1-pyrrolidinylcarbonyl, etc. "$C_{6-10}$ aryl-carbamoyl"; of "$C_{6-10}$ aryl-carbamoyl which may be subsituted" includes, for example, phenylcarbamoyl, 1-naphthylcarbamoyl, 2-naphthylcarbamoyl, etc. "5- or 6-membered heterocyclic-carbamoyl" of "5- or 6-membered heterocyclic carbamoyl which may be subsituted" includes, for example, 2-pyridylcarbamoyl, 3-pyridylcarbamoyl, 4-pyridyl-carbamoyl, 2-thienylcarbamoyl, 3-thienylcarbamoyl, etc. "$C_{6-10}$ arylsulfonyl" of "$C_{6-10}$ arylsulfonyl which may be subsituted" includes, for example, benzenesulfonyl, 1-naphthalenesulfonyl, 2-naphthalenesulfonyl, etc.

The "substituent" of these "$C_{6-10}$ aryl-carbonyl which may be substituted", "$C_{6-10}$ aryloxy-carbonyl which may be substituted", "$C_{7-16}$ aralkyoxy-carbonyl which may be substituted", "5- or 6-membered heterocyclic carbonyl which may be substituted", "$C_{6-10}$ aryl-carbamoyl which may be subsituted", "5- or 6-membered heterocyclic carbamoyl which may be subsituted" and "$C_{6-10}$ arylsulfonyl which may be subsituted" includes, for example, 1 to 5, preferably 1 to 3 substituents selected from the group consisting of halogen atom, $C_{1-3}$ alkylenedioxy, nitro, cyano, $C_{1-6}$ alkyl which may be halogenated, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, formyl, carboxy, carbamoyl, $C_{1-6}$ alkyl-carbonyl which may be halogenated, $C_{1-6}$ alkoxy-carbonyl, mono-$C_{1-6}$ alkyl-carbamoyl, di-$C_{1-6}$ alkyl-carbamoyl, $C_{1-6}$ alkylsulfonyl which may be halogenated, $C_{6-10}$ arylsulfonyl, formylamino, $C_{1-6}$ alkyl-carboxamido which may be halogenated, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-8}$ alkyl-carbamoyloxy.

The "acylamino" as the "substituent" of the "aromatic group which may be substituted" represented by the above Ar includes, for example, an amino substituted by 1 or 2 "acyl" described in detail in the above "substituent" for the "aromatic group which may be substituted" represented by Ar. Preferred is an acylamino of the formula: —$NR^5$—$COR^6$, —$NR^5$—$COOR^{6a}$, —$NR^5$—$SO_2RR^{6a}$ or —$NR^5$—$CONR^{6a}R^{6b}$ wherein $R^5$ is hydrogen atom or $C_{1-6}$ alkyl, $R^6$ is as defined above with respect to $R^3$, $R^{6a}$ is as defined above with respect to $R^{3a}$ and $R^{6b}$ is as defined with respect to $R^4$, etc.

The "$C_{1-6}$ alkyl" for $R^5$ and $R^{6b}$ includes the "$C_{1-6}$ alkyl" shown by $R^4$ above.

Preferred examples of the "acylamino" as the "substituent" of the "aromatic group which may be substituted" represented by Ar include formylamino, $C_{1-6}$ alkyl-carboxamido which may be halogenated, $C_{6-10}$ aryl-carboxamido (e.g., phenylcarboxamido, naphthylcarboxamido, etc.), $C_{1-6}$ alkoxy-carboxamido (e.g., methoxycarboxamido, ethoxycarboxamido, propoxycarboxamido, butoxycarboxamido, etc.), $C_{1-6}$ alkyl-sulfonylamino (e.g., methylsulfonylamino, ethylsulfonylamino, etc.), etc.

The above-mentioned "acyloxy" as the "substituent" of the "aromatic group which may be substituted" represented by the above Ar includes, for example, an oxy substituted by one "acyl" described in detail in the foregoing referring to the "substituent" for the "aromatic ring assembly group which may be substituted". Preferred is an acyloxy of the formula: —O—COR$^7$, —O—COOR$^7$ or —O—CONHR$^7$ wherein R$^7$ is as defined with respect to the above R$^3$, etc.

Preferred examples of "acyloxy" as the "substituent" of the "aromatic group which may be substituted" represented by the above Ar include $C_{1-6}$ alkyloxy-carbonyl (e.g., acetoxy, propanoyloxy, etc.), $C_{6-10}$ aryl oxy-carbonyl which may be substituted (e.g., benzoyloxy, 1-naphthoyloxy, 2-naphthoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-10}$ aryl-carbamoyloxy which may be substituted (e.g., phenylcarbamoyloxy, naphthylcarbamoyloxy, etc.), nicotinoyloxy, etc. Preferred examples of the "substituent" or these "$C_{6-10}$ aryl-carboxamido which may be substituted", "$C_{6-10}$ aryl-carbonyloxy which may be substituted" and "$C_{6-10}$ aryl-carbamoyloxy which may be substituted" include the same substituents as those of the above "$C_{6-10}$ aryl-carbonyl which may be substituted".

Among them, preferred Ar is the aromatic ring assembly group which may be substituted (in particular, 2-, 3- or 4-biphenylyl, etc.).

Each of X and Y is a bivalent group selected from —O—, —S—, —CO—, —SO—, —SO$_2$, —NR$^8$—, —CONR$^8$—, —SO$_2$NR$^8$— and —COO— (wherein R$^8$ is hydrogen atom, a hydrocarbon group which may be substituted or acyl) or a bivalent $C_{1-6}$ aliphatic hydrocarbon group which may contain one or two above bivalent groups.

Examples of the hydrocarbon group which may be subsituted represented by R$^8$ include the same group as the "hydrocarbon group which may be substituted" of the above R$^3$. Among them, $C_{1-6}$ alkyl which may be halogenated, etc. are preferred.

Examples of the acyl represented by R$^8$ include the same group as the "acyl" as the substituent of the aromatic group represented by Ar. Among them, preferred examples thereof include formyl, carbamoyl, $C_{1-6}$ alkyl-carbonyl which may be halogenated, $C_{1-6}$ alkoxy-carbonyl. (e.g., methoxycarbonyl, ethoxycarbonyl, propoxycarbonyl, tert-butoxycarbonyl, etc.), $C_{6-10}$ aryl-carbonyl which may be substituted, $C_{6-10}$ aryloxy-carbonyl which may be substituted, $C_{7-16}$ aralkyloxy-carbonyl which may be substituted, 5- or 6-membered heterocycle carbonyl which may be substituted, mono-$C_{1-6}$ alkyl-carbamoyl, di-$C_{1-6}$ alkyl-carbamoyl (e.g., dimethylcarbamoyl, diethylcarbamoyl, ethylmethylcarbamoyl, etc.), $C_{6-10}$ aryl-carbamoyl which may be substituted, 5- or 6-membered heterocycle carbamoyl which may be substituted, $C_{1-6}$ alkyl-sulfonyl which may be halogenated, $C_{6-10}$ arylsulfonyl which may be substituted, etc. In particular, $C_{1-6}$ alkyl-carbonyl is preferred.

The $C_{1-6}$ aliphatic hydrocarbon group includes, for example, $C_{1-6}$ alkylene, $C_{2-6}$ alkenylene, $C_{2-6}$ alkynylene, etc.

The $C_{1-6}$ alkylene includes, for example, in addition to a straight chain alkylene such as —CH$_2$—, —(CH$_2$)$_2$—, —(CH$_2$)$_3$—, —(CH$_2$)$_4$—, —(CH$_2$)$_5$—, —(CH$_2$)$_6$—, etc., $C_{1-3}$ alkylene (e.g., —CH$_2$—, —(CH$_2$)$_2$—, —(CH$_2$)$_3$—, etc.) which may have 1 to 3 $C_{1-3}$ alkyl groups, etc.

The $C_{2-6}$ alkenylene includes for example, in addition to a straight chain $C_{2-6}$ alkenylene such as —CH=CH—, —CH$_2$——CH=CH—, —CH=CH—CH$_2$—, —CH$_2$—CH=CH—CH$_2$—, —(CH$_2$)$_2$—$_2$—CH=CH—CH$_2$—,— (CH$_2$)$_2$—CH=CH—(CH$_2$)$_2$, —(CH$_2$)$_3$—CH=CH—CH$_2$—, etc., $C_{2-3}$ alkenylene (e.g., —CH=CH—, —CH$_2$—CH=CH—, etc.) which may have 1 to 3 $C_{1-3}$ alkyl groups, etc.

The $C_{2-6}$ alkynylene includes, for example, in addition to a straight chain $C_{2-6}$ alkynylene such as —C≡C—, —CH$_2$—C≡C—, —C≡C—CH$_2$—, —C≡C—CH$_2$CH$_2$—, —CH$_2$CH$_2$—C≡C—, —CH$_2$—C≡C—CH$_2$, —(CH$_2$)$_2$—C≡C—CH$_2$—, —(CH$_2$)$_2$—C≡C—(CH$_2$)$_2$—, —(CH$_2$)$_3$—C≡C—CH$_2$—, etc., $C_{2-3}$ alkynylene (e.g., —C≡C—, —CH$_2$—C≡C—, —C≡C—CH$_2$—, —C≡C—CH$_2$CH$_2$—, —CH$_2$CH$_2$—C≡C—, etc.) having 1 to 3 $C_{1-3}$ alkyl groups.

Preferred examples of the $C_{1-6}$ aliphatic hydrocarbon group includes, in particular, a $C_{1-3}$ aliphatic hydrocarbon group such as $C_{1-3}$ alkylene, $C_{2-3}$ alkenylene, $C_{2-6}$ alkynylene, etc.

Examples of a bivalent $C_{1-6}$ aliphatic hydrocarbon group which may contain one or two bivalent groups selected from —O—, —S—, —CO—, —SO—, —SO$_2$—, —NR$^8$—, —CONR$^8$—, —SO$_2$NR$^8$— and —COO— represented by X include (i) —(CH$_2$)$_w$O—, —(CH$_2$)$_w$S—, —(CH$_2$)$_w$CO—, —(CH$_2$)$_w$SO—, —(CH$_2$)$_w$SO$_2$—, —(CH$_2$)$_w$NR$^8$—, —(CH$_2$)$_w$CONR$^8$—, —(CH$_2$)$_w$NR$^8$CO—, —(CH$_2$)$_w$SO$_2$NR$^8$—, —(CH$_2$)$_w$NR$^8$SO$_2$—, —(CH$_2$)$_w$COO—, (ii) —O (CH$_2$)$_w$—, —S(CH$_2$)$_w$—, —CO(CH$_2$)$_w$—, —SO (CH$_2$)$_w$—, —SO$_2$(CH$_2$)$_w$—, —NR$^8$(CH$_2$)$_w$—, —CONR$^8$(CH$_2$)$_w$—, —NR$^8$CO (CH$_2$)$_w$—, —SO$_2$NR$^8$ (CH$_2$)$_w$—, —NR$^8$SO$_2$(CH$_2$)$_w$—, —COO(CH$_2$)

(iii) —(CH$_2$)$_{w1}$O (CH$_2$)$_{w2}$—, —(CH$_2$)$_{w1}$S (CH$_2$)$_{w2}$—, —(CH$_2$)$_{w1}$CO(CH$_2$)$_{w2}$—, —(CH$_2$)$_{w1}$SO(CH$_2$)$_{w2}$—, —(CH$_2$)$_{w1}$SO$_2$(CH$_2$)$_{w2}$—, —(CH$_2$)$_{w1}$NR$^8$(CH$_2$)$_{w2}$—, —(CH$_2$)$_{w1}$CONR$^8$(CH$_2$)$_{w2}$—, —(CH$_2$)$_{w1}$NR$^8$CO (CH$_2$)$_{w2}$—, —(CH$_2$)$_{w1}$SO$_2$NR$^8$(CH$_2$)$_{w1}$—, —(CH$_2$)$_{w1}$NR$^8$SO$_2$(CH$_2$)$_{w1}$—, —(CH$_2$)$_{w1}$COO (CH$_2$)$_{w1}$—, etc.

Examples of a bivalent $C_{1-6}$ aliphatic hydrocarbon group which may contain one or two above bivalent groups selected from —O—, —S—, —CO—, —SO—, SO$_2$—, —NR$^8$—, —CONR$^8$—, —SO$_2$NR$^8$— and —COO— or represented by Y include (i) —O(CH$_2$)$_w$—, —S(CH$_2$)$_w$—, —CO (CH$_2$)$_{w1}$——SO (CH$_2$)$_w$—, —SO$_2$(CH$_2$)$_w$—, —NR$^8$(CH$_2$)$_w$—, —CONR$^8$(CH$_2$)$_w$—, —NR$^8$CO(CH$_2$)$_w$—, —SO$_2$NR$^8$ (CH$_2$)$_w$—, —NR$^8$SO$_2$(CH$_2$)$_w$—, —COO (CH$_2$)$_w$—, (ii) —(CH$_2$)$_{w1}$O(CH$_2$)$_{w2}$—, —(CH$_2$)$_{w1}$S(CH$_2$)$_{w2}$—, —(CH$_2$)$_{w1}$CO(CH$_2$)$_{w2}$—, —(CH$_2$)$_{w1}$SO(CH$_2$)$_{w2}$—, —(CH$_2$)$_{w1}$SO$_2$(CH$_2$)$_{w2}$—, —(CH$_2$)$_{w1}$NR$^8$(CH$_2$)$_{w2}$—, —(CH$_2$)$_{w1}$CONR$^8$(CH$_2$)$_{w2}$—, —(CH$_2$)$_{w1}$NR$^8$CO (CH$_2$)$_{w2}$—, —(CH$_2$)$_{w1}$SO$_2$NR$^8$(CH$_2$)$_{w1}$—, —(CH$_2$)$_{w1}$NR$^8$SO$_2$(CH$_2$)$_{w1}$—, —(CH$_2$)$_{w1}$COO(CH$_2$)$_{w1}$—, etc.

w is an integer of 1 to 6, preferably 1 to 4, in particular 1 to 2.

Each of w1 and w2 is integer of 1 to 3, preferably 1 or 2.

In addition, preferred examples of X and Y also include $C_{1-5}$ alkylene, $C_{2-5}$ alkenylene, $C_{2-5}$ alkynylene, —CH$_2$—Z—, —(CH$_2$)$_2$—Z—, —(CH$_2$)$_3$—Z—, —(CH$_2$)$_4$—Z—, —Z—CH$_2$—, —Z—(CH$_2$)$_2$—, —Z—(CH$_2$)$_3$—, —Z—(CH$_2$)$_4$—, —Z—CH$_2$—Z—, —Z—(CH$_2$)$_2$—Z—, —Z—(CH$_2$)$_3$—Z—, —CH$_2$—Z—CH$_2$—, —(CH$_2$)$_2$—Z-CH$_2$—, —(CH$_2$)$_3$—Z—CH$_2$—, —CH$_2$—Z—(CH$_2$)$_2$— or —CH$_2$—Z—(CH$_2$)$_3$— wherein Z is —O—, —S—, —CO—, —SO—, —SO$_2$—, —NR$^8$—, —CONR$^8$—, —SO$_2$NR$^8$— or —COO—, and, when two Z's are contained in one formula, they may be the same or different.

Among them, preferred examples of X include [1] a group represented by the formula:—(CH$_2$)$_{p1}$O— (wherein p$^1$ is an integer of 1 to 3), [2] —(CH$_2$)$_{p2}$— (wherein p$^2$ is an integer of 1 to 3), [3] —(CH$_2$)$_{p3}$OCONH— (wherein p$^3$ is an integer of 1 to 3) [4] CONH or [5] SO$_2$NH, etc., in particular, —(CH$_2$)$_{p1}$O— (wherein p$^1$ is an integer of 1 to 3), etc.

Preferred examples of Y include [1] a group represented by the formula: —(CH$_2$)$_{q1}$CONR$^9$(CH$_2$)$_{r1}$— (wherein each of q$^1$ and r$^1$ is an integer of 0 to 3 and their sum is an integer of not more than 3, R$^9$ is hydrogen atom or C$_{1-6}$ alkyl which may be halogenated or C$_{1-6}$ alkyl-carbonyl which may be halogenated), or [2] a group represented by the formula: —(CH$_2$)$_{q2}$COO(CH$_2$)$_{r2}$— (wherein each of q$^2$ and r$^2$ is an integer of 0 to 3 and their sum is not more than 3), etc. in particular, a group represented by the formula: —(CH$_2$)$_{q1}$CONR$^9$(CH$_2$)$_{r1}$— (wherein each of q$^1$ and r$^1$ is an integer of 0 to 3 and their sum is an integer of not more than 3, R$^9$ is hydrogen atom or C$_{1-6}$ alkyl which may be halogenated or C$_{1-6}$ alkyl-carbonyl which may be halogenated), etc.

The C$_{1-6}$ alkyl represented by R$^1$ and R$^2$ includes, for example, methyl, ethyl, propyl, isopropyl, butyl; isobutyl, sec-butyl, tert-butyl, pentyl, hexyl, etc. In particular, methyl, ethyl, propyl, etc. are preferred.

Examples of the substituent of C$_{1-6}$ alkyl represented by R$^1$ and R$^2$ include 1 to 5, preferably, 1 to 3 substituents selected from the group consisting of halogen atoms (e.g., fluoro, chloro, bromo, iodo, etc.), C$_{1-3}$ alkylenedioxy (e.g., methylenedioxy, ethylenedioxy, etc.), nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino (e.g., methylamino, ethylamino, propylamino, isopropylamino, butylamino, etc.), di-C$_{1-6}$ alkylamino (e.g., dimethylamino, diethylamino, dipropylamino, dibutylamino, ethylmethylamino, etc.), formyl, carboxy, carbamoyl, optionally halogenated C$_{1-6}$ alkyl-carbonyl, C$_{1-6}$ alkoxy-carbonyl (e.g., methoxycarbonyl, ethoxycarbonyl, propoxycarbonyl, tert-butoxycarbonyl, etc.), mono-C$_{1-6}$ alkyl-carbamoyl (e.g., methylcarbamoyl, ethylcarbamoyl, etec.), di-C$_{1-6}$ alkyl-carbamoyl (e.g., dimethylcarbamoyl, diethylcarbamoyl, ethylmethylcarbamoyl, etc.), optionally halogenated C$_{1-6}$ alkylsulfonyl, formylamino, optionally halogenated C$_{1-6}$ alkyl-carboxamido, C$_{1-6}$ alkoxy-carboxamido (e.g., methoxycarboxamido, ethoxycarboxamido, propoxycarboxamido, butoxycarboxamido, etc.) C$_{1-6}$ alkylsulfonylamino (e.g., methylsulfonylamino, ethylsulfonylamino, etc.), C$_{1-6}$ alkyl-carbonyloxy (e.g., acetoxy, propanoyloxy, etc.), C$_{1-6}$ alkoxy-carbonyloxy (e.g., methoxycarbonyloxy, ethoxycarbonyloxy, propoxycarbonyloxy, butoxycarbonyloxy, etc.), mono-C$_{1-6}$ alkyl-carbamoyloxy (e.g., methylcarbamoyloxy, ethylcarbamoyloxy, etc.), di-C$_{1-8}$ alkyl-carbamoyloxy (e.g., dimethylcarbamoyloxy, diethylcarbamoyloxy, etc.), optionally substituted aromatic group, etc. When two or more substituents are present, they may be the same or different. The optionally substituted aromatic group is the same as the optionally substituted aromatic group of the above Ar.

The "nitrogen-containing heterocyclic ring" of the "nitrogen-containing heterocyclic ring which may be substituted" to be formed by R$^1$ and R$^2$ along with the adjacent nitrogen atom includes, for example, a 3- to 8-member nitrogen-containing heterocyclic ring having one nitrogen atom and optionally having 1 to 3 hetero atoms selected from the group consisting of nitrogen, oxygen and sulfur atoms in addition to carbon atoms. Specific examples thereof include aziridine, azetidine, morpholine, thiomorpholine, piperidine, piperazine, pyrrolidine, hexamethyleneimine, heptamethyleneimine, hexahydropyrimidine, 1,4-diazepam as well as unsaturated cyclic amines corresponding to those rings (e.g., 1,2,5,6-tetrahydropyridine, etc.), etc. Of those, preferred are morpholine, piperidine, piperazine, pyrrolidine, etc.

The "substituent" of the "nitrogen-containing heterocyclic ring which may be substituted" formed by R$^1$ and R$^2$ taken together with the adjacent nitrogen atom include 1 to 3 substituents which are the same as the substituents of the above "5- to 7-membered saturated cyclic amino".

Preferred examples of R$^1$ and R$^2$ include [1] hydrogen atom or [2] C$_{1-6}$ alkyl which may be substituted by carboxy, C$_{1-6}$alkoxy-carbonyl or di-C$_{1-6}$ alkylnitrile, or R$^1$ and R$^2$ form, together with the adjacent nitrogen atom, 5- or 6-membered nitrogen-containing heterocyclic ring (e.g., piperidino, pyrolidin-1-yl, etc.).

Further, preferably, one of R$^1$ and R$^2$ is C$_{1-6}$ alkyl which may be substituted, more preferably, both R$^1$ and R$^2$ are C$_{1-6}$ alkyl which may be substituted.

Ring A is, for example, a benzene ring, or a 5- or 6-membered aromatic heterocyclic ring, etc.

The "5- or 6-membered aromatic heterocyclic ring" includes, for example, 5- or 6-membered aromatic heterocyclic ring containing one or more (e.g., 1 to 3, preferably 1 or 2) hetero atoms selected from the group consisting of nitrogen, oxygen and sulfur atoms in addition to carbon atoms. Specific examples thereof inculde thiophene, furan, pyrrole, imidazole, pyrazole, pyridine, pyrazine, pyrimidine, pyridazine, etc.

Preferred examples of ring A include a benzene ring or a 6-membered nitrogen-containing aromatic heterocyclic ring, preferably a benzene ring, a pyridine ring or 2-pyridone ring, in particular, a benzene ring or a pyridine ring.

Ring A is substituted by a group represented by the formula: Ar—X— at a substitutable position thereof. Ring A may be further substituted, in addition to the group represented by the formula: Ar—X—. Examples of such substituent include halogen atoms (e.g., fluoro, chloro, bromo, iodo, etc.), optionally halogenated C$_{1-6}$ alkyl, optionally halogenated C$_{1-6}$ alkoxy, hydroxy, amino, etc. The "optionally halogenated C$_{1-6}$ alkyl" and the "Optionally halogenated C$_{1-6}$ alkoxy" are the same as those mentioned in detail above for the "optionally halogenated C$_1$ alkyl" and the "optionally halogenated C$_{1-6}$ alkoxy" for Ar.

In particular, as the substituent of ring A, halogen atom (e.g., chloro, etc.), C$_{1-6}$ alkoxy (e.g., methoxy, etc.) are preferred.

One to three such substituents may be substituted at the substitutable positions of ring A. When the number of the substituents is two or more, those substituents may be the same as or different from one another.

Ring A is preferable a benzene ring substituted by the group of the formula: A—X—.

In compound (I), any combination of each above-mentioned symbol can be appropriately used. Among them, the following combination is preferred.

(1) compound (I) wherein Ar is biphenylyl (e.g., 2-, 3- and 4-biphenylyl optionally substituted with halogen atom (in particular, chloro), X is [1] a group represented by the formula: —(CH$_2$)$_{p1}$O— (wherein p$^1$ is an integer of 1 to 3, preferably p$^1$ is 1), [2] —(CH$_2$)$_{p2}$— (wherein p$^2$ is an integer of 1 to 3), [3] —(CH$_2$)$^{p3}$OCONH— (wherein p$^3$ is an integer of 1 to 3, preferably $p^3$ is 1) [4] CONH or [5] SO$_2$NH, Y is a group represented by the formula: —(CH$_2$)$_{q1}$CONR$^9$(CH$_2$)$_{r1}$— (wherein each of $q^1$ and $r^1$ is an integer of 0 to 3 and their sum is an integer of not more than 3, R$^9$ is hydrogen atom or C$_{1-6}$ alkyl which may be halogenated or C$_{1-6}$ alkyl-carbonyl which may be halogenated), or a group represented by the formula: —(CH$_2$)$_{q2}$COO(CH$_2$)$_{r2}$— (wherein each of $q^2$ and $r^2$ is an integer of 0 to 3 and their sum is not more than 3) (preferably, Y is C$_{1-3}$ alkylene, a group represented by the formula: —CONH(CH$_2$)$_s$— (s is an integer of 1 to 3) or a group represented by the formula: —COO(CH$_2$)$_t$— (t is an integer of 1 to 3). In particular, $r^1$ and $r^2$ are preferably an integer of 1 to 3.

(2) compound (I) wherein Ar is C$_{6-14}$ aryl (in particular, phenyl, 1,2-naphthyl, etc.) or biphenylyl (e.g., 2-, 3- and 4-biphenylyl optionally substituted with halogen atom (in particular, chloro), X is [1] a group represented by the formula: —(CH$_2$)$_{p1}$O— (wherein $p^1$ is an integer of 1 to 3, preferably $p^1$ is 1), [2] —(CH$_2$)$_{p2}$— (wherein $p^2$ is an integer of 1 to 3), [3] —(CH$_2$)$_{p3}$OCONH— (wherein $p^3$ is an integer of 1 to 3, preferably $p^3$ is 1) [4] CONH or [5] SO$_2$NH, Y is a group represented by the formula: —(CH$_2$)$_{q1}$CONR$^9$(CH$_2$)$_{r1}$— (wherein each of $q^1$ and $r^1$ is an integer of 0 to 3 and their sum is an integer of not more than 3, R$^9$ is hydrogen atom or C$_{1-6}$ alkyl which may be halogenated or C$_{1-6}$ alkyl-carbonyl which may be halogenated), or a group represented by the formula: —(CH$_2$)$_{q2}$COO(CH$_2$)$_{r2}$— (wherein each of $q^2$ and $r^2$ is an integer of 0 to 3 and their sum is not more than 3) (preferably, Y is C$_{1-3}$ alkylene, a group represented by the formula: —CONH(CH$_2$)$_s$— (s is an integer of 1 to 3) or a group represented by the formula: —COO(CH$_2$)$_t$— (t is an integer of 1 to 3), each of R$^1$ and R$^2$ is [1] hydrogen atom or [2] C$_{1-6}$ alkyl (in particular C$_{1-3}$ alkyl such as methyl, ethyl, propyl, etc.) which may be substituted by carboxy, C$_{1-6}$ alkoxy-carbonyl (e.g., methoxycarbonyl, ethoxycarbonyl) or di-C$_{1-6}$ alkylnitrile (e.g., dimethylnitrile, diethylnitrile), or R$^1$ and R$^2$ form, together with the adjacent nitrogen atom, a 5- or 6-membered nitrogen-containing heterocyclic ring (e.g., piperidino, pyrolidin-1-yl, etc.), ring A is a benzene ring, or a 6-membered aromatic heterocyclic ring which may be substituted with halogen atom (e.g., chloro, etc.) and/or C$_{1-6}$ alkoxy (in particular, methoxy). Among them, $r^1$ and $r^2$ are preferably an integer of 1 to 3.

(3) compound (I) wherein Ar is C$_{6-14}$ aryl (in particular, phenyl, 1,2-naphthyl, etc.) or biphenylyl (e.g., 2-, 3- and 4-biphenylyl) optionally substituted with halogen atom (in particular chloro), etc., X is a group represented by the formula: —(CH$_2$)$_{p1}$O— (wherein $p^1$ is an integer of 1 to 3), —CONH—, —SO$_2$NH— or C$_{1-3}$ alkylene, Y is C$_{1-3}$ alkylene, a group represented by the formula: —CONH(CH$_2$)$_s$— (s is an integer of 1 to 3) or a group represented by the formula: —COO(CH$_2$)$_t$— (t is an integer of 1 to 3), each of R$^1$ and R$^2$ is hydrogen atom or C$_{1-6}$ alkyl (in particular, C$_{1-3}$ alkyl such as methyl, ethyl, propyl, etc.) or R$^1$ and R$^2$ form, together with the adjacent nitrogen atom, a 5- or 6-membered nitrogen-containing heterocyclic ring (e.g., piperidino, pyrolidin-1-yl, etc.), ring A is a benzene ring or a 6-membered aromatic heterocyclic ring which may be substituted with halogen atom (e.g., chloro, etc.) and/or C$_{1-6}$ alkoxy (in particular, methoxy). In particular, $r^1$ and $r^2$ are preferably an integer of 1 to 3.

Especially preferred compound (I) are
(1) 5-chloro-N-[2-N,N-diethylamino)ethyl]-2-methoxy-4-(1-naphthoylamino)benzamide,
(2) 5-chloro-N-[2-N,N-diethylamino)ethyl]-2-methoxy-4-(2-naphthoylamino)benzamide,
(3) 5-chloro-N-[2-N,N-diethylamino)ethyl]-2-methoxy-4-(1-naphthylsulfonylamino)benzamide,
(4) 5-chloro-N-[2-N,N-diethylamino)ethyl]-2-methoxy-4-(2-naphthylsulfonylamino)benzamide,
(5) N-[3-[4-(2-naphthylmethoxy)phenyl]propyl]-N,N-dipropyl-amine hydrochloride,
(6) N-[3-[4-[(2,4-dichlorobenzyl)oxy]phenyl]propyl]-N,N-di-propylamine hydrochloride,
(7) N-[4-(2-naphthylmethoxy)phenethyl]-N,N-dipropylamine hydrochloride,
(8) N-[4-(2,4-dichlorobenzyl)oxy]phenethyl]-N,N-dipropyl-amine hydrochloride,
(9) N-[4-(4-biphenylylmethoxy)phenethyl]-N,N-dipropylamine hydrochloride,
(10) N-[2-(2-naphthylmethoxy)phenethyl]-N,N-dipropylamine hydrochloride,
(11) N-[3-(2-naphthylmethoxy)phenethyl]-N,N-dipropylamine hydrochloride,
(12) N-[3-(4-biphenylylmethoxy)phenethyl]-N,N-dipropylamine hydrochloride,
(13) N-[3-[(2,4-dichlorobenzyl)oxy]phenethyl]-N,N-dipropylamine hydrochloride,
(14) N-[3-(1-naphthylmethoxy)phenethyl]-N,N-dipropylamine hydrochloride,
(15) 4-(4-biphenylylmethoxy)phenyl-N-(2-piperidinoethyl) acetamide,
(16) 4-(4-biphenylylmethoxy)phenyl-N-[2-(N,N-dimethylamino)ethyl]acetamide,
(17) 6-(4-biphenylylmethoxy)-N-[2-(pyrrolidine-1-yl)ethyl] nicotinamide,
(18) 1-(4-biphenylylmethyl)-1,6-dihydro-6-oxo-N-[2-(pyrrolidine-1-yl)ethyl]-3-pyridinecarboxamide,
(19) 1-(4-biphenylylmethyl)-1,6-dihydro-6-oxo-N-(2-(piperidinoethyl)-3-pyridinecarboxamide,
(20) 6-(4-biphenylylmethoxy)-N-(2-piperidinoethyl)-nicotinamide,
(21) 6-(4-biphenylylmethoxy)-N-[2-(N,N-dimethylamino) ethyl]nicotinamide,
(22) 4-(4-biphenylylmethoxy)-N-(2-piperidinoethyl) benzamide,
(23) 4-(4-biphenylylmethoxy)-N-[(2-pyrrolidine-1-yl)ethyl] benzamide,
(24) 2-piperidinoethyl=4-(4-biphenylylethoxy)benzoate,
(25) 2-(pyrrolidin-1-yl)ethyl=4-(4-biphenylylmethoxy) benzoate,
(26) 4-[4-(biphenylylmethoxy)phenyl]-N-[2-(N,N-dimethylamino)ethyl]acetamide oxalate,
(27) 4-[4-(biphenylylmethoxy)phenyl]-N-[2-(N,N-dimethylamino)ethyl]acetamide maleate,
(28) 4-[4-(biphenylylmethoxy)phenyl]-N-[2-(N,N-dimethylamino)ethyl]acetamide fumarate,
(29) 4-[4-(biphenylylmethoxy)phenyl]-N-[2-(N-methylamino)-ethyl]acetamide hydrochloride,
(30) 4-[4-(biphenylylmethoxy)phenyl]-N-[2-(N-methylamino)-ethyl]acetamide,
(31) ethyl 7-[2-[4-[(4-biphenylylmethoxy)phenyl] acetylaminoethyl](methyl)amino]heptanoate,
(32) 7-[2-[4-[4-(biphenylylmethoxy)phenyl] acetylaminoethyl](methyl)amino]heptanoic acid hydrochloride,
(33) N-(4-(2-((2-(dimethylamino)ethyl)(methyl)amino)-2-oxoethyl)phenyl)[1,1'-biphenyl]-4-carboxamido,
(34) N-(2-aminoethyl)-2-(4-([1,1'-biphenyl]-4-ylmethoxy) phenyl)acetamide hydrochloride,
(35) 4-([1,1'-biphenyl]-4-ylmethoxy)-N-(2-(1-pyrrolidinyl) ethyl)benzamide,
(36) N-[4-({[2-(diethylamino)ethyl]amino}carbonyl) phenyl]-(4-biphenylyl)carboxamide,

(37) 4-(4-biphenylyl)methoxy-N-[2-(isopropylamino) ethyl]benzamide,
(38) 2-(N,N-diethylamino)ethyl-4-[(4-biphenylyl)carbonyl]-amino]benzoate,
(39) N-[4-({[2-(dimethylamino)ethyl]amino}carbonyl) phenyl]-(4-biphenylyl)carboxamide,
(40) N-[4-{[2-(piperidinoethyl)amino]carbonyl}phenyl](4-biphenylyl)carboxamide, or
(41) N-[4-({[2-(pyrrolidinyl)ethyl]amino}carbonyl) phenyl]-(4-biphenylyl)carboxamide, etc.

Among them, preferred compounds are
[1] 5-chloro-N-[2-N,N-diethylamino)ethyl]-2-methoxy-4-(1-naphthoylamino)benzamide,
[2] 5-chloro-N-[2-N,N-diethylamino)ethyl]-2-methoxy-4-(2-naphthoylamino)benzamide,
[3] 5-chloro-N-[2-N,N-diethylamino)ethyl]-2-methoxy-4-(1-naphthylsulfonylamino)benzamide,
[4] 5-chloro-N-[2-N,N-diethylamino)ethyl]-2-methoxy-4-(2-naphthylsulfonylamino)benzamide,
[5] 6-(4-biphenylylmethoxy)-N-(2-piperidinoethyl) nicotinamide,
[6] 6-(4-biphenylylmethoxy)-N-[2-(N,N-dimethylamino) ethyl]nicotinamide,
[7] 4-(4-biphenylylmethoxy)-N-(2-piperidinoethyl) benzamide,
[8] 4-(4-biphenylylmethoxy)-N-[(2-pyrrolidine-1-yl)ethyl] benzamide, etc.

In the above-mentioned compound (I), the compound represented by the formula (Ia) is a novel compound.

In the formula, examples of the aromatic ring assembly group which may be substituted represented by Ar' include the same aromatic ring assembly which may be substituted as defined with respect to the above Ar', in particular, biphenylyl (e.g., 2-, 3- or 4-biphenylyl, etc.).

Examples of X' include [1] a group represented by the formula: —(CH$_2$)$_{p1}$O— (wherein p$^1$ is an integer of 1 to 3), [2] —(CH$_2$)$_{p2}$— (wherein p2 is an integer of 1 to 3) or [3] CONH, etc. in particular, —(CH$_2$)$_{p1}$O— (wherein p$^1$ is as defined above), etc. Preferably, p$^1$ is 1 or 2, in particular, 1 is preferred. Preferably, p$^2$ is 1 or 2, in particular, 1 is preferred.

Examples of Y' include [1] a group represented by the formula: —(CH$_2$)$_{q1}$CONR$^9$(CH$_2$)$_{r1}$— (wherein each of q$^1$ and r$^1$ is an integer of 0 to 3 and their sum is an integer of not more than 3, R$^9$ is hydrogen atom or C$_{1-6}$ alkyl which may be halogenated or C$_{1-6}$ alkyl-carbonyl which may be halogenated), or [2] a group represented by the formula: —(CH$_2$)$_{q2}$COO(CH$_2$)$_{r2}$— (wherein each of q$^2$ and r$^2$ is an integer of 0 to 3 and their sum is not more than 3), etc., in particular, a group represented by the formula: —(CH$_2$)$_{q1}$CONR$^9$(CH$_2$)$_{r1}$— (wherein each symbol is as defined above), etc.

Preferably, q$^1$ and q$^2$ are 0 or 1, in particular, 0 is preferred.

Preferably, r$^1$ and r$^2$ are an integer of 1 to 3, more preferably, 1 or 2. In particular, 1 is preferred.

The C$_{1-6}$ alkyl represented by R$^1$ and R$^2$ includes, for example, methyl, ethyl, propyl, isopropyl, butyl, isobutyl, sec-butyl, tert-butyl, pentyl, hexyl, etc. In particular, methyl, ethyl, propyl, etc. are preferred.

Preferred example of R$^9$ include hydrogen atom, C$_{1-3}$ alkyl which may be halogenated (in particular, methyl, ethyl, etc.) or C$_{1-3}$ alkyl-carbonyl (in particular, acetyl, etc.). Hydrogen atom is particularly preferred.

Preferred examples of R$^1$ and R$^2$ include [1] hydrogen atom or [2] C$_{1-6}$ alkyl (in particular, C$_{1-3}$ alkyl such as methyl, ethyl, propyl, etc.) which may be substituted by carboxy, C$_{1-6}$ alkoxy-carbonyl (e.g., methoxycarbonyl, ethoxycarbonyl) or di-C$_{1-6}$ alkylnitrile (e.g., dimethynitrile, diethylnitrile), or R$^1$ and R$^2$ form, together with the adjacent nitrogen atom, a 5- or 6-membered nitrogen-containing heterocyclic ring.

Preferred examples of ring A include a benzene ring or a 6-membered nitrogen-containing aromatic heterocyclic ring, preferably a benzene ring, a pyridine ring or 2-pyridone ring, in particular, a benzene ring or a pyridine ring.

Preferred examples of compound (Ia) include that wherein Ar' is biphenylyl (e.g., 2-, 3- and 4-biphenylyl), X' is [1] a group represented by the formula: —(CH$_2$)$^{p1}$O— (wherein p$^1$ is an integer of 1 to 3), [2] —(CH$_2$)$^{p2}$— (wherein p$^2$ is an integer of 1 to 3) or [3] CONH, Y' is [1] a group represented by the formula: —(CH$_2$)$_{q1}$CONR$^9$ (CH$_2$)$_{r1}$— (wherein each of q$^1$ and r$^1$ is an integer of 0 to 3 and their sum is an integer of not more than 3, R$^9$ is hydrogen atom or C$_{1-6}$ alkyl (in particular, C$_{1-3}$ alkyl) which may be halogenated or C$_{1-6}$ alkyl-carbonyl (in particular, C$_{1-3}$ alkyl-carbonyl such as acetyl, ethylcarbonyl, etc.) which may be halogenated), or a group represented by the formula: —(CH$_2$)$_{q2}$COO(CH$_2$)$_{r2}$— (wherein each of q$^2$ and r$^2$ is an integer of 0 to 3 and their sum is not more than 3), each of R$^1$ and R$^2$ is [1] hydrogen atom or [2] C$_{1-6}$ alkyl (in particular C$_{1-3}$ alkyl such as methyl, ethyl, propyl, etc.) which may be substituted by carboxy, C$_{1-6}$ alkoxy-carbonyl (e.g., methoxycarbonyl, ethoxycarbonyl) or di-C$_{1-6}$ alkylnitrile (e.g., dimethylnitrile, diethylnitrile), or R$^1$ and R$^2$ form, together with the adjacent nitrogen atom, a 5- or 6-membered nitrogen-containing heterocyclic ring (e.g., piperidino, pyrrolidin-1-yl, etc.), ring A is a benzene ring or a 6-membered aromatic heterocyclic ring (in particular, a pyridine ring, 2-pyridone ring).

Further, preferred examples of compound (Ia) include that wherein Ar is biphenylyl, X is —(CH$_2$)$_p$O, Y is —CONH (CH$_2$)$_s$— (s is an integer of 1 to 3), each of R$^1$ and R$^2$ is C$_{1-3}$ alkyl (in particular, methyl, ethyl, propyl, etc.), or R$^1$ and R$^2$ form, together with the adjacent nitrogen atom, a 5- or 6-membered nitrogen-containing heterocyclic ring (e.g., piperidino, pyrrolidin-1-yl, etc.), ring A is a benzene ring or a 6-membered aromatic heterocyclic ring (in particular, a pyridine ring, 2-pyridone ring, etc.) which may be substituted with halogen atom (e.g., chloro, etc.) and/or C$_{1-6}$ alkoxy (in particular, methoxy).

More specifically, preferred examples of compound (Ia) include, in particular,
(1) 4-(4-biphenylylmethoxy)phenyl-N-(2-piperidinoethyl) acetamide,
(2) 4-(4-biphenylylmethoxy)phenyl-N-[2-(N,N-dimethylamino)ethyl]acetamide,
(3) 6-(4-biphenylylmethoxy)-N-[2-(pyrrolidine-1-yl)ethyl]-nicotinamide,
(4) 1-(4-biphenylylmethyl)-1,6-dihydro-6-oxo-N-[2-(pyrrolidine-1-yl)ethyl]-3-pyridinecarboxamide,
(5) 1-(4-biphenylylmethyl)-1,6-dihydro-6-oxo-N-(2-(piperidinoethyl)-3-pyridinecarboxamide,
(6) 6-(4-biphenylylmethoxy)-N-(2-piperidinoethyl) nicotinamide,
(7) 6-(4-biphenylylmethoxy)-N-[2-(N,N-dimethylamino) ethyl]nicotinamide,
(8) 4-(4-biphenylylmethoxy)-N-(2-piperidinoethyl) benzamide,
(9) 4-(4-biphenylylmethoxy)-N-[(2-pyrrolidine-1-yl)ethyl] benzamide,
(10) 2-piperidinoethyl=4-(4-biphenylylethoxy)benzoate
(11) 2-(pyrrolidin-1-yl)ethyl=4-(4-biphenylylmethoxy) benzoate

(12) 4-[4-(biphenylylmethoxy)phenyl]-N-[2-(N,N-dimethylamino)ethyl]acetamide oxalate,
(13) 4-[4-(biphenylylmethoxy)phenyl]-N-[2-(N,N-dimethylamino)ethyl]acetamide maleate,
(14) 4-[4-(biphenylylmethoxy)phenyl]-N-[2-(N,N-dimethylamino)ethyl]acetamide fumarate,
(15) 4-[4-(biphenylylmethoxy)phenyl]-N-[2-(N-methylamino)ethyl]acetamide hydrochloride,
(16) 4-[4-(biphenylylmethoxy)phenyl]-N-[2-(N-methylamino)ethyl]acetamide
(17) ethyl 7-[2-[4-[(4-biphenylylmethoxy)phenyl]acetylaminoethyl](methyl)amino]heptanoate,
(18) 7-[2-[4-[4-(biphenylylmethoxy)phenyl]acetylaminoethyl](methyl)amino]heptanoic acid hydrochloride,
(19) N-(4-(2-((2-(dimethylamino)ethyl)(methyl)amino)-2-oxoethyl)phenyl)[1,1'-biphenyl]-4-carboxamide,
(20) N-(2-aminoethyl)-2-(4-([1,1'-biphenyl]-4-ylmethoxy)phenyl)acetamide hydrochloride,
(21) 4-([1,1'-biphenyl]-4-ylmethoxy)-N-(2-(1-pyrrolidinyl)ethyl)benzamide
(22) N-[4-({[2-(diethylamino)ethyl]amino}carbonyl)phenyl]-(4-biphenylyl)carboxamide,
(23) 4-(4-biphenylyl)methoxy)-N-[2-(isopropylamino)ethyl]benzamide
(24) 2-(N,N-diethylamino)ethyl-4-[(4-biphenylyl)carbonyl]amino]benzoate
(25) N-[4-({[2-(dimethylamino)ethyl]amino}carbonyl)phenyl]-(4-biphenylyl)carboxamide,
(26) N-[4-{[2-(piperidinoethyl)amino]carbonyl}phenyl](4-biphenylyl)carboxamide,
(27) N-[4-({[2-(pyrrplidinyl)ethyl]amino}carbonyl)phenyl]-(4-biphenylyl)carboxamide, etc.

Among them, preferred compounds are
[1] 6-(4-biphenylylmethoxy)-N-(2-piperidinoethyl)nicotinamide,
[2] 6-(4-biphenylylmethoxy)-N-[2-(N,N-dimethylamino)ethyl]nicotinamide,
[3] 4-(4-biphenylylmethoxy)-N-(2-piperidinoethyl)benzamide,
[4] 4-(4-biphenylylmethoxy)-N-[(2-pyrrolidine-1-yl)ethyl]benzamide, etc.

As the salts of compound (I) and compound (Ia), for example, inorganic salts, ammonium salts, salts with organic bases, salts with inorganic acids, salts with organic acids and salts with basic or acidic amino acids can be mentioned.

Preferable examples of inorganic salts include alkali metal salts such as sodium salt and potassium salt; alkaline earth metal salts such as calcium salts, magnesium salts and barium salts; aluminum salts, etc. Preferred salts with organic bases are exemplified by salts with trimethylamine, triethylamine, pyridine, picoline, ethanolamine, diethanolamine, triethanolamine, dicyclohexylamine, N,N'-dibenzylethylenediamine, etc. Preferred salts with inorganic acids are exemplified by salts with hydrochloric acid, hydrobromic acid, nitric acid, sulfuric acid, phosphoric acid, etc. Preferred salts with organic acids are exemplified by salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferred salts with basic amino acids are exemplified by salts with arginine, lysine, ornithine, etc. Preferred salts with acidic amino acids are exemplified by salts with aspiartic acid, glutamic acid, etc.

Among others, pharmaceutically acceptable salts are preferable. Preferable examples include, for example, when compound (I) or (Ia) has an acidic functional group, alkali metal salts (e.g., sodium salt, potassium salt, etc.), alkaline earth metal salts (e.g., calcium salt, magnesium salt, barium salt, etc.), and ammonium salts; and when compound (I) or (Ia) has a basic functional group, inorganic salts such as hydrochloride, sulfate, phosphate and hydrobromide, or, organic salts such as acetate, maleate, fumarate, succinate, methanesulfonate, p-toluenesulfonate, citrate and tartrate.

A prodrug of compound (I), compound (Ia) or its salt (hereinafter referred to as the compound of the present invention) may be a compound that is converted into the compound of the present invention by a reaction with an enzyme, gastric acid, or the like under physiological conditions in the living body, namely, a compound that is converted into the compound of the present invention by an enzymatic oxidation, reduction, hydrolysis, or the like, and a compound that is converted into the compound of the present invention by hydrolysis with gastric acid or the like.

Examples of a prodrug of the compound of the present invention include a compound wherein an amino group in the compound of the present invention is acylated, alkylated, phosphorylated, (e.g., a compound wherein an amino group in the compound of the present invention is converted into eicosanoylamino, alanylamino, pentylaminocarbonylamino, (5-methyl-2-oxo-1,3-dioxorene-4-yl)methoxycarbonylamino, tetrahydrofuranylamino, pyrrolidylmethylamino, pivaloyloxymethylamino, tert-butylamino, etc.); a compound wherein an hydroxy group in the compound of the present invention is acylated, alkylated, phosphorylated, or converted into borate (e.g., a compound wherein hydroxy group in the compound of the present invention is converted into acetyloxy, palmitoyloxy, propanoyloxy, pivaloyloxy, succinyloxy, fumaryloxy, alanyloxy, or dimethylaminomethylcarbonyloxy, etc.); a compound wherein carboxy group of the compound of the present invention is ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxoren-4-yl)methyl esterification, cyclohexyloxycarbonyl esterification, or conversion into methyl amide), etc. These compounds can be produced from the compound of the present invention according to any per se known method.

Further, a prodrug of the compound of the present invention may be a compound that is converted into the compound of the present invention under physiological conditions as described in "Development of Drugs", Volume 7, Molecular Design, Hirokawa Shoten, 1990; pages 163–198.

Further, compound (I) or (Ia) may be either anhydride or hydrate and, in case of a hydrate, it may have 1 to 3 $H_2O$ molecules.

Process for producing compound (Ia) will be explained below.

The compound (Ia) can be produced by using any per se known means. For example, the compound (Ia) wherein X contains oxygen atom, optionally oxidized sulfur atom or optionally substituted imino can be produced by the following process. Normally, "room temperature" is 0 to 30° C.

Each symbol disclosed in the following schemes is as defined above unless otherwise stated.

[Process 1]

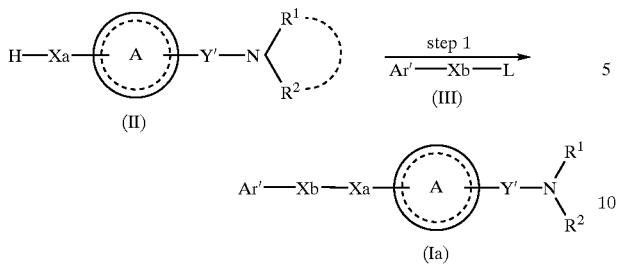

wherein Xa is oxygen atom, optionally oxidized sulfur atom or optionally substituted imino. The "optionally substituted imino" represented by Xa is the same group as "optionally substituted imino" of the above $R^8$.

(Step 1)

The Compound (II) is subjected to alkylation or acylation to obtain the compound (Ia).

The "alkylation" and "acylation" may be effected in any per se known manner, for example, according to the methods described in Organic Functional Group Preparations, 2nd Ed., Academic Press Inc., 1989.

Specifically, the compound (II) is reacted with a compound of the formula: Ar'-Xb-L (III): wherein Xb represents a group formed by removing Xa from X', and L represents a leaving group or a hydroxy, to obtain the compound (Ia)

The leaving group for L includes, for example, halogen atoms (e.g., chloro, bromo, iodo, etc.), optionally halogenated $C_{1-6}$ alkylsulfonyloxy (e.g., methanesulfonyloxy, ethanesulfonyloxy, trifluoromethanesulfonyloxy, etc.), $C_{6-10}$ arylsulfonyloxy which may be substituted, etc.

The "substituent" for the "$C_{6-10}$ arylsulfonyloxy which may be substituted" includes, for example, 1 to 3 substituents selected from the group consisting of halogen atoms, optionally halogenated $C_{1-6}$ alkyl and optionally halogenated $C_{1-6}$ alkoxy. Specific examples of the "$C_{6-10}$ arylsulfonyloxy which may be substituted" are benzenesulfonyloxy, p-toluenesulfonyloxy, 1-naphthalenesulfonyloxy, 2-naphthalenesulfonyloxy, etc.

In the case that L is a leaving group, for example, the compound (II) is reacted with an equivalent amount or an excessive amount of the compound (III) in an inert solvent. If desired, a base is added to the reaction system. Where Xa is optionally substituted imino, the addition of the base is not always indispensable.

The reaction temperature falls between −20° C. and 100° C., preferably between room temperature and 80° C. The reaction time falls between 0.5 hours and 1 day.

The inert solvent includes, for example, alcohols, ethers, halogenated hydrocarbons, aromatic solvents, nitriles, amides, ketones, sulfoxides, water, etc., which may be used either singly or as a suitable mixture of two or more species. Of those, preferred are acetonitrile, N,N-dimethylformamide (DMF), acetone, ethanol, pyridine, etc.

The "base" includes, for example;

(1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethylsilazide, sodium hexamethylsilazide, potassium hexamethylsilazide, etc.), alkali metal or alkaline earth metal lower-alkoxides (e.g., sodium methoxide, sodium ethoxide, potassium tert-butoxide, etc.), etc.;

(2) inorganic bases such as alkali metal or alkaline earth metal hydroxides (e.g., sodium hydroxide, potassium hydroxide, lithium hydroxide, barium hydroxide, etc.), alkali metal or alkaline earth metal carbonates (e.g., sodium carbonate, potassium carbonate, cesium carbonate, etc.), alkali metal or alkaline earth metal hydrogencarbonates (e.g., sodium hydrogencarbonate, potassium hydrogencarbonate, etc.), etc.; or (3) organic bases such as amines e.g., triethylamine, diisopropylethylamine, N-methylmorpholine, dimethylaminopyridine, DBU (1,8-diazabicyclo[5.4.0]-7-undecene), DBN (1,5-diazabicyclo[4.3.0]non-5-ene), etc., basic heterocyclic compounds, e.g., pyridine, imidazole, 2,6-lutidine, etc.

Preferably, the alkylation is effected by stirring the compound (II) with 1 to 2 equivalents of the compound (III) and 1 to 5 equivalents of a base (e.g., potassium carbonate, sodium hydride, sodium hydroxide, etc.), in acetonitrile or DMF, for 1 hour to 2 days. The preferred reaction temperature varies, depending on the base used. For example, when sodium hydride is used, the reaction temperature is preferably room temperature; and when potassium carbonate is used, the preferred reaction temperature falls between room temperature and 80° C.

The acylation is preferably effected by stirring the compound (II) with 1 to 1.5 equivalents of the compound (III) and 1 to 5 equivalents of a base (e.g., sodium hydride, sodium hydroxide, potassium carbonate, sodium hydrogencarbonate, triethylamine, etc.), in an inert solvent (e.g., single or mixed solvent of water, ethyl acetate, DMF, acetonitrile and/or pyridine), at room temperature for 1 to 6 hours.

In the case that L is a hydroxy group, the compound (II) is subjected to Mitsunobu reaction.

The Mitsunobu reaction may be attained, for example, by stirring the compound (II) with 1 to 3 equivalents, preferably from 1.1 to 2 equivalents of the compound (III) in the presence of 1 to 2 equivalents of a triarylphosphine (e.g., triphenylphosphine, etc.) and 1 to 2 equivalents of DEAE (diethyl azodicarboxylate) in an inert solvent, for 1 to 24 hours.

The inert solvent includes, for example, ethers, etc. Preferred is tetrahydrofuran (THF).

The compound wherein Y' is —(CH$_2$)$_q$CONR$_9$(CH2)$_r$— can be produced by reacting a carboxylic acid derivative (IV) with an amine (V) according to the amidation according to the following process 2.

[Process 2]

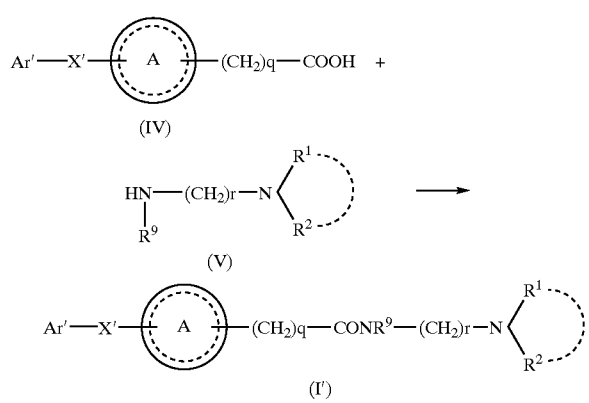

wherein each symbol is as defined above.

(Step 2)

The "amidation" may be effected in any per se known methods, for example, (1) by reacting the compound (IV) with amine (V) in the presence of a dehydrating condensing agent, or (2) by reacting a reactive derivative of compound (IV) with amine (V).

In the above reaction (1), the compound (IV) is reacted with 1 to 5 equivalents of amine (v) in the presence of 1 to 2 equivalents of a dehydrating condensing agent, in an inert solvent, at room temperature, for 10 to 24 hours. If desired, 1 to 1.5 equivalents of 1-hydroxybenzotriazole (HOBT) and/or 1 to 5 equivalents of a base (e.g., triethylamine, etc.) may be added to the reaction system.

The "dehydrating condensing agent" includes, for example, dicyclohexylcarbodiimide (DCC), 1-ethyl-3-(3-dimethylaminopropyl) carbodiimide hydrochloride (WSC), etc. Of those, preferred is WSC.

The inert solvent includes, for example, nitrites (preferably, acetonitrile), amides (preferably, DMF), halogenated hydrocarbons (preferably, dichloromethane), ethers (preferably, THF), etc., which may be used either singly or as a suitable mixture of two or more species.

In the above reaction (2), a reactive derivative of the compound (IV) is reacted with 1 to 5 equivalents, preferably 1 to 3 equivalents of amine (V) in an inert solvent at, normally, −20 to 50° C., preferably at room temperature, for 5 minutes to 40 hours, preferably 1 to 18 hours. If desired, 1 to 10 equivalents, preferably 1 to 3 equivalents of a base may be in the reaction system.

The "reactive derivative" of the compound (IV) includes, for example, its acid halides (e.g., acid chlorides, acid bromides, etc.), mixed acid anhydrides (e.g., acid anhydrides with $C_{1-6}$ alkyl-carboxylic acids, $C_{6-10}$ aryl-carboxylic acids or $C_{1-6}$ alkyl-carbonic acids, etc.), and active esters (e.g., esters with $C_{1-6}$ alcohols [e.g., methanol, ethanol, 2-propanol, 1-propanol, 1-butanol, etc.], phenol which may be substituted, 1-hydroxybenzotriazole or N-hydroxysuccinimide, etc.).

The "substituent" for the "phenol which may be substituted" includes, for example, 1 to 5 substituents selected from the group consisting of halogen atoms, nitro, optionally halogenated $C_{1-6}$ alkyl and optionally halogenated $C_{1-6}$ alkoxy. Specific examples of the "phenol which may be substituted" are phenol, pentachlorophenol, pentafluorophenol, p-nitrophenyl, etc. The reactive derivatives are preferably acid halides.

The "base" is the same as those mentioned in detail hereinabove for the step 1. Preferred are potassium carbonate, sodium carbonate, sodium hydroxide, potassium hydroxide, sodium hydrogencarbonate, potassium hydrogencarbonate, sodium alkoxides (e.g., sodium methoxide, sodium ethoxide, sodium butoxide, etc.), organic amines (e.g., triethylamine, pyridine, triazole, imidazole, hydroxy pyridine, etc.). The inert solvent includes, for example, alcohols, ethers, halogenated hydrocarbons, aromatic solvents, nitrites, amides, ketones, sulfoxides, water, etc., which may be used either singly or as a suitable mixture of two or more species. Of those, preferred are methanol, ethanol, acetonitrile, dichloromethane, chloroform, etc.

In the case of an active ester, for example, the ester (preferably, methyl ester or ethyl ester) is reacted with 1 to 5 equivalents of amine (V) together with catalytic amount to 2 equivalents of an organic amine (e.g., triethylamine, pyridine, triazole, imidazole, hydroxy pyridine, etc.) in an inert solvent.

The reaction temperature falls between room temperature and under refluxing (preferably 50 to 120° C.). The preferred reaction time falls between 1 and 60 hours. As the inert solvent, alcohols (e.g., methanol, ethanol, etc.) can be used.

Carboxylic acid (IV) and amine (V) used in the reaction are commercially available or can be easily available. For example, the benoziic acid derivative can be produced by the process described in WO93/24442, etc.

Compound (I') thus obtained can be converted into the compound (I) by any per se known reaction such as hydrolysis, esterification, amidation, oxidation, reduction and the following deprotection reaction, or combination thereof.

The above "alcohols" includes, for example, methanol, ethanol, isopropanol, tert-butanol, etc. The above "ethers" includes, for example, ethyl ether, tetrahydrofuran (THF), 1,4-dioxane, 1,2-dimethoxyethane, etc. The above "halogenated hydrocarbons" includes, for example, dichloromethane, chloroform, 1,2-dichloroethane, carbon tetrachloride, etc. The above "aromatic solvents" includes, for example, benzene, toluene, xylene, pyridine, etc. The above "hydrocarbons" includes, for example, hexane, pentane, cyclohexane, etc. The above "amides" includes, for example, N,N'-dimethylformamide (DMF), N,N'-dimethylacetamide, N-methylpyrrolidone, etc. The above "ketones" includes, for example, acetone, methyl ethyl ketone, etc. The above "sulfoxides" includes, for example, dimethylsulfoxide (DMSO), etc. The above "nitrites" includes, for example, acetonitrile, propionitrile, etc.

In the above-mentioned reactions where the starting compounds have any of amino, carboxy, hydroxy or carbonyl as their substituents, those groups may be protected by ordinary protective groups which are generally used in peptide chemistry. The protective groups may be removed after the reaction to give the objective products.

The amino-protecting group includes, for example, formyl, $C_{1-6}$ alkyl-carbonyl (e.g., acetyl, propionyl, etc.), $C_{1-6}$ alkyloxy-carbonyl (e.g., methoxycarbonyl, ethoxycarbonyl, t-butoxycarbonyl, etc.), benzoyl, $C_{7-10}$ aralkyl-carbonyl (e.g., benzylcarbonyl, etc.), $C_{7-14}$ aralkyloxy-carbonyl (e.g., benzyloxycarbonyl, 9-fluorenylmethoxycarbonyl, etc.), trityl, phthaloyl, N,N-dimethylaminomethylene, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkoxy (e.g., methoxy, ethoxy, propoxy, etc.) or nitro, etc.

The carboxy-protecting group includes, for example, $C_{1-6}$ alkyl (e.g., methyl, ethyl, propyl, isopropyl, butyl, tert-butyl, etc.), $C_{7-11}$ aralkyl (e.g., benzyl, etc.), phenyl, trityl, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkoxy (e.g., methoxy, ethoxy, propoxy, etc.) or nitro, etc.

The hydroxy-protecting group includes, for example, $C_{1-6}$ alkyl (e.g., methyl, ethyl, propyl, isopropyl, butyl, tert-butyl, etc.), phenyl, trityl, $C_{7-10}$ aralkyl (e.g., benzyl, etc.), formyl, $C_{1-6}$ alkyl-carbonyl (e.g., acetyl, propionyl, etc.), benzoyl, $C_{7-10}$ aralkyl-carbonyl (e.g., benzylcarbonyl, etc.), 2-tetrahydropyranyl, 2-tetrahydrofuranyl, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkyl (e.g., methyl, ethyl, propyl, etc.), $C_{1-6}$ alkoxy (e.g., methoxy, ethoxy, propoxy, etc.) or nitro, etc.

The carbonyl-protecting group includes, for example, cyclic acetals (e.g., 1,3-dioxorane, etc.), acyclic acetals (e.g., di-$C_{1-6}$ alkylacetals, etc.), etc.

Those protective groups may be removed by any per se known methods, for example, the methods described in Protective Groups in Organic Synthesis, published by John Wiley and Sons, 1980, etc. For example, the method of removing these protective groups, includes the methods using acids, bases, ultraviolet ray, hydrazine, phenylhydrazine, sodium N-methyldithiocarbamate, tetrabutylammonium fluoride, palladium acetate, etc.; and reduction, etc.

Compound (Ia) can be isolated and purified by any known procedures, for example, through solvent extraction, pH adjustment, redistribution, crystallization, recrystallization, chromatography, etc. The starting compounds and their salts for the compound (Ia) can also be isolated and purified according to the same known procedures as above, but without any isolation procedure, they may be used in the next step while they are in reaction mixtures.

Where the compound (Ia) includes optical isomers, stereoisomers, regio isomers and rotational isomers, those are within the scope of the compound (Ia), and can be isolated as their single compound through per se known synthesis or separation. For example, where optical isomers of the compound (Ia) exist, those resolved from their mixtures through optical resolution are within the scope of the compound (Ia).

The optical isomers can be produced in any per se known manner. Specifically, optically active synthetic intermediates or mixtures of racemate of the final product are subjected to ordinary optical resolution to give the corresponding optical isomers.

For the optical resolution, employable are any per se known methods, such as a fractional recrystallization method, a chiral column method, a diastereomer method, etc.

1) Fractional Recrystallization

The method which comprises allowing a tracemate to react with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to, give a salt, which is then isolated through fractional recrystallization, followed by, when desired, subjecting the isolated compound to neutralization to obtain free optical isomers.

2) Chiral Column Method

The method of separating a racemate or a salt thereof, which comprises utilizing a column for fractionating optical isomers (chiral column). In the case of liquid column chromatography, for example, a mixture of optical isomers is applied to a chiral column, such as ENANTIO-OVM (manufactured by Tosoh Corp.), CHIRAL SERIES (manufactured by Daicel Co.), etc., which is then eluted with water, various buffers (e.g., phosphate buffer) and organic solvents (e.g., ethanol, methanol, isopropanol, acetonitrile, trifluoroacetic acid, diethylamine, etc.), singly or a suitable mixture of them, to isolate the individual optical isomers. In case of gas chromatography, for example, a chiral column such as CP-Chirasil-DeX CB (manufactured by GL Science Co.), etc. is used for the fractionation.

3) Diastereomer Method

A racemic mixture is chemically reacted with an optically-active reagent to give a mixture of diastereomer, which is subjected to ordinary separation (e.g., fractional recrystallization, chromatography, etc.) to give single compounds. The thus-isolated single compounds are then chemically processed, for example, through hydrolysis to thereby remove the optically-active reagent site from the compounds to obtain optical isomers. For example, where the compound (I) has a hydroxy group or a primary or secondary amino group in the molecule, it is fused with an optically-active organic acid (e.g., MPTA [α-methoxy-α-(trifluoromethyl) phenyl-acetic acid], (−)-menthoxyacetic acid, etc.) or the like to give the corresponding ester-type or amide-type diastereomer. On the other hand, where the compound (I) has a carboxylic acid group, it is fused with an optically-active amine or alcohol reagent to give the corresponding amide-type or ester-type diastereomer. The thus-isolated diastereomer is then subjected to acidic or basic hydrolysis, through which it is converted into the optical isomer of the original compound.

Compound (I) or a salt thereof can be produced according to the above process for producing the compound (Ia) or a salt thereof, or can be producing by any per se known method or its modification.

Compound (I) has an excellent inhibitory activity of amyloid-β protein (Aβ1-40, Aβ1-41, Aβ-42 and/or Aβ1-43, in particular Aβ1-40 and/or Aβ1-42) the production and/or secretion and thus is effective in preventing and/or treating diseases caused by amyloid-β protein. Compound (Ia) also has the inhibitory activity for the amyloid-β protein production and/or secretion.

In addition, the compound (I) has low toxicity. In particular, the compound obtained in Example 8 hereinafter shows excellent penetration in brain.

Therefore, compounds (I) are useful as safe medicines for preventing and/or treating diseases caused by amyloid-β protein, in particular, the production and/or secretion of amyloid-β protein in mammals (e.g., rat, mouse, guinea pig, rabbit, sheep, horse, pig, cattle, monkey, human being, etc.).

Examples of the diseases include senile dementia, Alzheimer's disease, Down's syndrome, Parkinson's disease, disease, amyloid angiopathy and disorders caused by amyloid-β protein in cerebrovascular disorders. Among others, the compound (I) is suitable for Alzheimer's disease.

Compound (I) can be formulated into pharmaceutical compositions by any per se known means. Directly or after mixing with suitable amounts of any desired, pharmaceutically-acceptable carriers in any per se known formulation processes, the compound (I) can be safely administered in the form of tablets (including sugar-coated tablets, film-coated tablets), powders, granules, capsules (including soft capsules), liquids, injections, suppositories, sustained release preparations, etc., either orally or non-orally (for example, topically, rectally, intravenously, etc.).

In the pharmaceutical composition of the present invention, the amount of the compound (I) is about 0.1 to 100% by weight of the total weight of the composition. The dose of the composition varies depending on the subject to which the composition is administered, the administration route employed, the disorder of the subject, etc. For example, for the peroral composition for treating Alzheimer's disease, its dose may be about 0.1 to 500 mg/adult (weighing about 60 kg) or so, preferably about 1 to 100 mg/adult or so, more preferably 5 to 100 mg/adult or so, in terms of the active ingredient [compound (I)], and this may be administered once or several times a day.

Any ordinary organic and inorganic carrier substances that are generally used in formulating medicines are usable as the carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

The present invention is further illustrated in detail by the following Reference Examples, Examples and Experimental Examples, but they are merely examples, which are not intended to limit the present invention and may be varied without departing from the scope of the present invention.

"Room temperature" in the following Reference Examples and Examples usually indicates about 0 to about 30° C. For drying an organic solvent, magnesium sulfate anhydride or sodium sulfate anhydride was used. Unless otherwise stated, % indicates the percent by weight.

IR spectra were measured by diffused reflection method with Fourier-transform IR spectrophotometer.

Other symbols used in the present text indicate the following meanings.

s: singlet
d: doublet
t: triplet
q: quartet
m: multiplet
br: broad
dd: doublet of doublets
J: coupling constant
Hz: Hertz
CDCl$_3$: deuterated chloroform
$^1$H-NMR: proton nuclear magnetic resonance
IR: infrared spectrum
DMSO-d$_6$: deuterated dimethyl sulfoxide
WSC: 1-ethyl-3-(3-dimethylaminopropyl)carbodiimide hydrochloride
HOBt: 1-hydroxy-1H-benztriazole
IPE: diisopropyl ether
DMAP: 4-dimethylaminopyridine
WSCD: 1-ethyl-3-(3-dimethylaminopropyl)carbodiimide Reference Example 1

4-(4-Biphenylylmethoxy)phenyl Acetic Acid

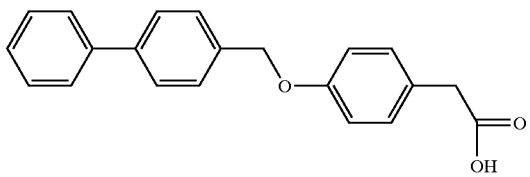

To a solution of ethyl 4-hydroxyphenylacetic acid (3.6 g) in DMF (50 ml) were added potassium carbonate (2.5 g) and 4-phenylbenzyl chloride (4 g) sequentially. After stirring at 60° C. for 6 hr, the reaction mixture was poured onto water and the resulting crystals were suspended in ethyl acetate. The suspension was washed with water and concentrated. The resulting crude crystals were dissolved in THF (100 ml)/ethanol (50 ml) and 2 N sodium hydroxide (20 ml) was added to the solution. The reaction mixture was heated under stirring at 60° C. for 18 hr and concentrated. The residue was acidified with 2 N hydrochloric acid and the resulting crystals were collected by filtration and washed with ethyl ether to obtain the titled compound (5.3 g).

m.p.: 170–171° C.

Reference Example 2

Methyl 6-hydroxynicotinate

To methanol (100 ml) in an ice bath was added thionyl chloride (16 ml) followed by addition of 6-hydroxynicotinic acid (10 g).

The reaction mixture was warmed to room temperature and stirring was continued for sixty hr. After concentration, the reaction mixture was diluted with saturated aqueous sodium bicarbonate and extracted with the combined mixture of THF and ethyl acetate.

The organic layer was washed with water and saturated aqueous sodium chloride, dried, and concentrated. The residue was recrystallized from THF/diisopropyl ether to obtain the titled compound (3.4 g).

m.p.:164–166° C.

Reference Example 3

Methyl 1-(4-biphenylylmethyl)-1,6-dihydro-6-oxo-3-pyridinecarboxylate

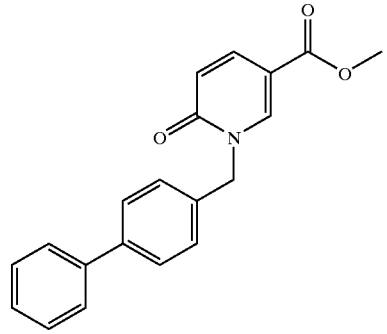

A mixture of methyl 6-hydroxynicotinate (3 g), 4-biphenylylmethyl bromide (5.8 g), potassium carbonate (8.2 g), and DMF (30 ml) was stirred at room temperature for 12 hr. The reaction mixture was diluted with water and extracted with ethyl acetate. The organic layer was washed with water and saturated aqueous sodium chloride sequentially and concentrated. The resulting crystals were washed with diisopropylether and recrystallized from ethyl acetate/hexane to obtain the titled compound (5.1 g).

m.p.:130–133° C.

Reference Example 4

1-(4-Biphenylylmethyl)-1,6-dihydro-6-oxo-3-pyridinecarboxylic Acid

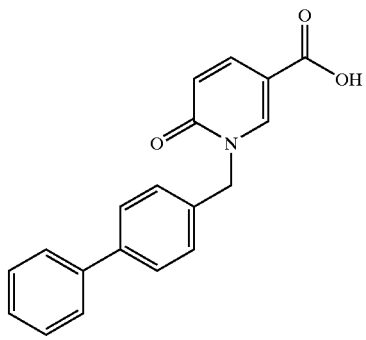

To a solution of methyl 1-(4-biphenylylmethyl)-1,6-dihydro-6-oxo-3-pyridinecarboxylate (4.5 g) in methanol (50 ml)/THF (50 ml) was added dropwise 1N aqueous sodium hydroxide (28 ml) at room temperature. The reaction mixture was stirred at room temperature for 3 hr and concentrated. The residue was diluted with 1 N hydrochloric acid (30 ml) and extracted with a mixed solvent of ethyl acetate and THF. The organic layer was washed with saturated aqueous sodium chloride, dried, and concentrated. Diisopropylether was added to the residue and the resulting crystals were collected by filtration to obtain the titled compound (4.2 g).

m.p.: 245–250° C.

Reference Example 5

Methyl 6-(4-biphenylylmethoxy)nicotinate

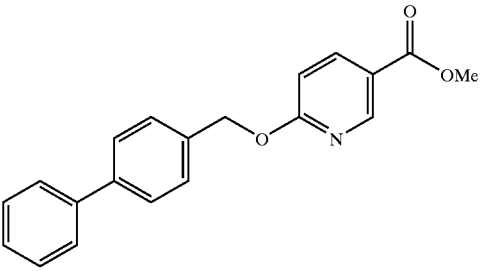

The mixture of methyl 6-hydroxynicotinate (6 g), 4-biphenylylmethyl bromide (7.7 g), silver carbonate (4.8 g), and toluene (60 ml) was stirred at 50° C. for 12 hr. The reaction mixture was further stirred at 100° C. for 6 hr and filtrated.

The filtrate was concentrated. The residue was purified by alumina column chromatography (eluent; ethyl acetate) and recrystallized from ethyl acetate/hexane to obtain the titled compound (2.5 g).

m.p.:121–123° C.

Reference Example 6

6-(4-Biphenylylmethoxy)nicotinic Acid

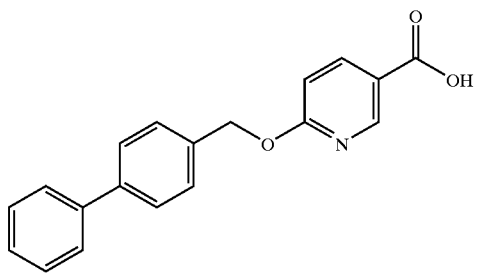

To a solution of methyl 6-(4-biphenylylmethoxy)nicotinate (2.0 g) in methanol (20 ml)/THF(40 ml) was added iN aqueous sodium hydroxide (13 ml) at room temperature. After stirring at room temperature for 4 hr the reaction mixture was diluted with 1 N hydrochloric acid (13 ml) and concentrated. The precipitate was collected by filtration and washed with water and diethyl ether sequentially to obtain the titled compound (1.6 g) as amorphous powder.

$^1$H-NMR (DMSO-d6) δ: 5.48 (2H, s), 6.96 (1H, d), 7.30–7.74 (9H, m), 8.18 (1H, dd), 8.74 (1H, d).

Reference Example 7

5-Chloro-N-[2-(N,N-diethylamino)ethyl]-2-methoxy-4-(1-naphthoylamino)benzamide

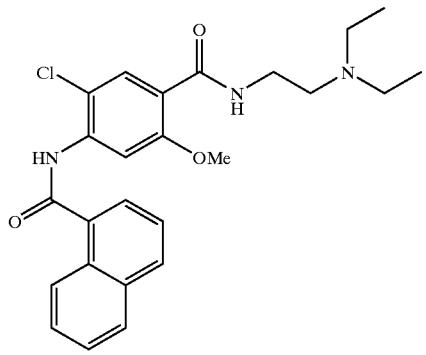

To a solution of metoclopramide (free form, 500 mg) in pyridine (50 ml) was added 1-naphtharenecarbonyl chloride (350 mg). The reaction mixture was heated under reflux for 2 hr and cooled to room temperature. The reaction mixture was concentrated, diluted with 1 N hydrochloriclacid (100 ml), and washed with ethyl acetate. The aqueous layer was basified to pH 10 by adding 1 N sodium hydroxide and extracted with ethyl acetate. The organic layer was washed with saturated aqueous sodium chloride, dried, and concentrated. The residue was purified by silica gel column chromatography (eluent; ethyl acetate/ethanol=4/1) to obtain the titled compound (280 mg) as amorphous powder.

$^1$H-NMR(CDCl$_3$) δ: 1.06 (6H, t), 2.50–2.70 (6H, m)., 3.52 (2H, q), 4.04 (3H, s), 7.55–7.70 (2H, m), 7.85–8.05 (4H, m), 8.31 (1H, s), 8.35–8.50 (2H, m), 8.55 (1H, s), 8.78 (1H, s).

Reference Example 8

5-Chloro-N-[2-(N,N-diethylamino)ethyl]-2-methoxy-4-(2-naphthoylamino)benzamide

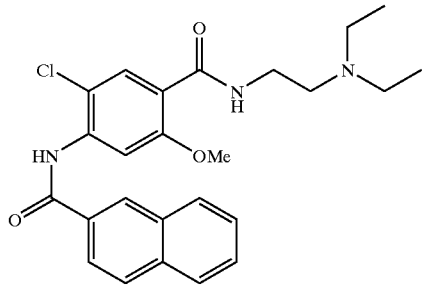

The titled compound was prepared by the procedure similar to Reference example 7.

m.p.: 173–174° C.

Recrystallizing solvent: ethyl acetate/diisopropyl ether.

Reference Example 9

5-Chloro-N-[2-(N,N-diethylamino)ethyl]-2-methoxy-4-[(1-naphthylsulfonyl)amino]benzamide

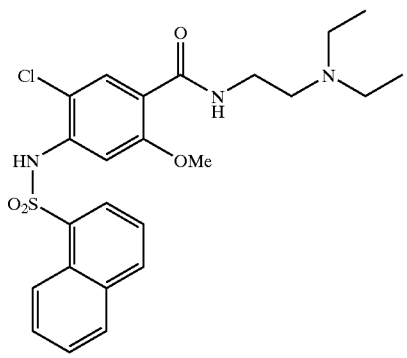

The titled compound was prepared by the procedure similar to Reference example 7.

Amorphous powder.

$^1$H-NMR(CDCl$_3$) δ: 1.01 (6H, t, J=7.0 Hz), 2.50–2.70 (6H, m), 3.52 (2H, q, J=5.2 Hz), 3.82 (3H, s), 7.17 (1H, s), 7.44 (1H, t, J=7.6 Hz), 7.50–7.70 (2H, m), 7.89 (1H, d, J=7.6 Hz), 7.95 (1H, s), 8.01 (1H, d, J=8.0 Hz), 8.17–8.30 (2H, m), 8.71 (1H, d, J=8.0 Hz).

Reference Example 10

5-Chloro-N-[2-(N,N-diethylamino)ethyl]-2-methoxy-4-[(2-naphthylsulfonyl)amino]benzamide

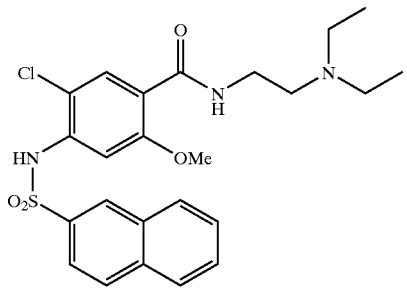

The titled compound was prepared by the procedure similar to Reference example 7.

m.p.: 148–149° C.

Recrystallizing solvent: ethyl acetate/diisopropyl ether.

Reference Example 11

N-[3-[4-(2-Naphthylmethoxy)phenyl]propyl]-N,N-dipropylamine Hydrochloride

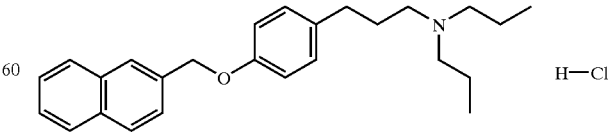

To a mixture of 4-[3-(N,N-dipropylamino)propyl]phenol hydrochloride (0.152 g), 2-bromomethylnaphthalene (0.165 g), and DMF (10 ml) was added potassium carbonate (0.131 g). Sodium hydride (60% oil dispersion: 0.044 g) was added to the reaction mixture under ice cooling and the reaction mixture was stirred at room temperature for one hr. The reaction mixture was diluted with water and extracted with ethyl acetate. The organic layer was washed with water and saturated aqueous sodium chloride sequentially, dried, and concentrated. The residue was purified by alumina column chromatography (eluent: hexane/ethyl acetate=4/1) and converted into its hydrochloride by 4 N hydrochloric acid/ethyl acetate solution followed by recrystallization from methanol/diisopropylether to obtain the titled compound (0.169 g).

m.p.: 130–132° C.

The following Reference example compounds 12–20 were prepared by the method similar to Reference example 11.

Reference Example 12

N-[3-[4-[(2,4-Dichlorobenzyl)oxy]phenyl]propyl]-N,N-dipropylamine Hydrochloride

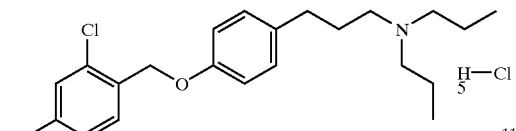

m.p.: 117–120° C.

(Recrystallizing solvent: methanol/diisopropylether).

Reference Example 13

N-[4-(2-Naphthylmethoxy)phenethyl]-N,N-dipropylamine Hydrochloride

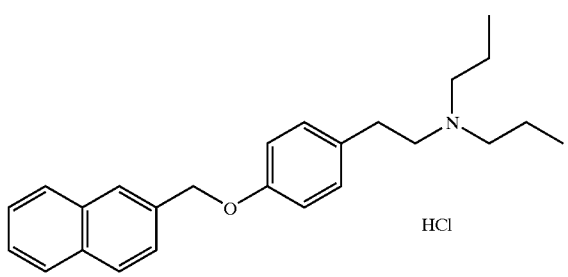

m.p.: 113–115° C.

Recrystallizing solvent: methanol/diethyl ether.

Reference Example 14

N-[4-[(2,4-Dichlorobenzyl)oxy]phenethyl]-N,N-dipropylamine Hydrochloride

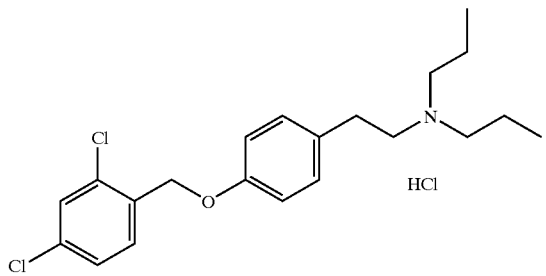

m.p.: 122–123° C.

Recrystallizing solvent: ethanol/diethyl ether.

Reference Example 15

N-[4-(4-Biphenylylmethoxy)phenethyl]-N,N-dipropylamine Hydrochloride

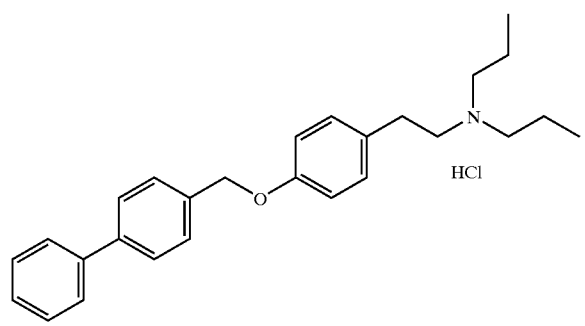

m.p.: 149–150° C.

Recrystallizing solvent: ethanol/diethyl ether.

Reference Example 16

N-[2-(2-Naphthylmethoxy)phenethyl]-N,N-dipropylamine Hydrochloride

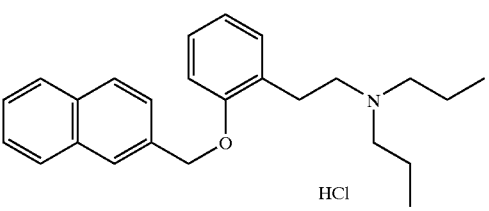

m.p.: 146–147° C.

Recrystallizing solvent: ethanol/diethyl ether.

Reference Example 17

N-[3-(2-Naphthylmethoxy)phenethyl]-N,N-dipropylamine Hydrochloride

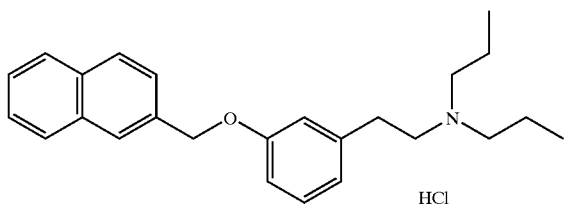

m.p.: 115–116° C.

Recrystallizing solvent: ethanol/diethyl ether.

Reference Example 18

N-[3-(4-Biphenylylmethoxy)phenethyl]-N,N-dipropylamine Hydrochloride

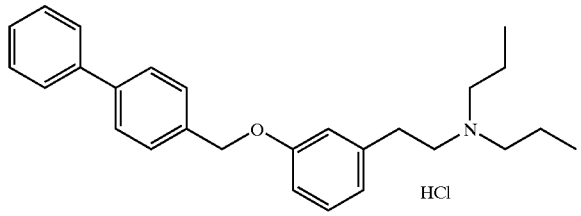

m.p.: 108–110° C.

Recrystallizing solvent: ethanol/diethyl ether.

Reference Example 19

N-[3-[(2,4-Dichlorobenzyl)oxy]phenethyl]-N,N-dipropylamine Hydrochloride

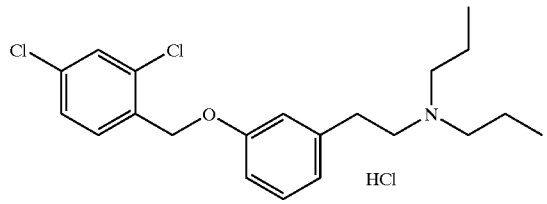

m.p.: 76–78° C.

Recrystallizing solvent: ethanol/diethyl ether.

Reference Example 20

N-[3-(1-Naphthylmethoxy)phenethyl]-N,N-dipropylamine Hydrochloride

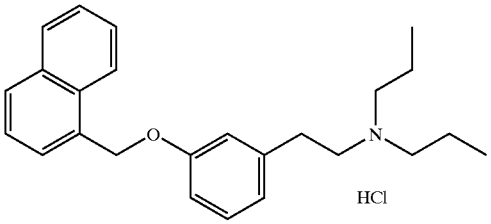

m.p.: 140–142° C.

Recrystallizing solvent: ethyl acetate/diethyl ether.

Reference Example 21

3-(4-Benzyloxyphenyl)propyl Iodide

To a solution of 3-(4-benzyloxyphenyl)propylalcohol (3.483 g) and pyridine (1.8 ml) in dichloromethane (30 ml) was added p-toluenesulfonyl chloride (2.73 g) at room temperature. The reaction mixture was stirred overnight at room temperature, diluted with water, and extracted with dichloromethane. The organic layer was washed with water and saturated aqueous sodium chloride sequentially, dried, and concentrated. The residue was dissolved in acetone (50 ml) and sodium iodide (3.34 g) was added to the solution. The reaction mixture was heated under reflux for 3 hr and cooled. The reaction mixture was diluted with water and extracted with ethyl acetate. The organic layer was washed with water and saturated aqueous sodium chloride sequentially, dried, and concentrated to obtain the titled compound (4.275 g).

$^1$H-NMR (CDCl$_3$) δ: 2.09(2H, m), 2.67(2H, t), 3.16(2H, t), 5.04(2H, s), 6.90(2H, d), 7.11(2H, d), 7.30–7.47(5H, m).

Reference Example 22

4-[3-(N,N-Dipropylamino)propyl]phenol Hydrochloride

To a solution of 3-(4-benzyloxyphenyl)propyl iodide (1.790 g) in DMF (20 ml) were added N,N-dipropylamine (1.3 ml) and potassium carbonate (1.391 g). The reaction mixture was stirred at room temperature for 29 hr, diluted with water, and extracted with ethyl acetate. The residue was purified by silica gel column chromatography (eluent:hexane/ethyl acetate=1/1) to obtain 3-(4-benzyloxyphenyl)propyl-N,N-dipropylamine (1.589 g).

To a solution of 3-(4-benzyloxyphenyl)propyl-N,N-dipropylamine (1.589 g) in methanol (30 ml) was added 10% palladium carbon (0.499 g) and hydrogenation reaction was conducted under hydrogen atmosphere at room temperature overnight. The catalyst was removed by filtration and the filtrate was concentrated. The residue was purified by alumina column chromatography (eluent:hexane/ethyl acetate=1/1), converted into its hydrochloride, which was recrystallized from methanol/ethyl acetate to obtain the titled compound.

m.p.: 139–141° C.

Reference Example 23

2,2,2-Trifluoro-N-[2-(methylamino)ethyl]acetamide

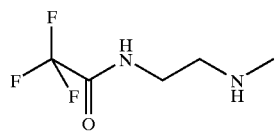

To a solution of ethyl trifluoroacetate (10 ml) in diethyl ether (20 ml) in an ice bath was added dropwise N-methylethylenediamine (7.4ml) for one hr. After addition, the reaction mixture was warmed to room temperature and stirred for 2 hr. Removal of ethyl ether from the reaction mixture gave the titled compound (14 g).

Oily material.

$^1$H-NMR (CDCl$_3$) δ: 2.39(3H, s), 2.77–2.83(2H, t, J=6.0 Hz), 3.40–3.16(2H, t, J=6.0 Hz).

Reference Example 24 tert-Butyl(methyl)[2-[(2,2,2-trifluoroacetyl)amino]ethyl]carbamate

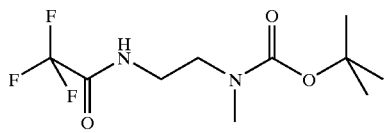

To a solution of 2,2,2-trifluoro-N-[2-(methylamino)ethyl]acetamide (7 g) in THF (100 ml) in an ice bath was added a solution of di-tert-butylcarbamate (10.4 ml) in THF (90 ml) for one hr. After addition, the reaction mixture was warmed to room temperature and stirring was continued for further 3 hr. THF was distilled from the reaction mixture and the residue was dissolved in ethyl acetate, washed with water and saturated aqueous sodium chloride sequentially. Desiccation with sodium sulfate followed by concentration gave the crude crystals, which were further recrystallized from hexane-IPE to yield the titled compound (9.22 g).

Oily material.

$^1$H-NMR (CDCl$_3$) δ: 1.46(9H, s), 2.90(3H, s), 3.48–3.50 (4H, m).

Reference Example 25 tert-Butyl 2-aminoethyl(methyl)carbamate

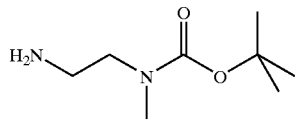

To a solution of tert-butyl(methyl)[2-[(2,2,2-trifluoroacetyl)amino]ethyl]carbamate (1 g) in methanol (10 ml) in an ice bath was added aqueous 10% potassium carbonate (5 ml). After addition, the reaction mixture was warmed to room temperature and stirring was continued for additional 20 hr. The reaction mixture was concentrated and the residue was dissolved in ethyl acetate. The insoluble material was removed by filtration and the filtrate was concentrated to obtain the titled compound (451 mg).

Oily material.

$^1$H-NMR (CDCl$_3$) δ: 1.46(9H, s), 2.79–2.86(2H, t, J=6.4 Hz), 2.89(3H, s), 3.24–3.31(2H, t, J=6.6 Hz).

Reference Example 26 tert-Butyl 2-[4-(4-biphenylylmethoxy)phenylacetylamino]ethyl(methyl)carbamate

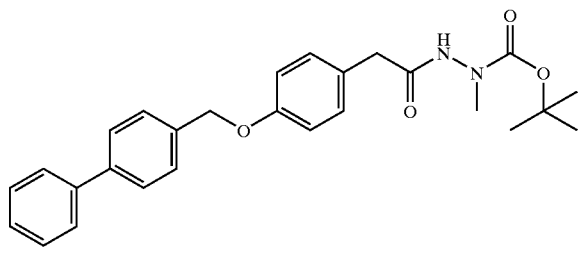

4-(4-Biphenylylmethoxy)phenylacetic acid (1.51 g), tert-butyl 2-aminoethyl(methyl)carbamate (826 mg), WSC (1 g), 1-hydroxybenzotriazole (798 mg), and triethylamine (2.2 ml) were added to THF (90 ml). The reaction mixture was stirred at room temperature for 20 hr and poured onto water, followed by extraction with ethyl acetate-THF (1:1). The organic layer was washed with water, saturated aqueous sodium bicarbonate, and saturated aqueous sodium chloride sequentially, dried with sodium sulfate, and concentrated. The residue was purified by alumina column chromatography (eluent; methanol:THF=1:1) followed by recrystallization from THF-IPE gave the titled compound (888 mg).

m.p.:109–110° C.

Reference Example 27

Ethyl 7-[methyl-[2-[(2,2,2-trifluoroacetyl)amino]ethyl]-amino]heptanoate

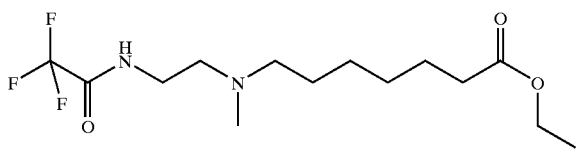

To a solution of 2,2,2-trifluoro-N-[2-(methylamino)ethyl] acetamide (5 g) in DMF (50 ml) were added ethyl 7-bromoheptanoate (3.6 ml) and potassium carbonate (7.7 g) and stirring was continued at room temperature for 18 hr. Potassium carbonate was removed by filtration and saturated aqueous sodium bicarbonate and water was added to the filtrate, which was extracted with ethyl acetate. The organic layer was washed with water and saturated aqueous sodium chloride sequentially, dried with sodium sulfate, and concentrated. The residue was dissolved in toluene and purified by passing through the silica gel column (eluent; hexane to hexane-ethyl acetate (4:1) to ethyl acetate) to obtain the titled compound as a crude material (7 g).

Oily material.

$^1$H-NMR (CDCl$_3$) δ: 1.22–1.66(10H, m), 2.21(3H, s), 2.26–2.40 (4H, m), 2.50–2.55(2H, t, J=6.0 Hz), 3.35–3.51 (2H, dd, J=14.2, 7.0 Hz), 4.08–4.18(2H, m).

Reference Example 28

Ethyl 7-[(2-aminoethyl)(methyl)amino]heptanoate

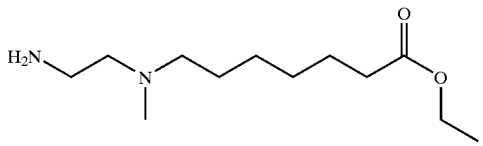

To a solution of ethyl 7-[methyl-[2-[(2,2,2-trifluoroacetyl)amino]ethyl]amino]heptanoate (4.89 g) in ethanol (80 ml) in an ice bath was added 10% aqueous potassium carbonate (30 ml) and stirring was continued for 20 hr. The reaction mixture was concentrated and the residue was dissolved in ethyl acetate. The insoluble material was removed by filtration and the filtrate was concentrated to obtain the titled compound (3 g)

Oily material.

$^1$H-NMR (CDCl$_3$) δ: 1.26–1.63 (10H, m), 2.05 (3H, s), 2.20–2.41(4H, m), 2.73–2.79 (2H, t, J=6.3 Hz), 4.07–4.18 (2H, dd, J=14.4, 7.2 Hz).

Reference Example 29

Benzyl 4-(2-((2-(dimethylamino)ethyl)(methyl)amino)-2-oxoethyl)phenylcarbamate

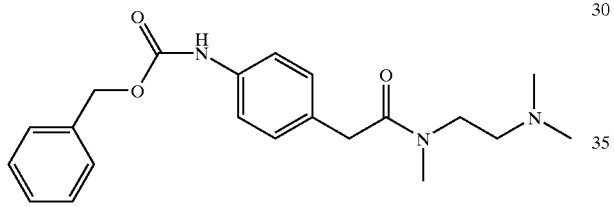

To a solution of (4-(((benzyloxy)carbonyl)amino)-phenyl)acetic acid (6 g) in THF (100 ml) were added WSC (4 G), HOBt (3 g), and N,N,N-trimethylethylenediamine (2.1 g) sequentially. Triethylamine (3 ml) was added to the reaction mixture. After stirring at room temperature overnight, the reaction mixture was extracted with ethyl acetate. The organic layer was washed with water, dried, and concentrated. The residue was recrystallized from IPE/ethyl acetate to obtain the titled compound (7 g).

m.p.: 109–110° C.

Reference Example 30

2-(4-Aminophenyl)-N-(2-(dimethylamino)ethyl)-N-methylacetamide

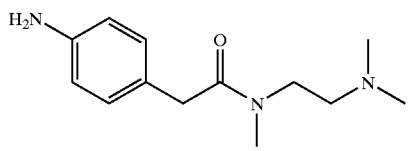

To a solution of benzyl 4-(2-((2-(dimethylamino)ethyl)(methyl)amino)-2-oxoethyl)phenylcarbamate (0.7 g) in ethanol (10 ml) was added 10% Pd-C (0.2 g). The reaction mixture was hydrogenated under atmospheric pressure at room temperature for one hr. The catalyst was removed by filtration and the filtrate was concentrated to obtain the titled compound (0.43 g).

m.p.: 235–240° C. (as dihydrochloride; recrystallized from ethanol/IPE).

Reference Example 31 tert-Butyl 2-(((4-([1,1'-biphenyl]-4-ylmethoxy)phenyl)acetyl)amino)ethylcarbamate

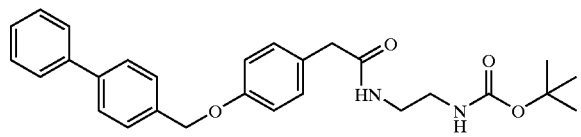

To a solution of (4-([1,1'-biphenyl]-4-ylmethoxy)phenyl)acetic acid (2.1 g) in THF (100 ml) were added WSC (1.4 g), HOBt (1 g), and t-butyl N-(2-aminoethyl)carbamate (1 g). After stirring overnight, the reaction mixture was diluted in THF-ethyl acetate, washed with 10% aqueous potassium carbonate, dried, and concentrated. The residue was recrystallized from ethanol to obtain the titled compound (1.8 g).

m.p.: 175–176° C.

Reference Example 32

Methyl 4-(4-biphenylylcarbonylamino)benzoate

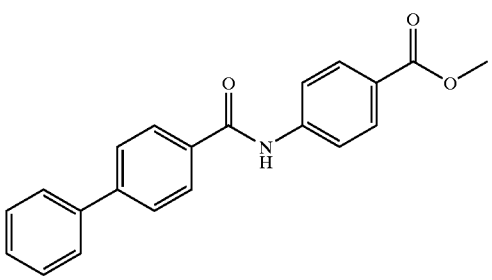

To a solution of 4-biphenylcarboxylic acid (2.184 g) in THF (30 ml) in an ice bath were added oxalyl chloride (1.2 ml) and DMF (0.04 ml). After stirring at room temperature for 30 min, the reaction mixture was concentrated. The residue was dissolved in THF (15 ml) and was added into a solution of methyl 4-aminobenzoate (1.512 g) and triethylamine (2.1 ml) in THF (30 ml) at 0° C. After stirring for 30 min, the reaction mixture was diluted with 10% aqueous citrate and extracted with ethyl acetate. The organic layer was washed with water and saturated aqueous sodium chloride sequentially, dried, and concentrated. The resulting crude crystals were washed with diethyl ether to obtain the titled compound (2.179 g).

m.p.:247–251° C.

Reference Example 33

4-(4-Biphenylylcarbonylamino)benzoic Acid

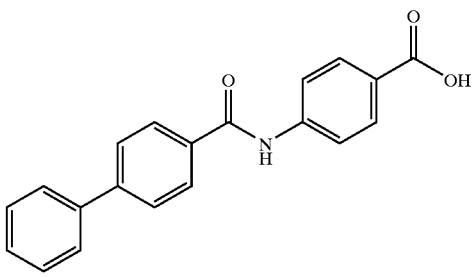

To a solution of methyl 4-(4-biphenylylcarbonylamino) benzoate (1.998 g) in THF (60 ml)/methanol (20 ml) was added 1N aqueous sodium hydroxide (8 ml) and stirring was continued at room temperature for 18 hr. The reaction mixture was diluted with 1 N hydrochloric acid (10 ml) and extracted with ethyl acetate. The organic layer was washed with water and saturated aqueous sodium chloride sequentially, dried, and concentrated. The resulting crude crystals were washed with diethyl ether to obtain the titled compound (1.760 g).

m.p.:>320° C.

Reference Example 34

Methyl 4-(4-biphenylylmethoxy)phenylacetate

A solution of 4-biphenylmethanol (800 g) in DMF (2.4 l) as cooled to 0° C and thionyl chloride (380 ml) was added to the solution for 40 min. The temperature of the reaction mixture was raised to 30±2° C. and stirring was continued for additional one hr. Methyl 4-hydroxyphenylacetate (722 g) was added and stirring was continued for 20 min at this temperature. 28% Sodium methoxide (2.93 kg) was added to the solution for 70 min and stirring was continued for 6 hr while the temperature of the reaction mixture was maintained at 50±2° C. Water (3.21) was added to the reaction mixture for 25 min while the temperature of the reaction mixture was maintained at 50±2° C. which was stirred for additional one hr at same temperature and cooled to room temperature. The precipitate was collected by filtration and washed with methanol (1.6 l) and water (6.41) sequentially to obtain the titled compound (1119 g).

m.p.:115–116° C.

Reference Example 35

4-(4-Biphenylylmethoxy)phenyl-N-[2-(N,N-dimethylamino)ethyl]acetamide

A suspension of methyl 4-(4-biphenylylmethoxy) phenylacetate (1000 g), N,N-dimethylethylenediamine (795 g), and 1H-1,2,4-triazole (207 g) in methanol (2.0 l) was heated under reflux under nitrogen for 10 hr and was left to stand at room temperature over night. The reaction mixture was warmed to 60±2° C. and methanol (4.0 l) was added for 35 min. After stirring under reflux for additional one hr the reaction mixture was cooled to room temperature. The precipitate was collected by filtration and washed with methanol (2.0 l) to obtain the titled compound (1109 g).

Reference Example 36

4-(4-Biphenylylmethoxy)phenyl-N-[2-(N,N-dimethylamino)ethyl]acetamide

A solution of methyl 4-(4-biphenylylmethoxy) phenylacetate (60.0 g), N,N-dimethylethylenediamine (47.7 g), and 1H-1,2,4-triazole (12.6 g) in toluene (120 ml) was stirred under nitrogen at 100° C. for 8 hr and cooled until the temperature of the reaction mixture was reached to 60±2° C., to which ethyl acetate (240 ml) was added for 20 min. The reaction mixture was further heated under reflux for additional 30 min, left to stand at room temperature over night and stirred in an ice bath for 2 hr. The precipitate was collected by filtration and washed with ethyl acetate (120 ml) to obtain the titled compound (71.7 g).

Reference Example 37

4-(4-Biphenylylmethoxy)phenyl-N-[2-(N,N-dimethylamino)ethyl]acetamide

A suspension of methyl 4-(4-biphenylylmethoxy) phenylacetate (2.00 g), N,N-dimethylethylenediamine (1.60 g), 2-hydroxypyridine (573 mg) in methanol (4.0 ml) was heated under reflux under nitrogen for 16 hr and cooled until the temperature of the reaction mixture reached to 60±2° C., to which methanol (8.0 ml) was added. The reaction mixture was heated under reflux for additional one hr and cooled to room temperature. The precipitate was collected by filtration and washed with methanol (4.0 ml to obtain the titled compound (2.18 g).

Reference Example 38

4-(4-Biphenylylmethoxy)phenyl-N-[2-(N,N-dimethylamino)ethyl]acetamide

A suspension of methyl 4-(4-biphenylylmethoxy) phenylacetate (1.00 g), N,N-dimethylethylenediamine (0.80 g), and imidazole (205 mg) in methanol (2.0 ml) was heated under reflux under nitrogen for 30 min and cooled until the temperature of the reaction mixture reached to 60±2° C. Methanol (4.0 ml) was added to the reaction mixture, which was heated under reflux for additional one hr and cooled to room temperature. The precipitate was collected by filtration and washed with methanol (2.0 ml) to obtain the titled compound (1.03 g).

Reference Example 39

2-(4-([1,1'-Biphenyl]-4-ylmethoxy)phenyl)-N-(2-(dimethylnitroryl)ethyl)acetamide

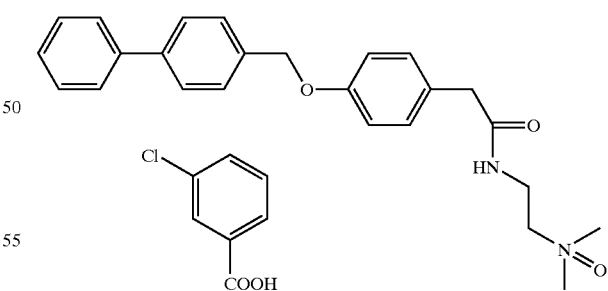

To a solution of 2-(4-([1,1'-biphenyl]-4-ylmethoxy) phenyl)-N-(2-(dimethylamino)ethyl)acetamide (0.2 g) in acetone (30 ml) was added m-chloroperbenzoic acid (0.2 g) and stirring was continued at room temperature for 18 hr. The reaction mixture was concentrated. The residue was recrystallized twice from ethyl acetate to obtain the titled compound (0.1 g).

m.p.:134–135° C.

EXAMPLE 1

4-4-Biphenylylmethoxy)phenyl-N-(2-piperidinoethyl)acetamide

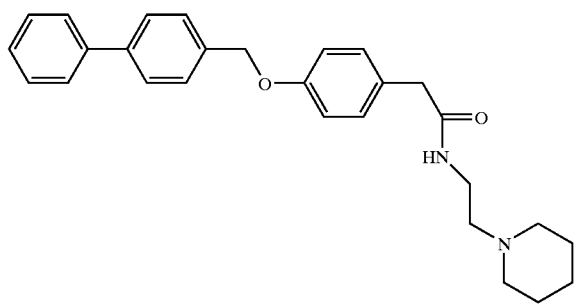

To a solution of 4-(4-biphenylylmethoxy)phenylacetic acid (0.6 g) in THF (30 ml) were added WSC (0.4 g), and HOBt (0.3 g). 1-(2-Aminoethyl)piperidine (0.28 g) was added to the reaction mixture. After stirring at room temperature for 18 hr, the reaction mixture was poured onto water and extracted with ethyl acetate. The organic layer was washed with water, dried, and concentrated. The residue was recrystallized from ethyl acetate to obtain the titled compound (0.5 g).

m.p.:153–154° C.

EXAMPLE 2

4-(4-Biphenylylmethoxy)phenyl-N-[2-(N,N-dimethylamino)ethyl]acetamide

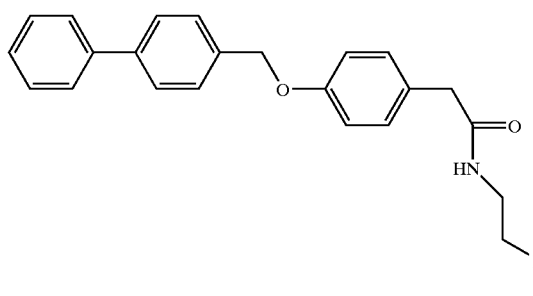

To a solution of 4-(4-biphenylylmethoxy)phenylacetic acid (0.6 g) in THF (30 ml) were added WSC (0.4 g) and HOBt (0.3 g). N,N-Dimethylethylenediamine (0.2 g) was added to the reaction mixture. After stirring at room temperature for 18 hr, the reaction mixture was poured onto water and extracted with ethyl acetate. The organic layer was washed with water, dried, and concentrated in vacuo. The residue was recrystallized from ethyl acetate/ethanol to obtain the titled compound (0.3 g).

m.p.:160–161° C.

EXAMPLE 3

6-(4-Biphenylylmethoxy)-N-[2-(pyrrolidin-1-yl)ethyl]nicotinamide

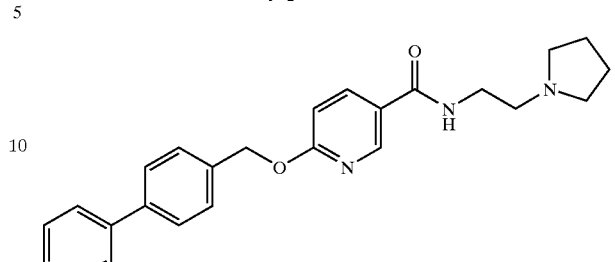

To a solution of 1-(2-aminoethyl)pyrrolidine (230 mg) in acetonitrile (5 ml)/THF (10 ml) were added 6-(4-biphenylylmethoxy)nicotic acid (500 mg), WSC (380 mg), HOBt (260 mg), and triethylamine (0.7 ml) at room temperature. After stirring for 36 hr, the reaction mixture was diluted with aqueous 5% potassium carbonate and extracted with ethyl acetate. The organic layer was washed with water and aqueous saturated aqueous sodium chloride, dried, and concentrated. The residue was purified by alumina column chromatography (eluant; THF) and recrystallized from ethyl acetate/diisopropylether to obtain the titled compound (540 mg).

m.p.:153–157° C.

EXAMPLE 4

1-(4-Biphenylylmethyl)-1,6-dihydro-6-oxo-N-[2-(pyrrolidin-1-yl)ethyl]-3-pyridinecarboxamide

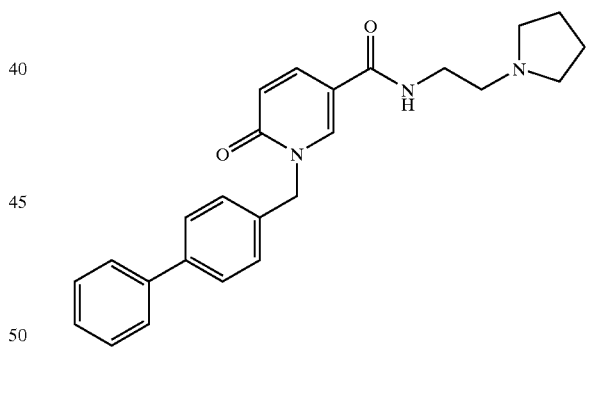

To a solution of 1-(2-aminoethyl)pyrrolidine (230 mg) in acetonitrile (5 ml)/THF (10 ml) were added 1-(4-biphenylylmethyl)-1,6-dihydro-6-oxo-3-pyridinecarboxylic acid (500 mg), WSC (380 mg), HOBt (260 mg), and triethylamine (0.7 ml) at room temperature. After stirring at room temperature for 12 hr, the reaction mixture was diluted with 5% aqueous potassium carbonate and extracted with ethyl acetate. The organic layer was washed with water and saturated aqueous sodium chloride sequentially, dried, and the solvent was removed in vacuo. The residue was purified by alumina column chromatography (eluent; THF) and recrystallized from ethyl acetate/diisopropylether to obtain the titled compound (450 mg).

m.p.:142–152° C.

EXAMPLE 5

1-(4-Biphenylylmethyl)-1,6-dihydro-6-oxo-N-(2-piperidinoethyl)-3-pyridinecarboxamide

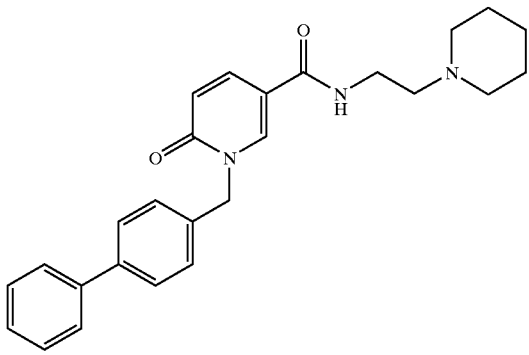

To a solution of 1-(2-aminoethyl)piperidine (260 mg) in acetonitrile (5 ml)/THF (10 ml) were added 1-(4-biphenylylmethyl)-1,6-dihydro-6-oxo-3-pyridinecarboxylic acid (500 mg), WSC (380 mg), HOBt (260 mg), and triethylamine (0.7 ml) at room temperature. After stirring at room temperature for 12 hr, the reaction mixture was diluted with 5% aqueous potassium carbonate and extracted with ethyl acetate. The organic layer was washed with water and saturated aqueous sodium chloride sequentially, dried, and concentrated. The residue was purified by alumina column chromatography (eluent; THF) and recrystallized from ethyl acetate/diisopropyl ether to obtain the titled compound (410 mg).

m.p.:137–142° C.

EXAMPLE 6

6-(4-Biphenylylmethoxy)-N-(2-piperidinoethyl) nicotinamide

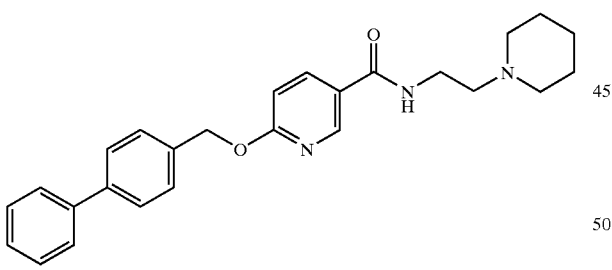

To a solution of 1-(2-aminoethyl)piperidine (260 mg) in acetonitrile (5 ml)/THF (10 ml) were added 6-(4-biphenylylmethoxy)nicotinic acid (500 mg), WSC (380 mg), HOBt (260 mg), and triethylamine (0.7 ml) at room temperature. After stirring at room temperature for 36 hr, the reaction mixture was diluted with 5% aqueous potassium carbonate and extracted with ethyl acetate. The organic layer was washed with water and saturated aqueous sodium chloride sequentially, dried, and concentrated. The residue was purified by alumina column chromatography (THF) and recrystallized from ethyl acetate to obtain the titled compound (450 mg).

m.p.:160–163° C.

EXAMPLE 7

6-(4-Biphenylylmethoxy)-N-[2-(N,N-dimethylamino)ethyl]nicotinamide

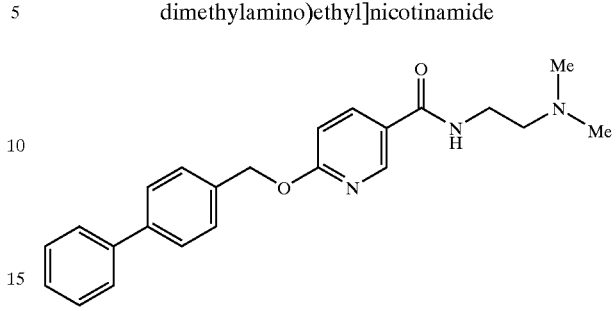

To a solution of N,N-dimethylethylenediamine (160 mg) in acetonitrile (5 ml)/THF (10 ml) were added 6-(4-biphenylylmethoxy)nicotinic acid (450 mg), WSC (340 mg), HOBt (230 mg), and triethylamine (0.7 ml) at room temperature. After stirring at room temperature for 12 hr, the reaction mixture was diluted with 10% aqueous potassium carbonates and extracted with ethyl acetate/THF. The organic layer was washed with water and saturated aqueous sodium chloride, dried, and concentrated. The residue was purified by alumina column chromatography (eluent; THF) and recrystallized from ethyl acetate/diisopropyl ether to obtain the titled compound (400 mg).

m.p.:151–154° C.

EXAMPLE 8

4-(4-Biphenylylmethoxy)-N-(2-piperidinoethyl) benzamide

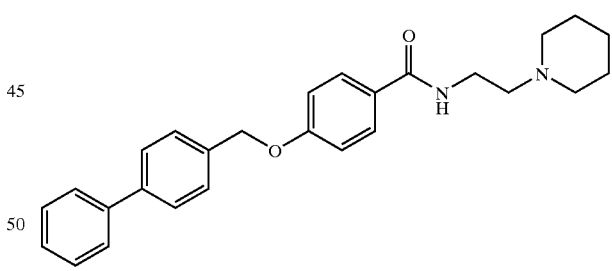

To a solution of 4-(4-biphenylylmethoxy)benzoic acid (1.008 g) in THF (20 ml)/acetonitrile (20 ml) were added WSC (0.775 g), HOBt (0.504 g), 1-(2-aminoethyl)piperidine (0.56 ml), and triethylamine (1.2 ml). After stirring at room temperature for 17 hr, the reaction mixture was diluted with water and extracted with ethyl acetate. The organic layer was washed with 10% aqueous potassium carbonate and saturated aqueous sodium chloride sequentially, dried, and concentrated. The residue was recrystallized from ethyl acetate/diisopropyl ether to obtain the titled compound (0.993 g).

m.p.:180–183° C.

EXAMPLE 9

4-(4-Biphenylylmethoxy)-N-[2-(pyrrolidin-1-yl)ethyl]benzamide

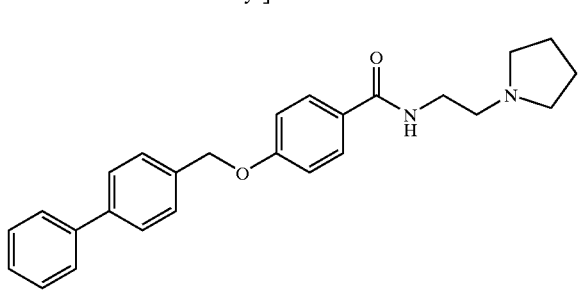

To a solution of 4-(4-biphenylylmethoxy)benzoic acid (1.005 g) in THF(30 ml)/acetonitrile (30 ml) were added, WSC (0.772 g), HOBt (0.516 g), 1-(2-aminoethyl)pyrrolidine (0.453 g), and triethylamine (1.2 ml). The reaction mixture was stirred at room temperature for 29 hr, diluted with water, and extracted with ethyl acetate. The organic layer was washed with 10% aqueous potassium carbonate and saturated aqueous sodium chloride sequentially, dried, and concentrated. The residue was recrystallized from ethanol/diisopropyl ether to obtain the titled compound (0.891 g).

m.p.:171–175° C.

EXAMPLE 10

2-Piperidinoethyl=4-(4-biphenylylmethoxy)benzoate

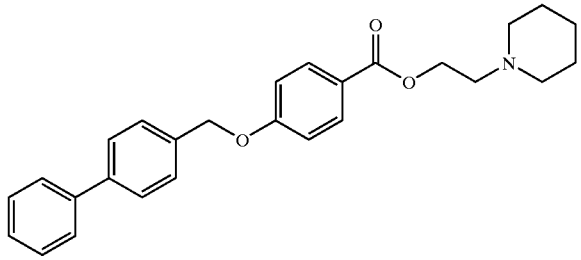

To a solution of 4-(4-biphenylylmethoxy)benzoic acid (0.302 g) in THF (10 ml)/acetonitrile (10 ml) were added WSC (0.228 g), HOBt (0.154 g), 1-piperidineethanol (0.157 g), and triethylamine (0.31 ml). After stirring at room temperature for 18 hr, the reaction mixture was diluted with water and extracted with ethyl acetate. The organic layer was washed with 10% aqueous potassium carbonate and saturated aqueous sodium chloride, dried, and concentrated. The residue was recrystallized from ethyl acetate/hexane to obtain the titled compound (0.152 g).

m.p.:86–87° C.

EXAMPLE 11

2-(Pyrrolidin-1-yl)ethyl=4-(4-biphenylylmethoxy)benzoate

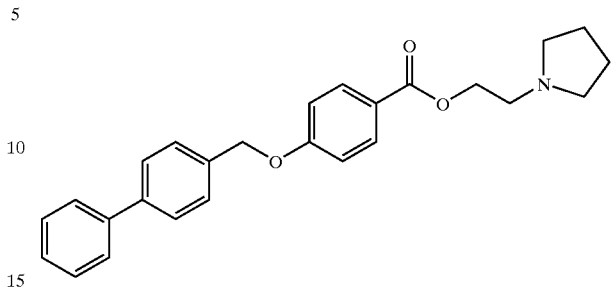

To a solution of 4-(4-biphenylylmethoxy)benzoic acid (0.303 g) in THF (5 ml)/acetonitrile (5 ml) were added WSC (0.236 g), HOBt (0.153 g), 1-pyrrolidineethanol (0.125 g), and triethylamine (0.17 ml). After stirring at room temperature for 18 hr, the reaction mixture was diluted with water and extracted with ethyl acetate. The organic layer was washed with 10% aqueous potassium carbonate and saturated aqueous sodium chloride sequentially, dried, and concentrated. The residue was recrystallized from ethyl acetate/hexane to obtain the titled compound (0.166 g).

m.p.:95–98° C.

EXAMPLE 12

4-[4-(Biphenylylmethoxy)phenyl]-N-[2-(N,N-dimethylamino)ethyl]acetamide Oxalate

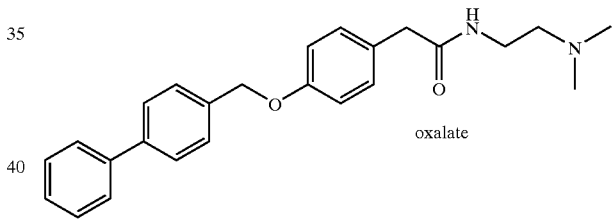

4-[4-(Biphenylylmethoxy)phenyl]-N-[2-(N,N-dimethylamino)ethyl]acetamide (200 mg) was dissolved in methanol and a solution of oxalic acid (46 mg) in methanol was added to the solution, which was concentrate. The resulting crude crystals were recrystallized from ethanol to obtain the titled compound (217 mg).

m.p.:170–171° C.

The following Example Compounds 13 and 14 were prepared according the procedure written in Example 12.

EXAMPLE 13

4-[4-(Biphenylylmethoxy)phenyl]-N-[2-(N,N-dimethylamino)ethyl]acetamide Maleate m.p.:122–123° C.

Recrystallizing solvent:ethanol.

EXAMPLE 14

4-[4-(Biphenylylmethoxy)phenyl]-N-[2-(N,N-dimethylamino)ethyl]acetamide fumarate m.p.:122–123° C.

Recrystallizing solvent:ethanol.

EXAMPLE 15

4-[(4-Biphenylylmethoxy)phenyl]-N-[2-(N-methylamino)ethyl]acetamide Hydrochloride

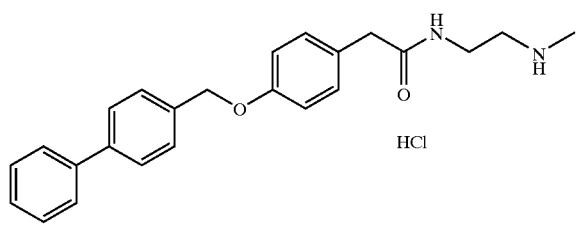

To a solution of tert-butyl 2-[4-(4-biphenylylmethoxy)phenylacetylamino]ethyl(methyl)carbamate (778 mg) in methanol (50 ml) in an ice bath was added dropwise 4 N hydrogen chloride in ethyl acetate (50 ml). The reaction mixture was warmed to room temperature, stirred for 30 min, and concentrated. The residue was recrystallized from methanol to obtain the titled compound (480 mg)

m.p.:214–215° C.

EXAMPLE 16

4-[(4-Biphenylylmethoxy)phenyl]-N-[2-(N-methylamino)ethyl]acetamide

4-[4-(Biphenylylmethoxy)phenyl]-N-[2-(N-methylamino)ethyl]acetamide hydrochloride (46 mg) was dissolved in saturated aqueous sodium bicarbonate, which was extracted with THF-ethyl acetate (1:1). The organic layer was washed with water and saturated aqueous sodium chloride sequentially, dried with sodium sulfate, and concentrated.

The residue was dissolved in THF and purified by passing through the aluminum column (eluent; THF to methanol) to obtain the titled compound (7 mg).

m.p.:165–166° C.

EXAMPLE 17

Ethyl 7-[2-[4-[(4-biphenylylmethoxy)phenyl]-acetylaminoethyl](methyl)amino]heptanoate 4-(4-Biphenylylmethoxy)phenylacetic acid (4.14 g), ethyl 7-[(2-aminoethyl)(methyl)amino]heptanoate (3 g), WSC (2.74 g), 1-hydroxybenzotriazole (2.19 g), and triethylamine (6.0 ml) were added to THF (200 ml). The reaction mixture was stirred at room temperature for 20 hr, poured onto water, and extracted with ethyl acetate-THF (1:1). The organic layer was washed with water, saturated aqueous sodium bicarbonate, and saturated aqueous sodium chloride sequentially, dried with sodium sulfate, and concentrated.

The residue was recrystallized from ethanol-IPE to obtain the titled compound (3.11 g).

m.p.:115–116° C.

EXAMPLE 18

7-[2-[4-[4-(Biphenylylmethoxy)phenyl]-acetylaminoethyl](methyl)amino]heptanoic Acid Hydrochloride

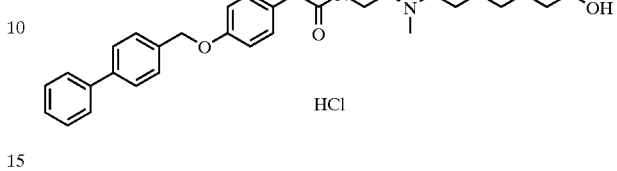

To a solution of ethyl 7-[2-[4-[(4-biphenylylmethoxy)phenyl]acetylaminoethyl](methyl)amino]hep tanoates (1 g) in methanol (50 ml)-THF (20 ml) was added 1N aqueous sodium hydroxide (15 ml), which was further stirred at room temperature for 4 hr. PH of the reaction mixture was adjusted to 5 by adding 1 N hydrochloric acid, which was extracted with ethyl acetate. The organic layer was washed with saturated aqueous sodium chloride, dried with sodium sulfate, and concentrated. The residue was dissolved in THF and 4 N hydrochloric acid was added to the solution, which was concentrated. The residue was recrystallized from THF-IPE to obtain the titled compound (838 mg).

m.p.:96–97° C.

EXAMPLE 19

N-(4-(2-((2-(Dimethylamino)ethyl)(methyl)amino)-2-oxoethyl)phenyl)[1,1'-biphenyl]-4-carboxamide

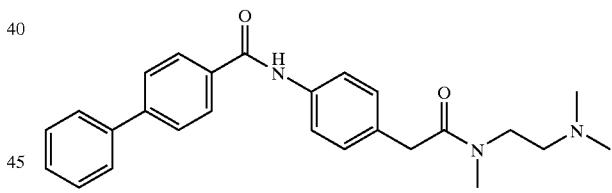

To a solution of biphenylylcarboxylic acid (0.25 g) in THF (5 ml) was added DMF (0.1 ml) followed by addition of oxalyl chloride (0.5 ml). After stirring at room temperature for 1 hr, the reaction mixture was concentrated. The residue was further azeotroped with toluene. The residue was dissolved in THF (1 ml) and added to a solution of 2-(4-aminophenyl)-N-(2-(dimethylamino)ethyl)-N-methylacetamide (0.3 g) in THF (40 ml) at room temperature. A saturated aqueous sodium bicarbonate (10 ml) was added to the solution, which was stirred at room temperature for 2 hr. The reaction mixture was extracted with ethyl acetate. The organic layer was washed with water, dried, and concentrated in vacuo. The residue was purified by alumina column chromatography (eluent:ethyl acetate) and recrystallized from IPE/ethyl acetate to obtain the titled compound (0.41 g).

m.p.:135–136° C.

EXAMPLE 20

N-(2-Aminoethyl)-2-(4-([1,1'-biphenyl]-4-ylmethoxy)phenyl)acetamide Hydrochloride

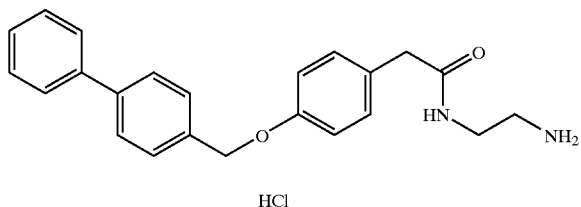

HCl

To a solution of tert-butyl 2-(((4-([1,1'-biphenyl]-4-ylmethoxy)phenyl)acetyl)amino)ethylcarbamate (1.5 g) in acetic acid (100 ml) was added 4N hydrochloric acid/ethyl acetate (4 ml) at room temperature. After stirring at room temperature for 2 hr, the precipitate was collected by filtration, which was washed with ethyl ether and dried to obtain the titled compound (0.9 g).

m.p.:228–229° C.

EXAMPLE 21

4-([1,1'-Biphenyl]-4-ylmethoxy)-N-(2-(1-pyrrolidinyl)ethyl)benzamide

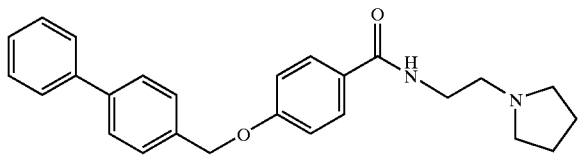

To a solution of 4-([1,1'-biphenyl]-4-ylmethoxy)benzoic acid (3 g) in THF (200 ml) were added WSC (2 g) and HOBt (1.5 g) followed by the addition of 1-(2-aminoethyl)pyrrolidine (1.1 g). After stirring at room temperature for 30 min, triethylamine (2 ml) added to the reaction mixture, which was stirred at room temperature for additional 72 hr. The reaction mixture was diluted with ethyl acetate, washed with 10% aqueous potassium carbonate and water sequentially, dried, and concentrated. The residue was recrystallized from ethanol/ethyl ether to obtain the titled compound (2.7 g).

m.p.:173–175° C.

EXAMPLE 22

N-[4-({[2-(Diethylamino)ethyl]amino}carbonyl)phenyl](4-biphenylyl)carboxamide

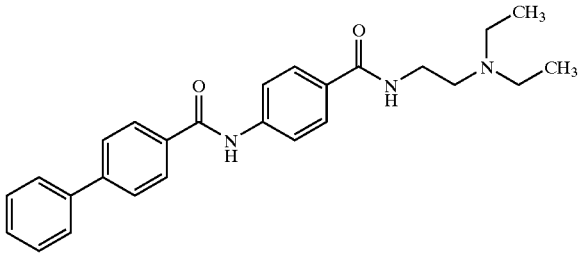

To a solution of 4-biphenylcarboxylic acid (0.879 g) in THF (15 ml) in an ice bath were added oxalyl chloride (0.46 ml) and DMF (one drop). After stirring at room temperature for 30 min, the reaction mixture was concentrated. The residue was dissolved in THF (10 ml) and added to the suspension of procainamide hydrochloride (1.078 g) and triethylamine (1.4 ml) in THF (20 ml) at 0° C. After stirring at 0° C. for 30 min, the reaction mixture was diluted with 10% aqueous potassium carbonate and extracted with ethyl acetate. The organic layer was washed with saturated aqueous sodium chloride, dried, and concentrated. The residue was recrystallized from methanol to obtain the titled compound (1.147 g).

m.p.:237–240° C. (decomposed).

EXAMPLE 23

4-(4-Biphenylyl)methoxy)-N-[2-(isopropylamino)ethyl]benzamide

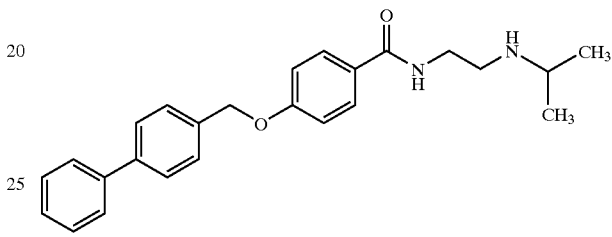

To a solution of 4-(4-biphenylylmethoxy)benzoic acid (1.007 g) in THF (30 ml)/acetonitrile (30 ml) were added WSC (0.708 g), HOBt (0.521 g), N-isopropylethylenediamine (0.353 g), and triethylamine (1 ml). After stirring at room temperature for 18 hr, the reaction mixture was diluted with water and extracted with ethyl acetate. The organic layer was washed with 10% aqueous potassium carbonate and saturated aqueous sodium chloride sequentially, dried, and concentrated. The residue was recrystallized from ethanol to obtain the titled compound (0.806 g).

m.p.:150–154° C.

EXAMPLE 24

2-(N,N-Diethylamino)ethyl-4-[(4-biphenylyl)carbonyl]amino]benzoate

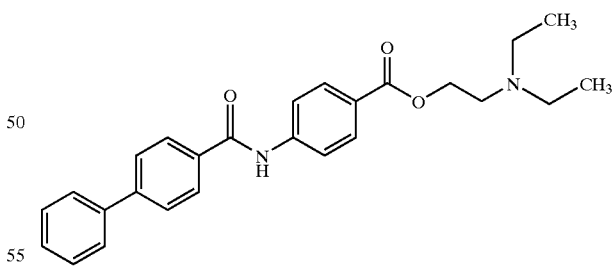

To a solution of 4-biphenylcarboxylic acid (1.091 g) in THF (15 ml) in an ice bath were added oxalyl chloride (0.39 ml) and DMF (one drop). The reaction mixture was stirred at room temperature for 30 min and concentrated. The residue was dissolved in THF (10 ml), which was added to the suspension of procaine hydrochloride (1.091 g) and triethylamine (0.67 ml) in THF (30 ml) at 0° C. After stirring at 0° C. for 30 min, the reaction mixture was diluted with 10% aqueous potassium carbonate and, extracted with ethyl acetate. The organic layer was washed with saturated aqueous sodium chloride, dried, and concentrated. The residue was recrystallized from ethyl acetate to obtain the titled compound (0.728 g).

m.p.:146–149° C.

EXAMPLE 25

N-[4-({[2-(Dimethylamino)ethyl]amino}carbonyl)phenyl](4-biphenylyl)carboxamide

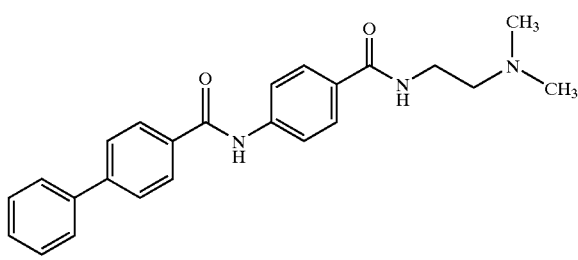

To a solution of 4-(4-biphenylylcarbonylamino)benzoic acid (0.323 g) in THF (15 ml)/acetonitrile (15 ml) were added WSC (0.248 g), HOBt (0.156 g), N,N-dimethylethylenediamine (0.097 g), and triethylamine (0.21 ml). After stirring at room temperature for 18 hr, the reaction mixture was diluted with water and extracted with ethyl acetate. The organic layer was washed with 10% aqueous potassium carbonate and saturated aqueous sodium chloride sequentially, dried, and concentrated. The residue was recrystallized from methanol/diethyl ether to obtain the titled compound (0.100 g).

m.p.:261–264° C. (decomposed).

The following compounds in Example 26 and 27 were prepared by the procedure similar to Example 25.

EXAMPLE 26

N-[4-{[2-(Piperidinoethyl)amino]carbonyl}phenyl](4-biphenylyl)carboxamide

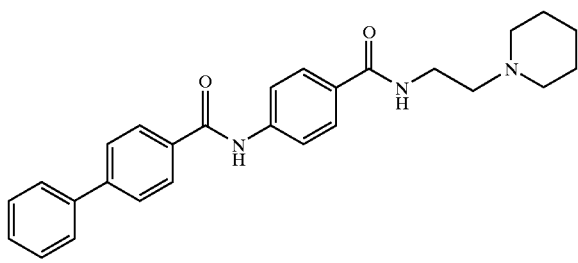

m.p.:247–252° C. (decomposed).

EXAMPLE 27

N-[4-{[2-(1-Pyrrolidinyl)ethyl]amino}carbonyl}phenyl](4-5 biphenylyl)carboxamide

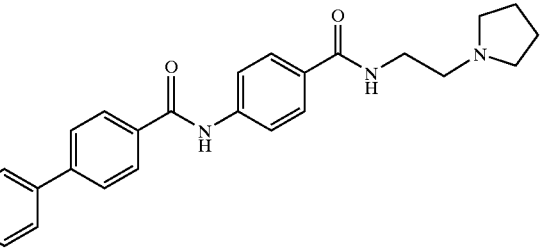

m.p.:241–245° C. (decomposed).

Formulation Example 1

| | |
|---|---|
| (1) Compound obtained in Example 8 | 50 mg |
| (2) Lactose | 34 mg |
| (3) Corn starch | 10.6 mg |
| (4) Corn starch (pasty) | 5 mg |
| (5) Magnesium stearate | 0.4 mg |
| (6) Carboxymethyl cellulose calcium | 20 mg |
| Total | 120 mg |

These components (1) to (6) were mixed according to a conventional manner, and tabletted, using a tabletting machine, to obtain tablets.

Experimental Example 1

Compounds of the present invention were tested for an inhibitory activity of the production and/or secretion of amyloid-β protein (references: Science, 264, 1336 (1994) and Biochemistry, 34, 10272 (1995)).

(Methods)

a) Materials Used

Human neuroblastoma IMR-32 cells: purchased from American Type Culture Center.

Dulbecco's modified Eagle's medium (hereinafter abbreviated to DMEM): purchased from Nissui Pharmaceutical Co., Ltd.

Fetal calf serum (hereinafter abbreviated to FCS) and a mixture of penicillin (5000 U/ml)/streptomycin (5 mg/ml): purchased from Bio Whittaker Co.

Phosphate buffered saline (hereinafter abbreviated to PBS): purchased from Flow Laboratories Co.

Block Ace (trade name): Purchased from Dai-Nippon Pharmaceutical Co.

Bovine serum albumin (hereinafter abbreviated to BSA): purchased from Sigma Co.

Cultivation flask: manufactured by Falcon Co.

48-well Plate: manufactured by Coaster Co.

Standard $A\beta_{1-40}$ and $A\beta_{1-42}$: purchased from Bachem Co.

The other reagents used were commercially available ones of special grade.

b) Test Method (1) Cultivation of IMR-32 Cells

IMR-32 cells were cultivated in a flask (Falcon, 750 ml) containing 10% FCS/DMEM medium, in an atmosphere of 10% CO$_2$/90% air, at 37° C. to be in confluence. The cultured cells were seeded into a 48-well plate in a density of 2.5×10$^5$ cells/well, and incubated therein for 3 days under the same conditions as above. Then, the culture medium was removed through suction.

A DMF solution containing a test compound was dissolved in 0.5 ml of 0.5% BSA/DMEM, and added to the plate, and the cells were incubated for further 24 hours. As the control, the same volume of DMF but not containing the test compound was dissolved in 0.5 ml of 0.5% BSA/DMEM, and added to the plate.

The supernatant was collected for the plate, and stored at −20° C. of lower until the measurement of its Aβ content.

(2) Enzyme Immunoassay (EIA) for Aβ

BAN-50 antibody or BNT-77 antibody was used as the primary antibody. To determine the Aβ$_{1-40}$, BA-27 antibody was used as the secondary antibody. To determined the Aβ$_{1-42}$, BC-05 was used as the secondary antibody.

BAN-50 antibody or BNT antibody was dissolved in 0.1 M carbonic acid buffer (pH 9.6) in a concentration of 15 μg/ml was added to a polyethylene microtiter plate in an amount of 100 μl/well, and kept at 4° C. overnight. The surface of the plate was washed three times with PBS, and 200 μl of a blocking solution (25% Block Ace/0.1% sodium azide/PBS) was added to the plate. Under this condition, the plate was kept at 4° C. before the addition thereto of the supernatant prepared in the above (1).

Just before the addition of the supernatant, the surface of the plate was washed three times with PBS, and 50 μl of a buffer for primary reaction (20 mM phosphate buffer, pH 7.0; 400 mM NaCl; 2 mM EDTA; 10% Block Ace; 0.2% BSA; 0.05% sodium azide) was added to the plate. Further, 100 μl of the supernatant and 100 μl of standard Aβ$_{1-40}$ or Aβ$_{1-42}$ a diluted in the buffer for primary reaction (to have a varying concentration of 1000, 200, 40 or 8 pg/ml) were added to the plate, and then kept overnight at 4° C.

The plate was washed three times with PBS, and 100 μl of an HRP-labeled secondary antibody (BA-27 antibody or BC-o5 antibody labeled with HRP: horseradis peroxidase) as dissolved in a buffer for secondary reaction (20 mM phosphate buffer, pH 7.0; 400 mM NaCl; 2 mM EDTA; 1% BSA) was added thereto. After having been left at room temperature for 6 hours, the plate was washed seven times with PBS, and 100 μl of a coloring reagent (TMB Peroxidase Substrate, trade name, manufactured by Kirkegaard & Perry Lab.) was added thereto. This was left at room temperature for 8 to 10 minutes, and 100 μl of 1 M phosphoric acid solution was added to the plate to stop the reaction. Then, using a plate reader (MTP-32 Microplate Reader, by Corona Co.), the sample on the plate was subjected to calorimetric determination (at 450 nm).

(Results)

Four wells were used for one dose of the test compound.

The activity of the test compound (10 μM) to inhibit the production and/or secretion of Aβ$_{1-40}$ and Aβ$_{1-42}$ was obtained in terms of the percentage (%) relative to the control. The results are shown in Table 1.

TABLE 1

| Test compound (Ex. No.) | Aβ1-40 (%) | Aβ1-42 (%) |
|---|---|---|
| Example 8 | 39 | 63 |

The above results confirm that the compound (I) and (Ia) of the present invention have the inhibitory activity of production and/or secretion of amyloid-β protein.

INDUSTRIAL UTILITY

Since the compound (I) has an excellent inhibitory activity of the production and/or secretion of amyloid-β protein and thus is useful for the prevention and/or the treatment of diseases caused by amyloid-β (e.g., senile dementia, Alzheimer's disease, Down's syndrome, Parkinson's disease, disease, amyloid angiopathy or disorders caused by amyloid-β protein in cerebrovascular disorders). Compound (Ia) also has the excellent inhibitory activity for the production and or secretion of amyloid-β protein.

What is claimed is:

1. An amyloid-β protein production and/or secretion inhibitor which comprises a compound of the formula:

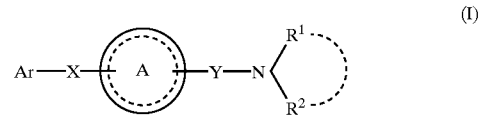

wherein Ar is an aromatic ring assembly group which may be substituted; X is a bivalent group selected from —O—, —S—, —CO—, —SO—, —SO$_2$—, —NR$^8$—, —CONR$^8$—, SO$_2$NR$^8$ and —COO— wherein R$^8$ hydrogen atom, a hydrocarbon group which may be substituted or acyl, or a bivalent C$_{1-6}$ aliphatic hydrocarbon group which may contain one or two of said bivalent groups; Y is [1] a group represented by the formula: —(CH$_2$)$_{q1}$CONR$^9$ (CH$_2$)$_{r1}$— wherein each of q$^1$ and r$^1$ is an integer of 0 to 3 and their sum is an integer of not more than 3, R$^9$ is hydrogen atom or C$_{1-6}$ alkyl which may be halogenated or C$_{1-6}$ alkyl-carbonyl which may be halogenated, or [2] a group represented by the formula: —(CH$_2$)$_{q2}$COO (CH$_2$)$_{r2}$— wherein each of q$^2$ and r$^2$ is an integer of 0 to 3 and their sum is not more than 3; R$^1$ and R$^2$ are hydrogen atom or C$_{1-6}$ alkyl which may be substituted, or R$^1$ and R$^2$ may form, together with the adjacent nitrogen atom, a nitrogen-containing heterocyclic ring which may be substituted; and ring A is a phenylene, provided that 4,4'-[[1,1'-biphenyl]-2,5-diylbis(oxy)]bis[benzoic acid] dihydrazide is excluded, or a salt thereof.

2. The inhibitor according to claim 1, wherein Ar is: an aromatic ring assembly group formed by removing any one of hydrogen atoms from an aromatic ring assembly of 2 or 3 rings of [1] C$_{6-14}$ monocyclic or bi- or tricyclic aromatic hydrocarbon aromatic ring or [2] 5- to 14-membered aromatic heterocyclic ring having, in addition to carbon atom, 1 to 4 hetero atoms selected from nitrogen atom, sulfur atom and oxygen atom, or rings formed by the aromatic heterocyclic ring fused together with 1 or 2 benzene rings, said rings being bound to each other directly through a single bond, and the number of the bonds which bind the rings directly being smaller than the number of the rings by 1, which may be substituted with 1 to 5 substituents selected from the group consisting of (i) halogen atom, (ii) C$_{1-3}$ alkylenedioxy, (iii) nitro, (iv) cyano, (v) C$_{1-6}$ alkyl which may be halogenated, (vi) C$_{6-10}$ aryloxy-C$_{1-6}$ alkyl, (vii) C$_{1-6}$ alkyl-C$_{6-10}$ aryl-C$_{2-6}$ alkenyl, (viii) C$_{3-6}$ cycloalkyl which may be halogenated, (ix) C$_{7-16}$ aralkyl which may be substituted with 1 to 5 substituents selected from the group consisting of (a) halogen atom, (b) C$_{1-3}$ alkylenedioxy, (c) nitro, (d) cyano, (e) C$_{1-6}$ alkyl which may be halogenated, (f) C$_{3-6}$ cycloalkyl which may be halogenated, (g) C$_{1-6}$ alkoxy which may be halogenated, (h) C$_{1-6}$ alkylthio which may be halogenated, (i) hydroxy, (j) amino, (k) mono- $C_{1-6}$ alkylamino, (l) di-$C_{1-6}$ alkylamino, (m) formyl, (n) carboxy, (o) carbamoyl, (P) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (x) $C_{1-6}$ alkoxy which may be halogenated, (xi) $C_{1-6}$ alkylthio which may be halogenated, (xii) hydroxy, (xiii) $C_{6-10}$ aryloxy which may be substituted with 1 to 5 substituents selected from the group consisting of (a) halogen atom, (b) $C_{1-3}$ alkylenedioxy, (c) nitro, (d) cyano, (e) $C_{1-6}$ alkyl which may be halogenated, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (P) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (xiv) $C_{6-10}$ aryl-$C_{7-16}$ aralkyloxy, (xv) amino, (xvi) mono-$C_{1-6}$ alkylamino, (xvii) di-$C_{1-6}$ alkylamino, (xviii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (P) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{6-10}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [6] $C_{1-6}$ alkyl-carbonyl which may be halogenated, and [7] $C_{1-6}$ alkyl-sulfonyl, (xix) acyl represented by the formula: —CO—$R^3$, —CO—$OR^3$, —CO—$NR^3 R^4$, —CS—$NHR^3$—$SO_2$—$R^{3a}$ or —SO—$R^{3a}$ wherein $R^3$ is hydrogen atom, or $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (Y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^{3a}$ is $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^4$ is hydrogen atom or $C_{1-6}$ alkyl, or $R^3$ and $R^4$ may form, together with the adjacent nitrogen atom, 5- to 7-membered nitrogen-containing heterocyclic ring having, in addition to carbon atom, at least one nitrogen atom, which may further have 1 to 3 hetero atoms selected from nitrogen atom, sulfur atom and oxygen atom, (xx) acylamino represented by the formula: $-NR^5-COR^6-NR^5-COOR^{6a}$, $-NR^5-SO_2RR^{6a}$ or $-NR^5-CONR^{6a}R^{6b}$ wherein $R^5$ is hydrogen atom or $C_{1-6}$ alkyl, $R^6$ is as defined for $R^3$, $R^{6a}$ is as defined for $R^{3a}$, $R^{6b}$ is as defined for $R^4$ and (xxi) acyloxy represented by the formula: $-O-COR^7$, $-O-COOR^7$ or $-O-CONHR^7$ wherein $R^7$ is as defined for $R^3$, X is a bivalent group selected from $-O-$, $-S-$, $-CO-$, $-SO-$, $-SO_2-$, $-NR^8-$, $-CONR^8-$, $-SO_2NR^8-$ and $-COO-$ wherein $R^8$ is (1) hydrogen atom, (2) $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{3-6}$ aryl or $C_{7-19}$ aralkyl, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated (ix) hydroxy, (x) amino, (xiii) [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_6$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z)

$C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{18}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyloxy which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, (3) acyl represented by the formula: —CO—$R^3$, —CO—$OR^3$, —CO—$NR^3R^4$, —CS—$NHR^3$, —$SO_2$—$R^{3a}$ or —SO—$R^{3a}$ wherein $R^3$ is hydrogen atom, or $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^{3a}$ is $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the' group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^4$ is hydrogen atom or $C_{1-6}$ alkyl, or $R^3$ and $R^4$ may form, together with the adjacent nitrogen atom, 5- to 7-membered nitrogen-containing heterocyclic ring having, in addition to carbon atom, at least one nitrogen atom, which may further have 1 to 3 hetero atoms selected from nitrogen atom, sulfur atom and oxygen atom], or $C_{1-6}$ alkylene, $C_{2-6}$ alkenylene or $C_{2-6}$ alkynylene which may contain one or two these bivalent groups, and $R^1$ and $R^2$ are (1) hydrogen atom, (2) $C_{1-6}$ alkyl which may substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) formyl, (xiv) carboxy, (xv) carbamoyl, (xvi) $C_{1-6}$ alkyl-carbonyl which may be halogenated, (xvii) $C_{1-6}$ alkoxy-carbonyl, (xviii) mono-$C_{1-6}$ alkyl-carbamoyl, (xix) di-$C_{1-6}$ alkyl-carbamoyl, (xx) $C_{1-6}$ alkylsulfonyl which may be halogenated, (xxi) formylamino, (xxii) $C_{1-6}$ alkyl-carboxamido which may be halogenated, (xxiii) $C_{1-6}$ alkoxy-carboxamido, (xxiv) $C_{1-6}$ alkylsulfonylamino, (xxv) $C_{1-6}$ alkyl-carbonyloxy, (xxvi) $C_{1-6}$ alkoxy-carbonyloxy, (xxvii) mono-$C_{1-6}$ alkyl-carbamoyloxy, (xxviii) di-$C_{1-6}$ alkyl-carbamoyloxy, and (xxix) the same group as that of Ar, or $R^1$ and $R^2$ may form, together with the adjacent nitrogen atom, 3- to 8-membered nitrogen-containing heterocyclic ring having, in addition to carbon atom, at least one nitrogen atom, which may further have 1 to 3 hetero atoms selected from nitrogen, sulfur atom and oxygen atom, and which may be substituted with 1 to 3 substituents selected from the group consisting of (i) $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (ii) $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iii) 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iv) $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1,6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (v) $C_{1-6}$ alkyl-carbonyl which may be halogenated, and (vi) $C_{1-6}$ alkyl-sulfonyl.

3. The inhibitor according to claim 1, wherein the aromatic ring assembly group is 2-, 3- or 4-biphenylyl.

4. The inhibitor according to claim 1, wherein Ar is biphenylyl group which may be substituted with halogen atom.

5. The inhibitor according to claim 1, wherein X is [1] a group represented by the formula: —$(CH_2)_{p1}O$— wherein $p^1$ is an integer of 1 to 3, [2] —$(CH_2)_{p2}$— wherein $p^2$ is an integer of 1 to 3, [3] $(CH_2)_{p3}OCONH$— wherein $p^3$ is an integer of 1 to 3, [4] CONH or [5] $SO_2NH$.

6. The inhibitor according to claim 1, wherein X is a group represented by the formula: —$(CH_2)_{p1}O$— wherein $p^1$ is an integer of 1 to 3.

7. The inhibitor according to claim 1, wherein Y is a group represented by the formula: —$(CH_2)_{q1}CONR^9(CH_2)_{r1}$— wherein each of $q^1$ and $r^1$ is an integer of 0 to 3 and their sum is an integer of not more than 3, $R^9$ is hydrogen atom or $C_{1-6}$ alkyl-carbonyl.

8. The inhibitor according to claim 1, wherein each of $R^1$ and $R^2$ is [1] hydrogen atom or [2] $C_{1-6}$ alkyl which may be substituted with carboxyl or $C_{1-6}$ alkoxy-carbonyl, or $R^1$ and $R^2$ form, together with the adjacent nitrogen atom, a 5- or 6-membered nitrogen-containing heterocyclic ring.

9. The inhibitor according to claim 1, wherein Ar is biphenylyl which may be substituted with halogen atom, X is [1] a group represented by the formula: —$(CH_2)_{p1}$O— wherein $p^1$ is an integer of 1 to 3, [2] —$(CH_2)_{p2}$— wherein $p^2$ is an integer of 1 to 3, [3] $(CH_2)_{p3}$OCONH— wherein $p^3$ is an integer of 1 to 3, [4] CONH or [5] $SO_2NH$, and each of $R^1$ and $R^2$ is [1] hydrogen atom or [2] $C_{1-36}$ alkyl which may be substituted with carboxy, $C_{1-6}$ alkoxy-carbonyl or di-$C_{1-6}$ alkylnitrile, or $R^1$ and $R^2$ form, together with the adjacent nitrogen atom, a 5- or 6-membered nitrogen-containing heterocyclic ring.

10. The inhibitor according to claim 1, wherein Ar is biphenylyl which may be substituted with halogen atom, X is a group represented by the formula: —$(CH_{2p1}$O— wherein $p^1$ is an integer of 1 to 3, CONH or $SO_2NH$, Y is —CONH$(CH_2)_s$— wherein s is an integer of 1 to 3 or —COO$(CH_2)_t$— wherein t is an integer of 1 to 3, and each of $R^1$ and $R^2$ is hydrogen atom or $C_{1-6}$ alkyl, or $R^1$ and $R^2$ form, together with the adjacent nitrogen atom, a 5- or 6-membered nitrogen-containing heterocyclic ring.

11. The inhibitor according to claim 1, wherein the compound is 5-chloro-N-[2-N,N-diethylamino)ethyl]-2-methoxy-4-(1-naphthoylamino)benzamide,
5-chloro-N-[2-N,N-diethylamino)ethyl]-2-methoxy-4-(2-naphthoylamino)benzamide,
5-chloro-N-[2-N,N-diethylamino)ethyl]-2-methoxy-4-(1-naphthylsulfonylamino)benzamide,
5-chloro-N-[2-N,N-diethylamino)ethyl]-2-methoxy-4-(2-naphthylsulfonylamino)benzamide,
N-[3-[4-(2-naphthylmethoxy)phenyl]propyl]-N,N-dipropylamine hydrochloride,
N-[3-[4-[(2,4-dichlorobenzyl)oxy]phenyl]propyl]-N,N-dipropylamine hydrochloride,
N-[4-(2-naphthylmethoxy)phenethyl]-N,N-dipropylamine hydrochloride,
N-[4-(2,4-dichlorobenzyl)oxy]phenethyl]-N,N-dipropylamine hydrochloride,
N-[4-(4-biphenylylmethoxy)phenethyl]-N,N-dipropylamine hydrochloride,
N-[2-(2-naphthylmethoxy)phenethyl]-N,N-dipropylamine hydrochloride,
N-[3-(2-naphthylmethoxy)phenethyl]-N,N-dipropylamine hydrochloride,
N-[3-(4-biphenylylmethoxy)phenethyl]-N,N-dipropylamine hydrochloride,
N-[3-[(2,4-dichlorobenzyl)oxy]phenethyl]-N,N-dipropylamine hydrochloride,
N-[3-(1-naphthylmethoxy)phenethyl]-N,N-dipropylamine hydrochloride,
4-(4-biphenylylmethoxy)phenyl-N-(2-piperidinoethyl)-acetamide,
4-(4-biphenylylmethoxy)phenyl-N-[2-(N,N-dimethylamino)-ethyl]acetamide,
6-(4-biphenylylmethoxy)-N-[2-(pyrrolidine-1-yl)ethyl]-nicotinamide,
1-(4-biphenylylmethyl)-1,6-dihydro-6-oxo-N-[2-(pyrrolidine-1-yl)ethyl]-3-pyridinecarboxamide,
1-(4-biphenylylmethyl)-1,6-dihydro-6-oxo-N-(2-(piperidinoethyl)-3-pyridinecarboxamide,
6-(4-biphenylylmethoxy)-N-(2-piperidinoethyl) nicotinamide,
6-(4-biphenylylmethoxy)-N-[2-(N,N-dimethylamino) ethyl]-nicotinamide,
4-(4-biphenylylmethoxy)-N-(2-piperidinoethyl)benzamide,
4-(4-biphenylylmethoxy)-N-[(2-pyrrolidine-1-yl)ethyl]-benzamide,
2-piperidinoethyl=4-(4-biphenylylethoxy)benzoate,
2-(pyrrolidin-1-yl)ethyl=4-(4-biphenylylmethoxy)benzoate,
4-[4-(biphenylylmethoxy)phenyl]-N-[2-(N,N-dimethylamino)-ethyl]acetamide oxalate,
4-[4-(biphenylylmethoxy)phenyl]-N-[2-(N,N-dimethylamino)-ethyl]acetamide maleate,
4-[4-(biphenylylmethoxy)phenyl]-N-[2-(N,N-dimethylamino)-ethyl]acetamide fumarate,
4-[4-(biphenylylmethoxy)phenyl]-N-[2-(N-methylamino)-ethyl]acetamide hydrochloride,
4-[4-(biphenylylmethoxy)phenyl]-N-[2-(N-methylamino)-ethyl]acetamide,
ethyl 7-[2-[4-[(4-biphenylylmethoxy)phenyl]acetylamino-ethyl](methyl)amino]heptanoate,
7-[2-[4-[4-(biphenylylmethoxy)phenyl]acetylaminoethyl]-(methyl)amino]heptanoic acid hydrochloride,
N-(4-(2-((2-(dimethylamino)ethyl)(methyl)amino)-2-oxoethyl)phenyl)[1,1'-biphenyl]-4-carboxamido,
N-(2-aminoethyl)-2-(4-([1,1'-biphenyl]-4-ylmethoxy) phenyl)-acetamide hydrochloride,
4-([1,1'-biphenyl]-4-ylmethoxy)-N-(2-(1-pyrrolidinyl)-ethyl)benzamide,
N-(4-(2-((2-dimethylamino)ethyl)(methyl)amino)-2-oxoethyl)phenyl)[1,1'-biphenyl]-4-carboxamide,
N-[4-({[2-(diethylamino)ethyl]amino}carbonyl)phenyl](4-biphenylyl)carboxamide,
4-(4-biphenylyl)methoxy)-N-[2-(isopropylamino)ethyl]-benzamide,
2-(N,N-diethylamino)ethyl-4-[(4-biphenylyl)carbonyl]amino]-benzoate,
N-[4-({[2-(dimethylamino)ethyl]amino}carbonyl)phenyl](4-biphenylyl)carboxamide,
N-[4-{[2-(piperidinoethyl)amino]carbonyl}phenyl](4-biphenylyl)carboxamide, or
N-[4-({[2-(pyrrolidinyl)ethyl]amino}carbonyl)phenyl](4-biphenylyl)carboxamide.

12. A compound represented by the formula:

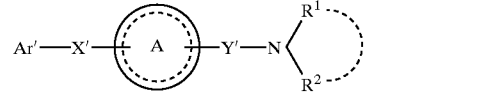

(Ia)

wherein
Ar' is an aromatic ring assembly group which may be substituted,
X' is [1] a group represented by the formula: —$(CH_2)_{p1}$O— wherein $p^1$ is an integer of 1 to 3, [2] —$(CH_2)_{p2}$— wherein $p^2$ is an integer of 1 to 3 or [3] CONH,
Y' is [1] a group represented by the formula: —$(CH_2)_{q1}$CONR$_9$$(CH_2)_{r1}$— wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated, or [2] a group represented by the formula: —$(CH_2)_{q2}$COO$(CH_2)_{r2}$— wherein each of $q^2$ and $r^2$ is an integer of 0 to 3 and their sum is not more than 3, each of $R^1$ and $R^2$ is hydrogen atom or $C_{1-6}$ alkyl which may be substituted, or $R^1$ and $R^2$ may form, together with the adjacent nitrogen atom, a nitrogen-containing heterocyclic ring, and ring A is a phenylene, provided that 4,4'-[[1,1'-biphenyl]-2,5-diylbis(oxy)]bis[benzoic acid] dihydrazide is excluded.

13. The compound according to claim 12, wherein Ar' is:
an aromatic ring assembly group formed by removing any one of hydrogen atoms from an aromatic ring assembly of 2 or 3 rings of [1] $C_{6-14}$ monocyclic or bi- or tricyclic aromatic hydrocarbon aromatic ring or [2] 5- to 14-membered aromatic heterocyclic ring having, in addition to carbon atom, 1 to 4 hetero atoms selected from nitrogen atom, sulfur atom and oxygen atom, or rings formed by the aromatic heterocyclic ring fused together with 1 or 2 benzene rings, said rings being bound to each other directly through a single bond, and the number of the bonds which bind the rings directly being smaller than the number of the rings by 1, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{6-10}$ aryloxy-$C_{1-6}$ alkyl, (vii) $C_{1-6}$ alkyl-$C_{6-10}$ aryl-$C_{2-6}$ alkenyl, (viii) $C_{3-6}$ cycloalkyl which may be halogenated, (ix) $C_{7-16}$ aralkyl which may be substituted with 1 to 5 substituents selected from the group consisting of (a) halogen atom, (b) $C_{1-3}$ alkylenedioxy, (c) nitro, (d) cyano, (e) $C_{1-6}$ alkyl which may be halogenated, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (x) $C_{1-6}$ alkoxy which may be halogenated, (xi) $C_{1-6}$ alkylthio which may be halogenated, (xii) hydroxy, (xiii) $C_{6-10}$ aryloxy which may be substituted with 1 to 5 substituents selected from the group consisting of (a) halogen atom, (b) $C_{1-3}$ alkylenedioxy, (c) nitro, (d) cyano, (e) $C_{1-6}$ alkyl which may be halogenated, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (xiv) $C_{6-10}$ aryl-$C_{7-16}$ aralkyloxy, (xv) amino, (xvi) mono-$C_{1-6}$ alkylamino, (xvii) di-$C_{1-6}$ alkylamino, (xviii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamolyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xix) acyl represented by the formula: —CO—$R^3$, —CO—$OR^3$, —CO—$NR^3R^4$, —CS—$NHR^3$, —$SO_2$—$R^{3a}$ or —SO—$R^{3a}$ wherein $R^3$ is hydrogen atom, or $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^{3a}$ is $C_{1-6}$ alkyl, $C_{2-6}$ alkenyl, $C_{2-6}$ alkynyl, $C_{3-6}$ cycloalkyl, a fused ring of $C_{3-6}$ cycloalkyl and a benzene ring, $C_{6-14}$ aryl, $C_{7-19}$ aralkyl or 5- to 14-membered heterocyclic group having, in addition to carbon atom, 1 to 4 hetero atoms selected from nitrogen atom, sulfur atom and oxygen atom, which may be substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) 5- to 7-membered saturated cyclic amino which may be substituted with 1 to 3 substituents selected from the group consisting of [1] $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j)

amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [2] $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1,6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [3] 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [4] $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{01-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, [5] $C_{1-6}$ alkyl-carbonyl which may be halogenated, and [6] $C_{1-6}$ alkyl-sulfonyl, (xiv) formyl, (xv) carboxy, (xvi) carbamoyl, (xvii) $C_{1-6}$ alkyl-carbonyl carbonyl which may be halogenated, (xviii) $C_{1-6}$ alkoxy-carbonyl, (xix) $C_{6-10}$ aryl-carbonyl, (xx) $C_{6-10}$ aryloxy-carbonyl, (xxi) $C_{7-16}$ aralkyloxy-carbonyl, (xxii) mono-$C_{1-6}$ alkyl-carbamoyl, (xxiii) di-$C_{1-6}$ alkyl-carbamoyl, (xxiv) $C_{6-10}$ arylcarbamoyl, (xxv) $C_{1-6}$ alkylsulfonyl which may be halogenated, (xxvi) $C_{6-10}$ arylsulfonyl, (xxvii) formnylamino, (xxviii) $C_{1-6}$ alkyl-carboxamido which may be halogenated, (xxix) $C_{6-10}$ aryl-carboxamido, (xxx) $C_{1-6}$ alkoxy-carboxamido, (xxxi) $C_{1-6}$ alkylsulfonylamino, (xxxii) $C_{1-6}$ alkyl-carbonyloxy, (xxxiii) $C_{6-10}$ aryl-carbonyloxy, (xxxiv) $C_{1-6}$ alkoxy-carbonyloxy, (xxxv) mono-$C_{1-6}$ alkyl-carbamoyloxy, (xxxvi) di-$C_{1-6}$ alkyl-carbamoyloxy, (xxxvii) $C_{6-10}$ aryl-carbamoyloxy, (xxxviii) nicotinoyloxy and (xxxix) $C_{6-10}$ aryloxy, $R^4$ is hydrogen atom or $C_{1-6}$ alkyl, or $R^3$ and $R^4$ may form, together with the adjacent nitrogen atom, 5- to 7-membered nitrogen-containing heterocyclic ring having, in addition to carbon atom, at least one nitrogen atom, which may further have 1 to 3 hetero atoms selected from nitrogen atom, sulfur atom and oxygen atom, (xx) acylamino represented by the formula: —$NR^5$—$COR^6$, —$NR^5$—$COOR^{6a}$, —$NR^5$—$SO_2RR^{6a}$ or —$NR^5$—$CONR^{6a}R^{6b}$ wherein $R^5$ is hydrogen atom or $C_{1-6}$ alkyl, $R^6$ is as defined for $R^3$, $R^{6a}$ is as defined for $R^{3a}$, $R^{6b}$ is as defined for $R^4$ and (xxi) acyloxy represented by the formula: —O—$COR^7$, —O—$COOR^7$ or —O—$CONHR^7$ wherein $R^7$ is as defined for $R^3$, and $R^1$ and $R^2$ are (1) hydrogen atom, (2) $C_{1-6}$ alkyl which may substituted with 1 to 5 substituents selected from the group consisting of (i) halogen atom, (ii) $C_{1-3}$ alkylenedioxy, (iii) nitro, (iv) cyano, (v) $C_{1-6}$ alkyl which may be halogenated, (vi) $C_{3-6}$ cycloalkyl which may be halogenated, (vii) $C_{1-6}$ alkoxy which may be halogenated, (viii) $C_{1-6}$ alkylthio which may be halogenated, (ix) hydroxy, (x) amino, (xi) mono-$C_{1-6}$ alkylamino, (xii) di-$C_{1-6}$ alkylamino, (xiii) formyl, (xiv) carboxy, (xv) carbamoyl, (xvi) $C_{1-6}$ alkyl-carbonyl which may be halogenated, (xvii) $C_{1-6}$ alkoxy-carbonyl, (xviii) mono-$C_{1-6}$ alkyl-carbamoyl, (xix) di-$C_{1-6}$ alkyl-carbamoyl, (xx) $C_{1-6}$ alkylsulfonyl which may be halogenated, (xxi) formylamino, (xxii) $C_{1-6}$ alkyl-carboxamido which may be halogenated, (xxiii) $C_{1-6}$ alkoxy-carboxamido, (xxiv) $C_{1-6}$ alkylsulfonylamino, (xxv) $C_{1-6}$ alkyl-carbonyloxy, (xxvi) $C_{1-6}$ alkoxy-carbonyloxy, (xxvii) mono-$C_{1-6}$ alkyl-carbamoyloxy, (xxviii) di-$C_{1-6}$ alkyl-carbamoyloxy, and (xxix) the same group as that of Ar, $R^1$ and $R^2$ may form, together with the adjacent nitrogen atom, 3- to 8-membered nitrogen containing heterocyclic ring having, in addition to carbon atom, at least one nitrogen atom, which may further have 1 to 3 hetero atoms selected from nitrogen, sulfur atom and oxygen atom and which may be substituted with 1 to 3 substituents selected from the group consisting of (i) $C_{6-14}$ aryl which may be substituted with 1 to 5 substituents selected from the group consisting of (a) $C_{1-6}$ alkyl which may be halogenated, (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r)

mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (ii) $C_{7-19}$ aralkyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iii) 5 to 10 membered aromatic heterocyclic group having, in addition to carbon atom, 1 to 3 hetero atoms selected from nitrogen atom, oxygen atom and sulfur atom which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (iv) $C_{6-14}$ aryl-carbonyl which may be substituted with 1 to 5 substituents selected from the group consisting of (a) $C_{1-6}$ alkyl which may be halogenated (b) halogen atom, (c) $C_{1-3}$ alkylenedioxy, (d) nitro, (e) cyano, (f) $C_{3-6}$ cycloalkyl which may be halogenated, (g) $C_{1-6}$ alkoxy which may be halogenated, (h) $C_{1-6}$ alkylthio which may be halogenated, (i) hydroxy, (j) amino, (k) mono-$C_{1-6}$ alkylamino, (l) di-$C_{1-6}$ alkylamino, (m) formyl, (n) carboxy, (o) carbamoyl, (p) $C_{1-6}$ alkyl-carbonyl which may be halogenated, (q) $C_{1-6}$ alkoxy-carbonyl, (r) mono-$C_{1-6}$ alkyl-carbamoyl, (s) di-$C_{1-6}$ alkyl-carbamoyl, (t) $C_{1-6}$ alkylsulfonyl which may be halogenated, (u) formylamino, (v) $C_{1-6}$ alkyl-carboxamido which may be halogenated, (w) $C_{1-6}$ alkoxy-carboxamido, (x) $C_{1-6}$ alkylsulfonylamino, (y) $C_{1-6}$ alkyl-carbonyloxy, (z) $C_{1-6}$ alkoxy-carbonyloxy, (aa) mono-$C_{1-6}$ alkyl-carbamoyloxy and (bb) di-$C_{1-8}$ alkyl-carbamoyloxy, (v) $C_{1-6}$ alkyl-carbonyl which may be halogenated, and (vi) $C_{1-6}$ alkyl-sulfonyl.

14. The compound according to claim 12, wherein the aromatic ring assembly group represented by Ar' is 2-, 3- or 4-biphenylyl.

15. The compound according to claim 12, wherein X' is a group represented by —$CH_2)_{p1}$O— wherein $p^1$ is an integer of 1 to 3.

16. The compound according to claim 12, wherein Y' is a group represented by the formula: —$(CH_2)_{q1}CONR^9(CH_2)_{r1}$— wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated.

17. The compound according to claim 12, wherein each of $R^1$ and $R^2$ is [1] hydrogen atom or [2] $C_{1-6}$ alkyl which may be substituted with carboxy or $C_{1-6}$ alkoxy-carbonyl, or $R^1$ and $R^2$ form, together with the adjacent nitrogen atom, a 5- or 6-membered nitrogen-containing heterocyclic ring.

18. The compound according to claim 12, wherein Ar' is 2-, 3- or 4-biphenylyl, X' is [1] a group represented by the formula: —$(CH_2)_{p1}$O— wherein $p^1$ is an integer of 1 to 3, [2] —$(CH_2)_{p2}$— wherein $p^2$ is an integer of 1 to 3 or [3] CONH, Y' is [1] a group represented by the formula: —$(CH_2)^{q1}$ $CONR^9(CH_2)_{r1}$— wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated, or [2] a group represented by the formula: —$(CH_2)_{q2}COO(CH_b{}_2)_{r2}$— wherein each of $q^2$ and $r^2$ is an integer of 0 to 3 and their sum is not more than 3, and each of $R^1$ and $R^2$ is [1] hydrogen atom or [2] $C_{1-6}$ alkyl which may be substituted with carboxy, $C_{1-6}$ alkoxy-carbonyl or di-$C_{1-6}$ alkylnitrile, or $R^1$ and $R^2$ may form, together with the adjacent nitrogen atom, a 5- or 6-membered nitrogen-containing heterocyclic ring.

19. The compound according to claim 12, wherein Ar' is biphenylyl, X' is —$(CH_2)_{p1}$O— wherein $p^1$ is an integer of 1 to 3, Y' is —$CONH(CH_2)_s$— wherein s is an integer of 1 to 3, and $R^1$ and $R^2$ are $C_{1-6}$ alkyl, or $R^1$ and $R^2$ form, together with the adjacent nitrogen atom, a 5- or 6-membered nitrogen-containing heterocyclic ring.

20. 4-(4-biphenylylmethoxy)phenyl-N-(2-piperidinoethyl)acetamide, 4-(4-biphenylylmethoxy)phenyl-N-[2-(N,N-dimethylamino)-ethyl]acetamide, 6-(4-biphenylylmethoxy)-N-[2-(pyrrolidine-1-yl)ethyl]-nicotinamide, 1-(4-biphenylylmethyl)-1,6-dihydro-6-oxo-N-[2-(pyrrolidine-1-yl)ethyl]-3-pyridinecarboxamido, 1-(4-biphenylylmethyl)-1,6-dihydro-6-oxo-N-(2-(piperidinoethyl)-3-pyridinecarboxamido, 6-(4-biphenylylmethoxy)-N-(2-piperidinoethyl) nicotinamide, 6-(4-biphenylylmethoxy)-N-[2-(N,N-dimethylamino) ethyl]-nicotinamide, 4-(4-biphenylylmethoxy)-N-(2-piperidinoethyl)benzamide, 4-(4-biphenylylmethoxy)-N-[(2-pyrrolidine-1-yl)ethyl]-benzamide, 2-piperidinoethyl=4-(4-biphenylylethoxy)benzoate, 2-(pyrrolidin-1-yl)ethyl=4-(4-biphenylylmethoxy)benzoate, 4-[4-(biphenylylmethoxy)phenyl]-N-[2-(N,N-dimethylamino)-ethyl]acetamide oxalate, 4-[4-(biphenylylmethoxy)phenyl]-N-[2-(N,N-dimethylamino)-ethyl]acetamide maleate, 4-[4-(biphenylylmethoxy)phenyl]-N-[2-(N,N-dimethylamino)-ethyl]acetamide fumarate, 4-[4-(biphenylylmethoxy)phenyl]-N-[2-(N-methylamino)-ethyl]acetamide hydrochloride, 4-[4-(biphenylylmethoxy)phenyl]-N-[2-(N-methylamino)-ethyl]acetamide, ethyl 7-[2-[4-[(4-biphenylylmethoxy)phenyl]acetylaminoethyl](methyl)amino]heptanoate, 7-[2-[4-[4-(biphenylylmethoxy)phenyl]acetylaminoethyl]-(methyl)amino]heptanoic acid hydrochloride, N-(4-(2-((2-(dimethylamino)ethyl)(methyl)amino)-2-oxoethyl)phenyl)[1,1'-biphenyl]-4-carboxamide, N-(2-aminoethyl)-2-(4-([1,1'-biphenyl]-4-ylmethoxy)phenyl)-acetamide hydrochloride, 4-([1,1'-biphenyl]-4-ylmethoxy)-N-(2-(1-pyrrolidinyl)ethyl)benzamide, N-(4-(2-((2-dimethylamino)ethyl)(methyl)amino)-2-oxoethyl)phenyl)[1,1'-biphenyl]-4-carboxamide, N-[4-({[2-(diethylamino)ethyl]amino}carbonyl)phenyl](4-biphenylyl)carboxamide, 4-(4-biphenylyl)methoxy)-N-[2-(isopropylamino)ethyl]-benzamide, 2-(N,N-diethylamino)ethyl-4-[(4-biphenylyl)carbonyl]amino]-benzoate, N-[4-({[2-(dimethylamino)ethyl]amino}carbonyl)phenyl](4-biphenylyl)carboxamide, N-[4-{[2-(piperidinoethyl)amino]carbonyl}phenyl](4-biphenylyl)carboxamide, or N-[4-({[2-(pyrrolidinyl)ethyl]amino}carbonyl)phenyl](4-biphenylyl)carboxamide.

21. A process for producing the compound according to claim 12 which comprises:

(1) reacting a compound represented by the formula:

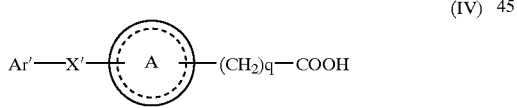

(II)

wherein Xa is oxygen atom, sulfur atom which may be oxidized or imino which may be substituted, and other symbols are as defined in claim 12, or a salt thereof with a compound represented by the formula:

Ar—Xb—L    (III)

wherein Xb is a group corresponding to X' from which Xa is removed, L is a leaving group of hydroxy, and X' and Ar' are as defined in claim 12, or a salt thereof, or (2) reacting a compound represented by the formula:

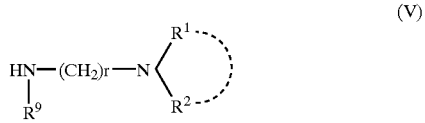

(IV)

wherein each symbol is as defined in claim 12, or a salt thereof with a compound represented by the formula:

(V)

wherein each symbol is as defined in claim 12, or a salt thereof.

22. A prodrug of the compound according to claim 12, wherein an amino group in the compound is acylated, alkylated or phosphorylated; a hydroxy group in the compound is acylated, alkylated, phosphorylated or converted into borate; and/or a carboxy group in the compound is esterified or converted into methyl amide.

23. A pharmaceutical composition which comprises a compound represented by the formula:

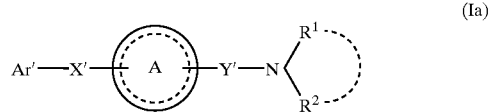

(Ia)

wherein Ar' is aromatic ring assembly group which may be substituted, X' is [1] a group represented by the formula: —$(CH_2)_{p1}$O— wherein $p^1$ is an integer of 1 to 3, [2] —$(CH_2)_{p2}$— wherein $p^2$ is an integer of 1 to 3 or [3] CONH, Y' is [1] a group represented by the formula: —$(CH_2)_{q1}$CONR$^9$$(CH_2)_{r1}$— wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated, or [2] a group represented by the formula: —$(CH_2)_{q2}$COO$(CH_2)_{r2}$— wherein each of $q^2$ and $r^2$ is an integer of 0 to 3 and their sum is not more than 3, each of $R^1$ and $R^2$ is hydrogen atom or $C_{1-6}$ alkyl which may be substituted, or $R^1$ and $R^2$ may form, together with the adjacent nitrogen atom, a 5- or 6-membered nitrogen-containing heterocyclic ring, and ring A is phenylene, provided that 4,4'-[[1,1'-biphenyl]-2,5-diylbis(oxy)]bis[benzoic acid] dihydrazide is excluded, or a salt or a prodrug thereof.

24. The pharmaceutical composition according to claim 23 which is an agent for preventing or treating senile dementia, Alzheimer's disease, Down's syndrome, Parkinson's disease, an amyloid angiopathy or disorder due to amyloid-β protein in a cerebrovascular disorder caused by the production and/or secretion of amyloid-β protein.

25. A method for inhibiting the production and/or the secretion of amyloid-β protein in a mammal, which comprises administering to said mammal an effective amount of a compound represented by the formula:

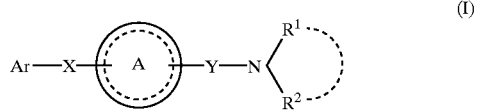

(I)

wherein Ar is an aromatic ring assembly group which may be substituted, X is a bivalent group selected from —O—, —S—, —CO—, —SO—, —$SO_2$—, —$NR^8$—, —$CONR^8$—, —$SO_2NR^8$— and —COO— wherein $R^8$ hydrogen atom, a hydrocarbon group which may be substituted or acyl, or a bivalent $C_{1-6}$ aliphatic hydrocarbon group which may contain one or two of said bivalent groups, Y is [1] a group represented by the formula: —$(CH_2)_{q1}$CONR$^9$$(CH_2)_{r1}$— wherein each of $q^1$ and $r^1$ is an integer of 0 to 3 and their sum is an integer of not more than 3, $R^9$ is hydrogen atom or $C_{1-6}$ alkyl which may be halogenated or $C_{1-6}$ alkyl-carbonyl which may be halogenated, or [2] a group represented by the formula: —$(CH_2)_{q2}$COO$(CH_2)_{r2}$— wherein each of $q^2$ and $r^2$ is an integer of 0 to 3 and their sum is not more than 3, each of $R^1$ and $R^2$ is hydrogen atom or $C_{1-6}$ alkyl which may be substituted, or $R^1$ and $R^2$ may form, together with the adjacent nitrogen atom, a nitrogen-containing heterocyclic ring, and ring A is phenylene, provided that 4,4'-[[1,1'-biphenyl]-2,5-diylbis(oxy)]bis[benzoic acid] dihydrazide is excluded, or a salt or a prodrug thereof.

26. A method for preventing or treating senile dementia, Alzheimer's disease, Down's syndrome, Parkinson's disease, amyloid angiopathy or a disorder due to amyloid-β protein in a cerebrovascular disorder caused by the production and/or secretion of amyloid-β protein, which comprises administering an effective amount of a compound represented by the formula:

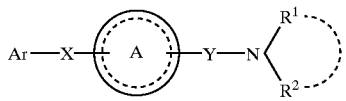
(I)

wherein Ar is an aromatic ring assembly group which may be substituted, X is a bivalent group selected from —O—, —S—, —CO—, —SO—, —SO$_2$—, —NR$^8$—, —CONR$^8$—, —SO$_2$NR$^8$— and —COO— wherein R$^8$ is hydrogen atom, a hydrocarbon group which may be substituted or acyl, or a bivalent $C_{1-6}$ aliphatic hydrocarbon group which may contain one or two of said bivalent groups, Y is [1] a group represented by the formula: —(CH$_2$)$^{q1}$CONR$^9$(CH$_2$)$^{r1}$— wherein each of q$^1$ and r$^1$ is an integer of 0 to 3 and their sum is an integer of not more than 3, R$^9$ is hydrogen atom or $C_{1-6}$ alkyl which may be halogenated or $C_{1-6}$ alkyl-carbonyl which may be halogenated, or [2] a group represented by the formula: —(CH$_2$)$_{q2}$COO(CH$_2$)$_{r2}$— wherein each of q$^2$ and r$^2$ is an integer of 0 to 3 and their sum is not more than 3, each of R$^1$ and R$^2$ is hydrogen atom or $C_{1-6}$ alkyl which may be substituted, or R$^1$ and R$^2$ may form, together with the adjacent nitrogen atom, a nitrogen-containing heterocyclic ring, and ring A is phenylene, provided that 4,4'-[[1,1'-biphenyl]-2,5-diylbis(oxy)]bis[benzoic acid] dihydrazide is excluded, or a salt or a prodrug thereof.

* * * * *

UNITED STATES PATENT AND TRADEMARK OFFICE
CERTIFICATE OF CORRECTION

PATENT NO.   : 6,586,475 B1
DATED        : July 1, 2003
INVENTOR(S)  : Kaneyoshi Kato et al.

It is certified that error appears in the above-identified patent and that said Letters Patent is hereby corrected as shown below:

<u>Title page,</u>
Item [22], PCT Filed, please change "Nov. 16, 1999" to -- Nov. 18, 1999 --.

Signed and Sealed this

Seventh Day of October, 2003

JAMES E. ROGAN
*Director of the United States Patent and Trademark Office*